United States Patent [19]
Dawson et al.

[11] Patent Number: 5,409,950
[45] Date of Patent: Apr. 25, 1995

[54] CYCLIC KETAL DERIVATIVES

[75] Inventors: Michael J. Dawson; Allan Baxter; Robert M. Tait; Nigel S. Watson; David Noble; Alan Shuttleworth; Howard G. Wildman; Michael V. Hayes, all of Greenford, England

[73] Assignee: Glaxo Group Limited, London, England

[21] Appl. No.: 141,061

[22] Filed: Oct. 26, 1993

Related U.S. Application Data

[62] Division of Ser. No. 818,126, Jan. 8, 1992, Pat. No. 5,278,067.

[30] Foreign Application Priority Data

Jan. 9, 1991 [GB] United Kingdom ............... 9100437

[51] Int. Cl.$^6$ .................. A61K 31/335; C07D 311/00
[52] U.S. Cl. ..................................... 514/452; 549/363
[58] Field of Search ........................ 549/363; 514/452

Primary Examiner—Nicky Chan
Attorney, Agent, or Firm—Bacon & Thomas

[57] ABSTRACT

Compounds are described of the formula

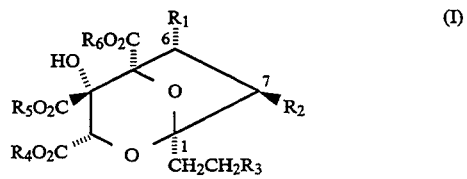

wherein $R_1$ represents a hydrogen atom, a hydroxyl group or a group selected from —O-COCH$\stackrel{E}{=}$CHCH(CH$_3$)(CH$_2$)$_3$CH$_3$, —O-COCH$\stackrel{E}{=}$CHC(CH$_3$)$\stackrel{E}{=}$CHCH(CH$_3$)—CH$_2$CH$_3$, or —OCO—X—CH$_2$CH(CH$_3$)CH$_2$CH$_3$ [where X is —CH$\stackrel{E}{=}$CHCH(CH$_3$)—, —CH$_2$CH(OH)CH(CH$_3$)—, —CH$\stackrel{E}{=}$CHC(OH)(CH$_3$)—, —CH$_2$CH(OH)CH$_2$— or —CH$_2$CH$_2$CH(CH$_3$)—)];

$R_2$ represents a hydrogen atom or a hydroxyl group;

$R_3$ represents a group selected from —C(=CH$_2$)CH(OR$_7$)CH(CH$_3$)CH$_2$Ph (where R$_7$ is a hydrogen atom or an acetyl group), —C(CH$_3$)$\stackrel{E}{=}$CHCH(CH$_2$R$_8$)CH$_2$Ph (where R$_8$ is a hydrogen or a hydroxyl group), —C(CH$_2$OH)$\stackrel{Z}{=}$CHCH(CH$_3$)CH$_2$Ph, —C(=CH$_2$)CH(OH)CH(CH$_2$OH)CH$_2$Ph, —C(=CH$_2$)CH(NHCOCH$_3$)CH(CH$_3$)CH$_2$Ph, —C(CH$_2$NHCOCH$_3$)$\stackrel{E}{=}$CHCH(CH$_3$)CH$_2$Ph or

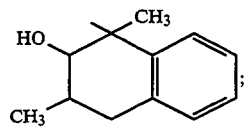

$R_4$, $R_5$ and $R_6$ may each independently represent a hydrogen atom or a methyl group and salts thereof; with the proviso that when either of $R_1$ and $R_2$ represents a hydrogen atom $R_3$ is a group selected from —C(=CH$_2$)CH(OR$_7$)CH(CH$_3$)CH$_2$Ph and —C(CH$_3$)$\stackrel{E}{=}$CHCH(CH$_3$)CH$_2$Ph and when both of $R_1$ and $R_2$ represent hydrogen atoms $R_3$ represents —C(CH$_3$)$\stackrel{E}{=}$CHCH(CH$_3$)CH$_2$Ph.

These compounds inhibit the enzyme squalene synthase and/or are intermediates for the preparation of compounds which inhibit the enzyme squalene synthase. Compounds of the invention may be formulated for use in a variety of conditions where a lowering of the level of blood plasma cholesterol in animals would be beneficial and for use in combating fungal infections in animals.

14 Claims, 1 Drawing Sheet

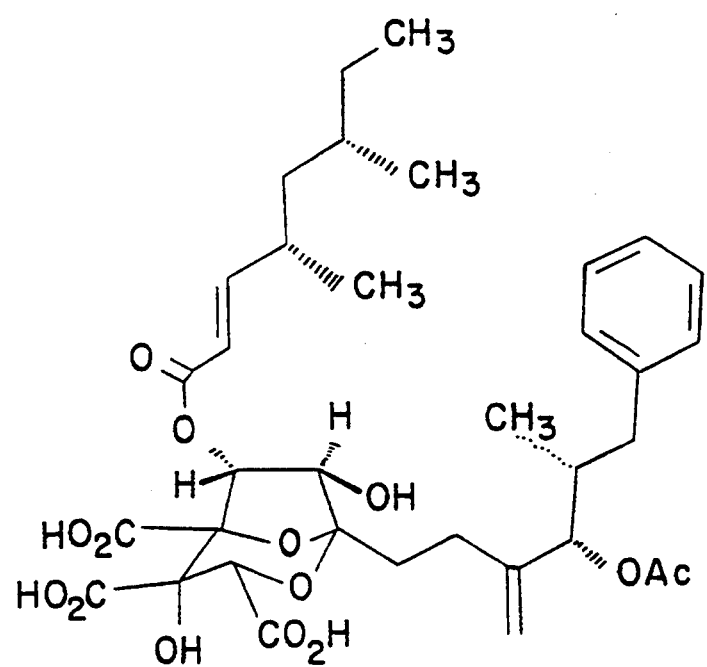

CYCLIC KETAL DERIVATIVES

This application is a division of application Ser. No. 07/818,126 filed Jan. 8, 1992, now U.S. Pat. No. 5,278,067.

This invention relates to novel compounds having hypocholesterolemic, hypolipidemic and/or antifungal activity, to processes for their preparation, to pharmaceutical compositions containing them and to their use in medicine, particularly in the treatment and/or prevention of atherosclerosis and associated cardiovascular diseases. The invention also relates to novel compounds which are useful as intermediates for the preparation of compounds having hypocholesterolemic, hypolipidemic and/or antifungal activity.

High levels of blood cholesterol and blood lipids are conditions which are implicated in the onset of vessel wall disease. Methods for effective reduction of plasma cholesterol levels are there/ore of high interest. Cholesterol concentrations can be reduced, for example, by lowering the dietary intake of the sterol, by enhancing its metabolism and elimination or by decreasing its rate of biosynthesis. The most effective approaches to lowering physiological cholesterol levels are likely to include inhibition of cholesterol biosynthesis as a component since cholesterol synthesis is subject to feedback regulation, so that decreases in cholesterol levels tend to be compensated for by increased biosynthesis.

One rate-controlling step in the biosynthesis of cholesterol is the formation of mevalonic acid from 3-hydroxy-3-methylglutaryl coenzyme A (HMG CoA) and clinical successes have been achieved with the mevinic acid family of HMG CoA reductase inhibitors in the treatment of hypercholesterolemia. Mevalonic acid, however, is a common precursor of all isoprenyl derivatives, including in animals coenzyme Q, heme A and the dolichols.

The first biosynthetic step which leads exclusively to sterols, the condensation of two farnesyl pyrophosphates to give squalene, is a second site of regulation. The synthesis of squalene from farnesyl pyrophosphate involves an isolable intermediate, presqualene pyrophosphate, and the entire synthetic sequence is catalysed by squalene synthase (farnesyldiphosphate: farnesyldiphosphate farnesyltransferase, EC 2.5.1.21), a membrane-bound enzyme. Agents which act to inhibit the enzyme squalene synthase are therefore potential drugs for the regulation of cholesterogenesis. The use of such agents is attractive as non-steroidal pathways should be minimally affected.

The biosynthesis of ergosterol, the major sterol component of fungal cell membranes, is analogous to that of cholesterol in mammals, including humans, and is thus mediated by the enzyme squalene synthase. Agents which act to inhibit the enzyme squalene synthase in fungal cells are therefore potential drugs for antifungal chemotherapy.

We have now found a group of novel compounds which act as inhibitors of the enzyme squalene synthase and/or are intermediates for the preparation of compounds which act as inhibitors of the enzyme squalene synthase.

Thus, in a first aspect of the present invention, we provide compounds of the general formula (I)

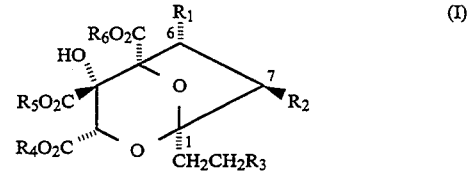

wherein $R_1$ represents a hydrogen atom, a hydroxyl group or a group selected from $-O-COCH\overset{E}{=}CHCH(CH_3)(CH_2)_3CH_3$, $-O-COCH\overset{E}{=}CHC(CH_3)\overset{E}{=}CHCH(CH_3)-CH_2CH_3$, or $-OCO-X-CH_2CH(CH_3)CH_2CH_3$ [where X is $-CH\overset{E}{=}CHCH(CH_3)-$, $-CH_2CH(OH)CH(CH_3)-$, $-CH\overset{E}{=}CHC(OH)(CH_3)-$, $-CH_2CH(OH)CH_2-$ or $-CH_2CH_2CH(CH_3)-)$];

$R_2$ represents a hydrogen atom or a hydroxyl group;

$R_3$ represents a group selected from $-C(=CH_2)CH(OR_7)CH(CH_3)CH_2Ph$ (where $R_7$ is a hydrogen atom or an acetyl group), $-C(CH_3)\overset{E}{=}CHCH(CH_2R_8)CH_2Ph$ (where $R_8$ is a hydrogen or a hydroxyl group), $-C(CH_2OH)\overset{Z}{=}CHCH(CH_3)CH_2Ph$, $-C(=CH_2)C-H(OH)CH(CH_2OH)CH_2Ph$, $-C(=CH_2)CH(NHCOCH_3)CH(CH_3)CH_2Ph$, $-C(CH_2NHCOCH_3)\overset{E}{=}CHCH(CH_3)CH_2Ph$ or

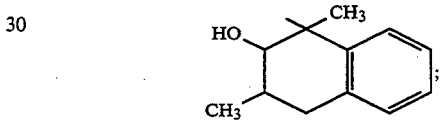

$R_4$, $R_5$ and $R_6$ may each independently represent a hydrogen atom or a methyl group and salts thereof; with the proviso that when either of $R_1$ and $R_2$ represents a hydrogen atom $R_3$ is a group selected from $-C(=CH_2)CH(OR_7)CH(CH_3)CH_2Ph$ and $-C(CH_3)\overset{E}{=}CHCH(CH_3)CH_2Ph$ and when both of $R_1$ and $R_2$ represent hydrogen atoms $R_3$ represents $-C(CH_3)\overset{E}{=}CHCH(CH_3)CH_2Ph$.

In a second aspect of the present invention, we provide compounds of formula (I) as defined above, except those compounds in which $R_1$ represents $-O-COCH\overset{E}{=}CHCH(CH_3)CH_2CH(CH_3)CH_2CH_3$, $R_2$ represents a hydroxyl group, $R_3$ represents $-C(=CH_2)C-H(OCOCH_3)CH(CH_3)CH_2Ph$ and $R_4$, $R_5$ and $R_6$ independently represent hydrogen or methyl.

In one embodiment of the present invention we provide compounds having the general formula (Ia)

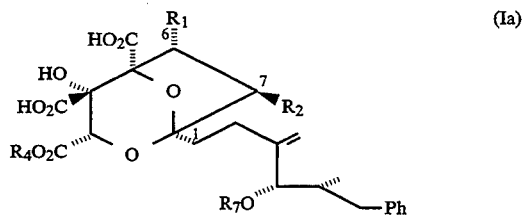

wherein $R_1$, $R_2$, $R_4$ and $R_7$ are as defined above and salts thereof; with the proviso that when $R_2$ represents a hydrogen atom then $R_1$ represents a group $-O-COCH\overset{E}{=}CHCH(CH_3)CH_2CH(CH_3)CH_2CH_3$.

In another embodiment of the present invention we provide compounds having the general formula (Ib)

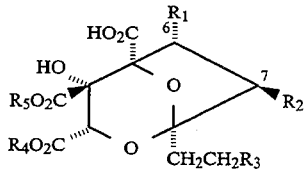

(Ib)

wherein $R_1$ represents a hydrogen atom, a hydroxyl group or a group

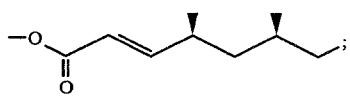

$R_2$ represents a hydrogen atom or a hydroxyl group; $R_3$ represents a group selected from —C(CH$_3$)$\overset{E}{=}$CHCH(CH$_2$R$_8$)CH$_2$Ph (where $R_8$ is a hydrogen atom or a hydroxyl group), —C(CH$_2$OH)$\overset{Z}{=}$CHCH(CH$_3$)CH$_2$Ph, —C(=CH$_2$)CH(OH)CH(CH$_2$OH)CH$_2$Ph, —C(=CH$_2$)CH(NHCOCH$_3$)CH(CH$_3$)CH$_2$Ph, —C(CH$_2$NHCOCH$_3$)$\overset{E}{=}$CHCH(CH$_3$)CH$_2$Ph or

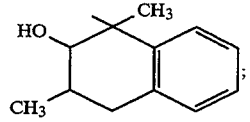

$R_4$ represents a hydrogen atom or a methyl group; and salts thereof, with the provisos that (1) when $R_1$ represents a hydrogen atom then $R_3$ must represent —C(CH$_3$)$\overset{E}{=}$CHCH(CH$_3$)CH$_2$Ph (2) when $R_1$ represents

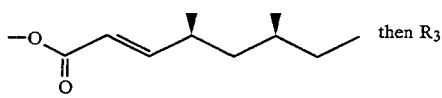

then $R_3$ must represent a group selected from —C(CH$_3$)$\overset{E}{=}$CHCH(CH$_3$)CH$_2$Ph, —C(=CH$_2$)CH(OH)CH(CH$_2$OH)CH$_2$Ph, —C(=CH$_2$)CH(NHCOCH$_3$)CH(CH$_3$)CH$_2$Ph or C(CH$_{21}$NHCOCH$_3$)$\overset{E}{=}$CHCH(CH$_3$)CH$_2$Ph (3) when $R_2$ represents a hydrogen atom then $R_3$ must represent a group —C(CH$_3$)$\overset{E}{=}$CHCH(CH$_3$)CH$_2$Ph.

A preferred group of compounds of formula (I) are compounds of formula (Ia) and salts thereof.

Another preferred group of compounds of formula (I) are compounds of formula (Ib) and salts thereof, in which $R_1$ represents —O-COCH$\overset{E}{=}$CHCH(CH$_3$)CH$_2$CH(CH$_3$)CH$_2$CH$_3$, $R_2$ represents a hydroxyl group and $R_3$ is —C(=CH$_2$)CH(OH)CH(CH$_2$OH)CH$_2$Ph, —C(=CH$_2$)CH(NHCOCH$_3$)CH(CH$_3$)CH$_2$Ph, —C(CH$_2$NHCOCH$_3$)$\overset{E}{=}$CHCH(CH$_3$)CH$_2$Ph or —C(CH$_3$)$\overset{E}{=}$CHCH(CH$_3$)CH$_2$Ph.

Compounds of the invention in which $R_2$ represents a hydroxyl group may be generally preferred.

Compounds of the invention in which $R_4$, $R_5$ and $R_6$ represent hydrogen atoms or physiologically acceptable cations are generally preferred.

Compounds of formula (Ib) in which $R_1$ represents a hydrogen atom or a hydroxyl group are useful as intermediates for the preparation of related structures having squalene synthase inhibitory activity.

Compounds of formula (Ia) in which $R_1$ represents a hydroxyl group or a group

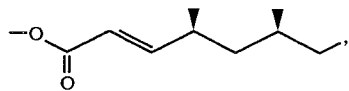

$R_2$ represents a hydroxyl group and $R_4$ represents a hydrogen atom and salts thereof are particularly useful as intermediates for the preparation of related structures having squalene synthase inhibitory activity.

It is to be understood that this invention covers any combination of the aforementioned particular and preferred groupings.

An active compound of the invention particularly preferred as an intermediate for the preparation of structurally related compounds also having squalene synthase inhibitory activity is Compound A hereinafter and its salts.

Other compounds of the invention particularly preferred as intermediates for the preparation of structurally related compounds having squalene synthase activity are Compounds B and C hereinafter and their salts.

The following Table 1 lists particular compounds of the present invention with reference to formula (Ia) or formula (Ib) above. Each individual compound depicted represents a further preferred aspect of the present invention.

TABLE 1

| COMPOUND | GENERAL FORMULA | $R_1$ | $R_2$ | $R_3$ | $R_4$ | $R_7$ |
|---|---|---|---|---|---|---|
| A | Ia | OCOCH=CHCH$_2$CHCH$_2$CH$_3$ (CH$_3$, CH$_3$, E) | OH | — | H | COCH$_3$ |
| B | Ia | OCOCH=CHCH$_2$CHCH$_2$CH$_3$ (CH$_3$, CH$_3$, E) | OH | — | H | H |
| C | Ia | OH | OH | — | H | COCH$_3$ |
| D | Ia | OCOCH=CHCH$_2$CHCH$_2$CH$_3$ (CH$_3$, CH$_3$, E) | OH | — | CH$_3$ | COCH$_3$ |
| E | Ia | OCOCH=CHCH$_2$CHCH$_2$CH$_3$ (CH$_3$, CH$_3$, E) | OH | — | CH$_3$ | H |
| F | Ia | OH | OH | — | H | H |
| G | Ia | OCOCH=CHCH(CH$_3$)(CH$_2$)$_3$CH$_3$ | OH | — | H | COCH$_3$ |
| H | Ia | OCOCH=CHC(CH$_3$)=CHCH(CH$_3$)CH$_2$CH$_3$ (E) | OH | — | H | COCH$_3$ |
| I | Ia | OCOCH$_2$CH(OH)CH(CH$_3$)CH$_2$CH(CH$_3$)CH$_2$CH$_3$ | OH | — | H | COCH$_3$ |
| J | Ia | OCOCH=CH(OH)(CH$_3$)CH$_2$CH(CH$_3$)CH$_2$CH$_3$ (E) | OH | — | H | COCH$_3$ |
| K | Ia | OCOCH=CH(OH)(CH$_3$)CH$_2$CH(CH$_3$)CH$_2$CH$_3$ | OH | — | H | COCH$_3$ |
| L | Ia | OCOCH$_2$CH(OH)CH$_2$CH$_2$CH(CH$_3$)CH$_2$CH$_3$ | OH | — | H | COCH$_3$ |
| M | Ia | OCOCH$_2$CH(OH)CH(CH$_3$)CH$_2$CH(CH$_3$)CH$_2$CH$_3$ | OH | — | H | H |
| N | Ib | OCOCH=CHCH$_2$CHCH$_2$CH$_3$ (CH$_3$, CH$_3$, E) | OH | C(=CH$_2$)CH(OH)CH(CH$_2$OH)CH$_2$Ph | H | — |
| O | Ia | OCOCH=CHCH$_2$CHCH$_2$CH$_3$ (CH$_3$, CH$_3$, E) | H | — | H | COCH$_3$ |
| P | Ib | OH | OH | C(CH$_3$)=CHCH(CH$_2$OH)CH$_2$Ph (E) | H | — |

TABLE 1-continued

| COMPOUND | GENERAL FORMULA | R₁ | R₂ | R₃ | R₄ | R₇ |
|---|---|---|---|---|---|---|
| Q | Ib | OH | OH | Z C(CH₂OH)=CHCH(CH₃)CH₂Ph | H | — |
| R | Ib | OH | OH | E C(CH₃)=CHCH(CH₃)CH₂Ph | H | — |
| S | Ib | OH | OH | 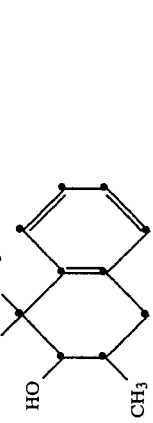 | H | — |
| T | Ib | E OCOCH=CHCHCH₂CHCH₂CH₃ (CH₃, CH₃) | OH | E C(CH₂NHCOCH₃)=CHCH(CH₃)CH₂Ph | H | — |
| U | Ia | OCOCH₂CH₂CH(CH₃)CH₂CH(CH₃)CH₂CH₃ | OH | — | H | COCH₃ |
| V | Ia | H | OH | — | H | COCH₃ |
| W | Ia | OCOCH₂CH(OH)CH₂CH₂CH(CH₃)CH₂CH₃ | OH | — | H | H |
| X | Ib | H | OH | E C(CH₃)=CHCH(CH₃)CH₂Ph | H | — |
| Y | Ib | OH | H | E C(CH₃)=CHCH(CH₃)CH₂Ph | H | — |
| Z | Ib | H | H | E C(CH₃)=CHCH(CH₃)CH₂Ph | H | — |
| A1 | Ib | E OCOCH=CHCHCH₂CHCH₂CH₃ (CH₃, CH₃) | OH | E C(CH₃)=CHCH(CH₃)CH₂Ph | H | — |
| B1 | Ib | E OCOCH=CHCHCH₂CHCH₂CH₃ (CH₃, CH₃) | OH | C(=CH₂)CH(NHCOCH₃)CH(CH₃)CH₂Ph | H | — |
| C1 | Ia | E OCOCH=CHC(OH)(CH₃)CH₂CH(CH₃)CH₂CH₃ | OH | — | H | H |

Compounds A, B, C, D, E, F, O and V have the absolute configurations assigned to them hereinabove. Thus, Compound A is the compound [1S-[1α(4R*,5S*),3α,4β,5=,6α(2E,4R*,6R*),7β]]1-(4-acetyloxy-5-methyl-3-methylene-6-phenylhexyl)-4,6,7-trihydroxy-2,8-dioxabicyclo[3.2.1]octane-3,4,5-tricarboxylic acid, 6-(4,6-dimethyl-2-octenoate); Compound B is the compound [1S-[1α(4R*,5S*),3α,4β,5α,6α(2E,4R*,6R*),7β9 ]]1-(4-hydroxy-5-methyl-3-methylene-6-phenylhexyl)-4,6,7-trihydroxy-2,8-dioxabicyclo[3.2.1]octane-3,4,5-tricarboxylic acid, 6-(4,6-dimethyl-2-octenoate); Compound C is the compound [1S-]1α(4R*,5S*)-,3α,4β,5α,6α,7β]]1-(4-acetyloxy-5-methyl-3-methylene-6-phenylhexyl)-4, 6,7-trihydroxy-2,8-dioxabicyclo[3.2.1 ]octane-3,4,5-tricarboxylic acid; Compound D is the compound [1S-[1α(4R*,5S*),3α,4β,5α,6α(2E,4R*,6R*),7β]]1-(4-acetyloxy-5-methyl-3-methylene-6-phenylhexyl)-4,6,7-trihydroxy-2,8-dioxabicyclo[3.2.1]octane-3,4,5-tricarboxylic acid, 6-(4,6-dimethyl-2-octenoate), 3-methyl ester; Compound E is the compound [1S-[1α(4R*,5S*),3α,4β,5α,6α(2E,4R*,6R*),7β]]1-(4-hydroxy-5-methyl-3-methylene-6-phenylhexyl)-4,6,7-trihydroxy-2,8-dioxabicyclo[3.2.1]octane-3,4,5-tricarboxylic acid, 6-(4,6-dimethyl-2-octenoate), 3-methyl ester; Compound F is the compound [1S-[1α(4R*,5S*),3α,4β,5α,6α,7β]]1-(4-hydroxy-5-methyl-3-methylene-6-phenylhexyl)-4,6,7-trihydroxy-2,8-dioxabicyclo[3.2.1]octane-3,4,5-tricarboxylic acid; Compound O is the compound [1S-[1α(4R*,5S*),3α,4β,5α,6α(2E,4R*,6R*)]]1-(4-acetyloxy-5-methyl-3-methylene-6-phenylhexyl)-4,6-dihydroxy-2,8-dioxabicyclo[3.2.1]octane-3, 4,5-tricarboxylic acid, 6-(4,6-dimethyl-2-octenoate) and Compound V is the compound [1S-[1α(4R*,5S*),3α,4β,5α,7β]]1-(4-acetyloxy-5-methyl-3-methylene-6-phenylhexyl)-4,7-dihydroxy-2,8-dioxabicyclo[3.2.1]octane-3,4,5-tricarboxylic acid.

Compounds G, H, I, J, K, L, M, U, W and C1 are 6-acyl derivatives of Compound C or of Compound F as appropriate. Hence, the unit common to Compounds G, H, I, J, K, L, M, U, W and C1 and Compound C or Compound F has the absolute stereochemistry defined for Compound C or Compound F.

Compounds N, T, A1 and B1 are structurally related to Compound B. Hence, the unit common to Compounds N, T, A1 and B1 and Compound B has the absolute stereochemistry defined for Compound B. However, the C-1 side chains in Compounds N, T, A1 and B1 are different from that in Compound B and the stereochemistry of the C-1 side chain substituents in Compounds N, T, A1 and B1 are undefined.

Compounds P, Q, R and S are structurally related to Compound C. Hence, the unit common to Compounds P, Q, R and S and Compound C has the absolute stereochemistry defined for Compound C. However, the C-1 side chain in each of Compounds P, Q, R and S is significantly different from that in Compound C and the stereochemistry of the C-1 side chain substituents in each of Compounds P, Q, R and S is undefined.

Compound X is structurally related to Compound V. Hence, the unit common to Compound X and Compound V has the absolute stereochemistry defined for Compound V. However, the C-1 side chain is significantly different from that in Compound V and the stereochemistry of the C-1 side chain substituent in Compound X is undefined.

Compound Y is a 7-dehydroxylated analogue of Compound C. Hence, the unit common to Compound Y and Compound C has the absolute stereochemistry defined for Compound C. However, the C-1 side chain is significantly different from that in Compound C and the stereochemistry of the C-1 side chain substituent in Compound Y is undefined.

Compound Z is a 7-dehydroxylated analogue of Compound V. Hence, the common unit to Compound Z and Compound V has the absolute stereochemistry defined for Compound V. However, the C-1 side chain is significantly different from that in Compound V and the stereochemistry of the C-1 side chain substituent in Compound Z is undefined.

The absolute configuration of Compound A was established by degradation studies. In particular, Compound A was hydrolysed to provide Compound F. The side chain removed by hydrolysis was isolated and established to be S(R*,R*)-(E)-4,6-dimethyl-2-octenoic acid (i.e. [4S, 6S(E)]-4,6-dimethyl-2-octenoic acid) from a two-step conversion to the compound S(R*,R*)methyl 2,4-dimethylhexanoate (i.e. (2S,4S)-2,4-dimethylhexanoic acid, methyl ester). A combination of spectroscopic and X-ray studies together with the identification of the side chain S(R*,R*)-(E)-4,6-dimethyl-2-octenoic acid established that Compound A has the structure and absolute configuration assigned to it herein.

BRIEF DESCRIPTION OF DRAWINGS

FIG. 1 hereinafter is a three-dimensional structural representation of Compound A.

Compounds of the present invention may form salts with inorganic and organic bases. Physiologically acceptable salts include inorganic base salts such as alkali metal salts (e.g. sodium and potassium salts including the trisodium, dipotassium and tripotassium salts), alkaline earth metal salts (e.g. calcium salts), ammonium salts and amino acid salts (e.g. lysine and arginine salts including the tri-L-lysine salts). Suitable organic base salts include amine salts such as trialkylamine (e.g. triethylamine), dialkylamine (e.g. dicyclohexylamine), optionally substituted benzylamine (e.g. p-bromobenzylamine) and tris(hydroxymethyl)methylamine salts.

Compounds of the invention have been found to inhibit the enzyme squalene synthase and cholesterol biosynthesis and are therefore of use in medicine, particularly in a variety of conditions where a lowering of the level of blood plasma cholesterol in animals (especially humans) would be beneficial. Examples of such conditions include diseases associated with hypercholesterolemia and hyperlipoproteinemia, especially atherosclerosis and cardiovascular diseases (such as cardiac ischaemic diseases, cerebral ischaemic diseases and peripheral arterial disease).

Compounds of the invention which inhibit squalene synthase may also be of use in combating fungal infections in animals, including humans. For example, they may be useful in the treatment of systemic infections caused by, for example Candida (e.g. Candida albicans, Candida glabrata, Candida parapsilosis and Candida pseudotrop), Cryptococcus neoformans, Aspergillus Sp (e.g. Aspergillus flavus and Aspergillus fumigatus), Coccidioides (e.g. Coccidioides immitis, Paracoccidioides (e.g. Paracoccidioides brasiliensis), Histoplasma (e.g. Histoplasma capsulatum) or Blastomyces (e.g. Blastomyces dermatitidis). They may also be useful in treating topical infections caused by species of Trichophyton, Microsporum or Epidermophyton (e.g. Trichophyton mentographytes, Microsporum canis or Epidermophyton floccosum). They may also be of use in treating fungal diseases caused by Torulopsis glabrata and Pityrosporum ovale.

The in vitro evaluation of the anti-fungal activity of compounds of the invention can be performed by determining the minimum inhibitory concentration (MIC) which is the concentration of the test compound in a suitable medium at which growth of a particular microorganism fails to occur.

In view of their potential in antifungal therapy, compounds of the invention which inhibit squalene synthase may recommend themselves for the treatment of a variety of fungal infections in human beings and animals. Such infections include mycotic infections such as candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityfiasis versicolor, erythrasma, intertrigo, fungal nappy rash, candida vulvitis, candida balanitis and otitis externa. They may also be useful as prophylactic agents to prevent systemic and topical fungal infections. Use as prophylactic agents may, for example, be appropriate as part of a selective gut decontamination regimen in the prevention of infection in immunocompromised patients. Prevention of fungal overgrowth during antibiotic treatment may also be desirable in some disease syndromes or iatrogenic states.

The ability of compounds of the invention to inhibit the enzyme squalene synthase in mammals and fungi may be demonstrated in vitro using [2-$^{14}$C]farnesylpyrophosphate as a substrate under assay conditions similar to those described by S. A. Biller et al. in J. Medicinal Chemistry 31(10), 1869–1871 (1988); [$^{14}$C]squalene is separated from unreacted substrate on thin layer chromatography plates and determined by liquid scintillation counting. The ability of compounds of the invention to inhibit cholesterol biosynthesis may be demonstrated by measuring inhibition from [$^{14}$C]-acetate in liver slices from male Wistar rats using a method similar to that described by Y. Tsujita et al. in Biochem. Biophys. Acta, Volume 877, 50–60 (1986) and modified to include measurement of cholesterol by high performance liquid chromatography (h.p.l.c.).

While it is possible that, for use in therapy, compounds of the invention which inhibit squalene synthase may be administered as the raw chemical, it is preferable to present the active ingredient as a pharmaceutical formulation. The invention thus further provides a pharmaceutical formulation comprising compounds of the invention which inhibits squalene synthase together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, rectal, topical, ophthalmic or genitourinary administration or in a form suitable for administration by inhalation or insufflation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/-sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents, e.g. stabilising and solubilising agents. Pessaries and tampons for vaginal insertion may be formulated using conventional techniques and, where appropriate, may contain an effervescent vehicle. Such compositions may also contain other active ingredients such as conicosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilising and/or dispersing agents.

Transdermal administration may be affected by the design of a suitable system which promotes adsorption of the active compound through the skin and would typically consist of a base formulation enclosed within an adhesive stick-on patch comprising backing films, membranes and release liners.

The composition according to the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.001mg to 1000mg, advantageously 0.01mg to 400mg, of active ingredient where a compound of the invention is to be administered orally. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary numbers of days.

Compounds of the invention which inhibit squalene synthase may also be used in combination with other therapeutic agents, and the invention thus provides, in a further aspect, a combination comprising a compound of the invention which inhibits squalene synthase together with another therapeutically active agent, such as an inhibitor of 3-hydroxy-3-methylglutaryl coenzyme A (HMG CoA) reductase or another agent which reduces serum cholesterol and/or inhibits cholesterol biosynthesis, for example a bile acid sequestrant or an antihyperlipoproteinemic or antihyperlipemic agent such as probucol, gemfibrozil, clofibrate, dextrothyroxine or its sodium salt, colestipol or its hydrochloride salt, cholestyramine, nicotinic acid, neomycin, p-aminosalicylic acid, aspirin, DEAE-Sephadex, a poly(-diallylmethylamine) derivative, an ionene or poly(diallyldimethylammonium) chloride.

The combinations referred to above may conveniently be presented for use in the form of a pharmaceutical formulation and thus pharmaceutical formulations comprising a combination as defined above together with a pharmaceutically acceptable career thereof comprise a further aspect of the invention. The individual components of such combinations may be administered either sequentially or simultaneously in separate or combined pharmaceutical formulations.

When a compound of the invention is used in combination with a second therapeutic agent against the same condition the dose of each compound may differ from that when the compound is used alone. Appropriate doses will be readily appreciated by those skilled in the art.

According to another aspect of the present invention, we provide a suitable compound of the invention or a pharmaceutical composition comprising a suitable compound of the invention as defined above for use in therapy, particularly for the treatment of conditions where a lowering of the level of blood plasma cholesterol in animals (especially humans) would be beneficial, or for the treatment of fungal infections in animals (especially humans).

In a particular aspect of the present invention, we provide a suitable compound of the invention or a pharmaceutical composition comprising a suitable compound of the invention as defined above for use in the treatment of diseases associated with hypercholesterolemia and/or hyperlipoproteinemia, especially atherosclerosis and cardiovascular diseases (such as cardiac ischaemic diseases, cerebral ischaemic diseases and peripheral arterial disease).

According to a further aspect of the present invention, we provide the use of a compound of the invention in the manufacture of a medicament for the treatment of diseases associated with hypercholesterolemia and/or hyperlipoproteinemia, especially atherosclerosis and cardiovascular diseases (such as cardiac ischaemic diseases, cerebral ischaemic diseases and peripheral arterial disease).

According to another aspect of the present invention, we provide the use of a compound of the invention in the manufacture of a medicament for the treatment of fungal infections in a human or non-human animal patient.

According to a further aspect of the present invention, we provide a method of treatment of the human or non-human animal body to combat diseases associated with hypercholesterolemia and/or hyperlipoproteinemia, especially atherosclerosis and cardiovascular diseases (such as cardiac ischaemic diseases, cerebral ischaemic diseases and peripheral arterial disease) or to combat fungal diseases, which method comprises administering to said body an effective amount of a compound of the invention which inhibits squalene synthetase.

It will be appreciated by those skilled in the art that references herein to treatment extend to prophylaxis as well as the treatment of established conditions or infections.

The compounds of the invention may be prepared by the processes described below.

Thus, according to a further aspect of the present invention, we provide a process for the preparation of the compounds of the invention which comprises the step of cultivating a microorganism capable of producing one or more of the compounds of the invention and thereafter isolating the desired compound from the culture and, if desired, deacylating the said compound and/or esterifying the said compound to the corresponding methyl ester.

Microorganisms capable of producing a compound of the invention may readily be identified by using a small scale test and analysing a test sample obtained from a fermentation of the microorganism using standard methodology.

In particular the microorganism to be conventionally used is a strain of microorganism deposited on 31st May 1989 in the culture collection of Glaxo Group Research Limited, Microbiology Division, Greenford Road, Greenford, Middlesex, England, UB6 0HE (collection number 202 in the World Directory of Collections of Cultures of Microorganisms, 1982; curator: Miss A M Harris) under accession no. C2932 or a mutant thereof. It is to be understood that the above mentioned culture collection centre has given its unreserved and irrevocable consent to the microorganism deposited being made available to any person making a valid request therefor to the culture collection in accordance with Rule 17 of the UK Patents Rules 1982.

The strain deposited at Greenford under accession no. C2932 has also been deposited in the permanent culture collection of the CAB International Mycological Institute, Ferry Road, Kew, Surrey, England. The strain was received by the Institute on 25th May 1989 and was subsequently given the accession no. IMI 332962 and a deposit date of 27th Jun. 1989 (date of confirmation of viability). The deposited strain is identified herein by reference to the Institute accession no. IMI 332962. The characteristics thus far identified for IMI 332962 are given in Example 40 hereinafter.

The present invention provides in a further aspect the microorganism IMI 332962 per se and routants thereof.

Mutants of the IMI 332962 may arise spontaneously or may be produced by a variety of methods including those outlined in Techniques for the Development of Micro-organisms by H. I. Adler in 'Radiation and Radioisotopes for Industrial Microorganisms', Proceedings of the Symposium, Vienna 1973, p241, International Atomic Energy Authority. Such methods include ionising radiation, chemical methods e.g. treatment with N-methyl-N'-nitro-N-nitrosoguanidine (NTG), heat, genetic techniques, such as recombination and transformation, and selective techniques for spontaneous mutants.

According to a still further aspect of the invention we provide the genetic material of IMI 332962 and mutants thereof that participates in the synthesis of one or more of the compounds of the invention. Such material may be obtained using conventional genetic engineering techniques including those outlined by Rambosek and Leach in "Recombinant DNA in filamentous fungi: progress and prospects", CRC Critical Reviews in Biotechnology 1987, volume 6, pages 357–393.

Such techniques may be used in a similar manner to that described previously for cloning antibiotic biosynthetic genes for $\beta$-lactam antibiotic biosynthesis in Acremonium chrysogenum (Sansom, S. M. et al., 1985, Nature, 318, p191-194). The genetic material so obtained may be used, for example, for strain improvement as described by Skatrud, P. L. et al, 1989, Bio/-Technology 7, pages 477–485), for production of biosynthetic enzymes for in vitro applications, or for generating novel compounds by introduction of such material into organisms other than IMI 332962.

In a further aspect of the invention we provide the bridged cyclic ketal derivatives obtainable from the fermentation of IMI 332962 or a mutant thereof, deacylated derivatives thereof and their methyl esters.

In a particular aspect of the invention we provide the compounds having squalene synthase inhibitory activity obtainable from the fermentation of IMI 332962 or a mutant thereof, deacylated derivatives thereof and their methyl esters.

Twelve further products of the fermentation of IMI 332962 have also been isolated and are referred to hereinafter as Compounds D1 to N1 and P1.

Thus, in another aspect of the present invention we provide Compounds D1 to N1 and P1 obtainable from the fermentation of IMI 332962, and salts thereof.

In a further aspect of this invention, we provide Compounds D1 to N1 having the physical characteristics given in Tables 2, 3 and 4 hereinafter.

The production of compounds of the invention by fermentation of a suitable organism may be effected by conventional means i.e. by culturing the organism in the presence of assimilable sources of carbon, nitrogen and mineral salts.

Assimilable sources of carbon, nitrogen and minerals may be provided by either simple or complex nutrients. Sources of carbon will generally include glucose, maltose, starch, glycerol, molasses, dextrin, lactose, sucrose, fructose, galactose, myo-inositol, D-mannitol, soya bean oil, carboxylic acids, amino acids, glycerides, alcohols, alkanes and vegetable oils. Sources of carbon will generally comprise from 0.5 to 10% by weight of the fermentation medium. Fructose, glucose and sucrose represent preferred sources of carbon.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium potassium, ammonium, iron, magnesium, zinc, nickel, cobalt, manganese, vanadium, chromium, calcium, copper, molybdenum, boron, phosphate, sulphate, chloride and carbonate ions.

Cultivation of the organism will generally be effected at a temperature of from 20° to 400° C. preferably from 20° to 35° C., especially around 25° to 280° C., and will desirably take place with aeration and agitation e.g. by shaking or stirring. The medium may initially be inoculated with a small quantity of mycelium and/or spores. The vegetative inoculum obtained may be transferred to the fermentation medium, or to one or more seed stages where further growth takes place before transfer to the principal fermentation medium. The fermentation will generally be carded out in the pH range 3.5 to 9.5, preferably 4.5 to 7.5. It may be necessary to add a base or an acid to the fermentation medium to keep the pH within the desired range. Suitable bases which may be added include alkali metal hydroxides such as aqueous sodium hydroxide or potassium hydroxide. Suitable acids include mineral acids such as hydrochloric, sulphuric or phosphoric acid. The fermentation may be carried out for a period of 4–30 days, preferably about 7–18 days. An antifoam may be present to control excessive foaming and added at intervals as required. Carbon and/or nitrogen sources may also be fed into the fermentation medium as required.

Compounds of the invention may be present in both the fermentation liquor and the mycelial fraction, which may conveniently be separated by filtration or centrifugation. The liquor may be optionally thereafter treated with an acid such as sulphuric acid in the presence of an organic solvent until the pH is below pH 6 (e.g. about pH 3).

Compounds of the invention may be separated from the fermentation broth by conventional isolation and separation techniques. It will be appreciated that the choice of isolation techniques may be varied widely.

Compounds of the invention may be isolated and purified by a variety of fractionation techniques, for example adsorption-elution, precipitation, fractional crystallisation, solvent extraction and liquid-liquid partition which may be combined in various ways.

Adsorption onto a solid support followed by elution has been found to be suitable for isolating and purifying compounds of the invention.

Compounds of the invention may be extracted from the cells and the aqueous phase with an appropriate organic solvent such as a ketone (e.g. acetone, methyl ethyl ketone or methyl isobutyl ketone), a halogenated hydrocarbon, an alcohol, a diol (e.g. propane-1,2-diol or butane-1,3-diol) or an ester (e.g. methyl acetate or ethyl acetate). Generally, more than one extraction may be desirable to achieve optimum recovery. The water-immiscible solvent extracts may themselves be extracted with basic aqueous solutions, and after acidification of these basic solutions the desired compounds may be reextracted into water-immiscible organic phase. Removal of the solvent from the organic extracts (e.g. by evaporation) yields a material containing the desired compounds.

Chromatography (including high performance liquid chromatography) may be effected on a suitable support such as silica; a non-functional macroreticular adsorption resin for example cross-linked styrene divinyl benzene polymer resins such as Amberlite XAD-2, XAD-4, XAD-16 or XAD-1180 resins (Rohm & Haas Ltd) or Kastell S112 (Montedison); a substituted styrene-divinyl benzene polymer, for example a halogenated (e.g. brominated) styrene-divinyl benzene polymer such as Diaion SP207 (Mitsubishi); an anion exchanger (e.g. IRA-35 or IRA-68) an organic solvent-compatible cross-linked dextran such as Sephadex LH20 (Pharmacia UK Ltd), or on reverse phase supports such as hydrocarbon linked silica e.g. $C_{18}$-linked silica. An alternative chromatographic means for the purification/separation of compounds of the invention is countercurrent chromatography using a coil extracter such as a multi-layer coil extracter.

Compounds of the invention may also be isolated and purified by the use of a liquid anion exchanger such as LA 2.

When IRA-68 or, particularly, IRA-35 is used as the solid adsorbant the cell extracts may be loaded directly without removal of solvent. The extract may either be loaded directly at about pH3 or at about pH8 following filtration of solid impurities.

Suitable solvents/eluants for the chromatographic purification/separation of compounds of the invention will, of course, depend on the nature of the column type and support. When using countercurrent chromatography we have found a solvent system comprising ethyl acetate, hexane, methanol and an aqueous acid (e.g. aqueous sulphuric acid) to be particularly suitable. When using an anion exchanger such as IRA-35 the resin may conveniently be washed with aqueous acetone followed by elution with sulphuric acid in aqueous acetone.

The presence of compounds of the invention during the extraction/isolation procedures may be monitored by conventional techniques such as h.p.l.c. or UV spectroscopy or by utilising the properties of the compounds.

Where a compound of the invention is obtained in the form of a solution in an organic solvent, for example after purification by chromatography, the solvent may be removed by conventional procedures, e.g. by evaporation, to yield the required compound. If desired, the compound may be further purified by the aforementioned chromatographic techniques.

Deacylation of compounds of the invention may be effected by acid or base catalysed hydrolysis. Suitable bases include hydroxides such as sodium hydroxide and potassium hydroxide and alkoxides (e.g. methoxides). The base catalysed hydrolysis may take place in water optionally in the presence of an organic cosolvent such as an ether (e.g. tetrahydrofuran) or an alcohol (e.g. methanol) at a temperature in the range of 0° to 100° C., preferably at elevated temperature. When an alkoxide is used as the base the reaction may conveniently be effected in an alcohol solvent (e.g. methanol) at a temperature in the range of 0° to 100° C. Suitable acids include mineral acids (e.g. hydrochloric acid) and organic acids (e.g. p-toluenesulphonic acid). The acid catalysed hydrolysis may be carried out in water optionally in the presence of an organic co-solvent such as an ether (e.g. dioxan or tetrahydrofuran) or a ketone (e.g. acetone) at a temperature in the range of 0° to 100° C., preferably at room temperature.

Compounds of the invention where $R_1$ represents a hydroxyl group may conveniently be prepared from the corresponding compounds where $R_1$ represents an acyloxy group as previously defined in formulae (I), (Ia) and (Ib). Thus, for example, when $R_1$ represents a substituted 2(E)-octenoyloxy group this may be converted to a hydroxyl group by treatment with a hydroxylamine (e.g. N-methylhydroxylamine) in the presence of a base (e.g. an organic base such as triethylamine) in a suitable organic solvent such as an amide (e.g. dimethylformamide) at a temperature ranging from, for example, 0° to 50° C., preferably 20° to 30° C.

Esterification of compounds of the invention to the corresponding methyl esters may conveniently be effected by treatment with a methylating agent such as a methyl halide (e.g. methyl iodide) or dimethyl sulphate in a suitable organic solvent such as an amide (e.g. dimethylacetamide or preferably dimethylformamide) in the presence of a base such as a bicarbonate (e.g. sodium bicarbonate). The reaction may conveniently be carried out at a temperature ranging from 0° to 100° C., preferably 20° to 30° C. Alternatively, the esterification may be effected by treatment with an ethereal solution of diazomethane in a suitable solvent such as methanol. The esterification may also be effected by treatment with methanol in the presence of a suitable acid such as a mineral acid (e.g. hydrochloric acid) at about room temperature. Conversion of one methyl ester of the invention to a different methyl ester of the invention may be carried out by appropriate esterification/deesterification steps. The deesterification may be effected under standard conditions, for example by base hydrolysis.

It is to be understood that the deacylation and esterification processes may be combined as sequential or simultaneous reaction steps as appropriate. Salts of compounds of the invention may be conveniently formed by treating a compound of the invention with an appropriate salt or base. Thus, for example, salts may conveniently be prepared by treating a compound of formula (I) with a salt or a base selected from sodium or potassium hydroxide, hydrogen carbonate, carbonate or acetate (e.g. potassium hydroxide, potassium hydrogen carbonate, sodium hydrogen carbonate or potassium acetate), ammonium acetate, calcium acetate and L-lysine as appropriate. The salt may, for example, be prepared by adding the appropriate salt or base (if necessary as an aqueous solution) to a solution or suspension of the compound of formula (I) in a suitable solvent such as water and/or a cosolvent such as an alcohol (e.g. methanol), a nitrile (e.g. acetonitrile) or a ketone (e.g. acetone) at temperatures of for example 0° C. to 80° C. and conveniently at about room temperature.

The dipotassium salt of Compound A may conveniently be prepared by adding aqueous potassium hydroxide, optionally in the presence of potassium acetate, to cell extract to adjust the pH to about 8. After filtering to remove solid impurities, the filtrate is subjected to adsorption-elution, for example, on IRA-35 followed by elution with acidic acetone and then by addition of a potassium solution (e.g. aqueous potassium hydroxide) to the eluate to adjust the pH to about 6. The crude dipotassium salt which precipitates may then be purified by adsorption-elution or liquid-liquid partition.

Salt formation may, if appropriate, be preceded by liberation of the compound of the invention from an aqueous-insoluble salt (e.g. a calcium salt) thereof by treating the aqueous-insoluble salt with a dilute aqueous mineral acid (e.g. hydrochloric or sulphuric acid), followed by batch adsorption onto reverse phase silica and elution with an appropriate organic solvent.

The isolated compounds of the invention and salts thereof may be further purified by filtering a solution (e.g. an acetone solution) of the compound under sterile conditions and recrystallising the compound from the filtrate.

D1, E1 and N1 each contain mixtures of two anomers in ratios of about 5:1, 2.5:1 and 1:1 respectively. Where spectroscopic data is available for the minor anomers this is provided in Tables 3 and 4 hereinafter enclosed in square brackets.

TABLE 2

| Compound | Approximate Molecular Weight | −FAB mass spectrometry [M − H]− | +FAB mass spectrometry [M + H]+ | +FAB mass spectrometry [M + Na]+ | Molecular Formula |
|---|---|---|---|---|---|
| A | 690 | 689.2789 | — | 713.2753 | $C_{35}H_{46}O_{14}$ |
| B | 648 | 647.2708 | — | 671 | $C_{33}H_{44}O_{13}$ |
| C | 538 | 537.1673 | — | 561 | $C_{25}H_{30}O_{13}$ |
| D | 704 | 703 | — | 727 | $C_{36}H_{48}O_{14}$ |
| E | 662 | 661 | — | 685 | $C_{34}H_{46}O_{13}$ |
| F | 496 | 495 | — | 519 | $C_{23}H_{28}O_{12}$ |
| G | 676 | 675.2679 | — | 699 | $C_{34}H_{44}O_{14}$ |
| H | 688 | 687.2653 | — | 711 | $C_{35}H_{44}O_{14}$ |
| I | 708 | 707.2943 | — | 731 | $C_{35}H_{48}O_{15}$ |
| J | 706 | 705 | — | — | $C_{35}H_{46}O_{15}$ |
| K | 706 | 705 | — | — | $C_{35}H_{46}O_{15}$ |
| L | 694 | 693 | — | — | $C_{34}H_{46}O_{15}$ |
| M | 666 | 665 | — | 689 | $C_{33}H_{46}O_{14}$ |
| N | 664 | 663 | 665 | — | $C_{33}H_{44}O_{14}$ |
| O | 674 | 673 | — | — | $C_{35}H_{46}O_{13}$ |
| P | 496 | 495 | 497 | — | $C_{23}H_{28}O_{12}$ |
| Q | 496 | 495 | — | — | $C_{23}H_{28}O_{12}$ |
| R | 480 | 479 | — | — | $C_{23}H_{28}O_{11}$ |
| S | 496 | 495 | 497 | — | $C_{23}H_{28}O_{12}$ |
| T | 689 | 688 | 690 | — | $C_{35}H_{47}NO_{13}$ |
| U | 692 | 691 | — | 715 | $C_{35}H_{48}O_{14}$ |
| V | 522 | 521 | — | 545 | $C_{25}H_{30}O_{12}$ |
| W | 652 | 651 | — | 675 | $C_{32}H_{44}O_{14}$ |
| X | 464 | 463 | — | — | $C_{23}H_{28}O_{10}$ |
| Y | 464 | 463 | — | — | $C_{23}H_{28}O_{10}$ |
| Z | 448 | 447 | 449 | 471 | — |
| A1 | 632 | 631 | 633 | — | $C_{33}H_{44}O_{12}$ |
| B1 | 689 | 688 | 690 | — | — |
| C1 | 664 | 663 | — | 687 | — |
| D1 | 462 | 461 | 463 | 485 | — |
| E1 | 464 | 463 | — | 487 | — |
| F1 | 478 | 477 | — | — | $C_{23}H_{26}O_{11}$ |
| G1 | 538 | 537 | — | — | — |
| H1 | 682 | 681 | 683 | — | — |
| I1 | 480 | 479 | — | — | — |
| J1 | 682 | 681 | 683 | — | — |
| K1 | 630 | 629 | 631 | — | — |
| L1 | 650 | 649 | — | — | — |
| M1 | 494 | 493 | 495 | — | $C_{23}H_{26}O_{12}$ |
| N1 | 464 | 463 | 465 | 487 | — |

TABLE 3

500 MHz proton nmr spectrum in deutero-methanol (unless otherwise stated) [δ values with
multiplicities, coupling constants (H) and integration values in parenthesis]

| Cpd | |
|---|---|
| A | (in deutero-chloroform 0.79 to 0.85(m, 9H), 1.00(d, 7, 3H), 1.04 to 1.15(m, 2H), 2.09(s, 3H), 2.40(m, 1H), 2.69(dd, 13, 5, 1H), 4.05(s, 1H), 4.94(s, 1H), 4.96(s, 1H), 5.06(d, 4, 1H), 5.30 (s, 1H), 5.78(d, 16, 1H), 5.92(s, 1H), 6.88(dd, 16, 8, 1H), 7.11(d, 7, 2H), 7.14(t, 7, 1H), 7.24(t, 7, 2H) |

TABLE 3-continued

| Cpd | 500 MHz proton nmr spectrum in deutero-methanol (unless otherwise stated) [δ values with multiplicities, coupling constants (H) and integration values in parentheses] |
|---|---|
| B | 0.80 to 0.90(m, 9H), 1.03(d, 7, 3H), 1.05 to 1.19(m, 2H), 2.28(m, 1H), 2.37(dd, 13, 9, 1H), 2.76 (dd, 13, 5, 1H), 3.92(d, 5, 1H), 4.08(d, 2, 1H), 5.00(s, 1H), 5.10(s, 1H), 5.27(s, 1H), 5.78(d, 16, 1H), 6.31(d, 2, 1H), 6.84(dd, 16, 8, 1H), 7.13(t, 7, 1H), 7.21(d, 7, 2H), 7.24(t, 7, 2H) |
| C | 0.85(d, 7, 3H), 2.06(m, 2H), 2.11(s, 3H), 2.25(m, 1H), 2.71(dd, 13, 6, 1H), 4.07(d, 2, 1H), 4.98(s, 1H), 5.03(s, 1H), 5.10(d, 5, 1H), 5.14(d, 2, 1H), 5.16(s, 1H), 7.15(t, 7, 1H), 7.19(d, 7, 2H), 7.26(t, 7, 2H) |
| D | 0.83 to 0.90(m, 9H), 1.03(d, 7, 3H), 1.08 to 1.20(m, 2H), 1.26 to 1.44(m, 3H), 1.96 to 2.08(m, 2H), 2.10(s, 3H), 2.23(m, 1H), 2.34(m, 1H), 2.39 to 2.50(m, 3H), 2.69(dd, 13, 6, 1H), 3.73(s, 3H), 4.04(d, 2, 1H), 4.97(s, 1H), 5.02(s, 1H), 5.08(d, 5, 1H), 5.32(s, 1H), 5.79(dd, 16, 1, 1H), 6.32(d, 2, 1H), 6.85(dd, 16, 8, 1H), 7.14(t, 7, 1H), 7.19(d, 7, 2H), 7.26(t, 7, 2H) |
| E | 0.80 to 0.89(m, 9H), 1.03(d, 7, 3H), 1.08 to 1.19(m, 2H), 1.27 to 1.43(m, 3H), 1.97 to 2.13(m, 3H), 2.28(m, 1H), 2.37(dd, 13, 9, 1H), 2.40 to 2.50(m, 2H), 2.76(dd, 13, 6, 1H), 3.73(s, 3H), 3.93(d, 5, 1H), 4.08(d, 2, 1H), 4.99(s, 1H), 5.10(s, 1H), 5.33(s, 1H), 5.78(dd, 16, 1, 1H), 6.31(d, 2, 1H), 6.85(dd, 16, 8, 1H), 7.13(t, 7, 1H), 7.20(d, 7, 2H), 7.25(t, 7, 2H) |
| F | 7.25(t, 7, 2H), 7.21(d, 7, 2H), 7.14(t, 7, 1H), 5.16(s, 1H), 5.14(d, 2, 1H), 5.11(s, 1H), 5.01(s, 1H), 4.09(d, 2, 1H), 3.94(d, 5.5, 1H), 2.78(ABX q, 13.5 and 6, 1H), 2.47(m, 1H), 2.36(ABX q, 13.5 and 9.5, 1H), 2.28(m, 1H), 2.16 to 1.98(m, 3H), 0.82(d, 7, 3H) |
| G | 0.86, (d, 7, 3H), 0.89(t, 7, 3H), 1.04(d, 7, 3H), 2.10(s, 3H), 2.24(m, 1H), 2.69(dd, 13, 6, 1H), 4.03(d, 2, 1H), 4.97(2, 1H), 5.02(s, 1H), 5.08(d, 5, 1H), 5.27(s, 1H), 5.78(dd, 16, 1, 1H), 6.31(d, 2, 1H), 6.89(dd, 16, 8, 1H), 7.14(t, 7, 1H), 7.19(d, 7, 2H), 7.26(t, 7, 2H) |
| H | 0.84 to 0.89(m, 6H), 0.99(d, 7, 3H), 1.80(d, 1, 3H), 2.10(s, 3H), 2.24(m, 1H), 2.33(m, 1H), 2.69(dd, 13, 6, 1H), 4.06(d, 2, 1H), 4.97(s, 1H), 5.03(s, 1H), 5.08(d, 5, 1H), 5.28(s, 1H), 5.73(d, 10, 1H), 5.80(d, 16, 1H), 6.33(d, 2, 1H), 7.13(t, 7, 1H), 7.19(d, 7, 2H), 7.25(t, 7, 2H), 7.34(d, 16, 1H) |
| I | 0.83 to 0.91(m, 12H), 0.96(m, 1H), 1.08(m, 1H), 1.61(m, 1H), 2.10(s, 3H), 2.24(m, 1H), 2.51 (dd, 16, 4, 1H), 2.71(dd, 13, 6, 1H), 3.93(m, 1H), 4.07(d, 2, 1H), 4.98(s, 1H), 5.02(s, 1H), 5.09(d, 5, 1H), 5.26(s, 1H), 6.24(d, 2, 1H), 7.16(t, 7, 1H), 7.19(d, 7, 2H), 7.26(t, 7, 2H) |
| J | 0.83–0.91(m, 9H), 1.16(m, 1H), 1,28(s, 3H), 1.52(m, 1H), 1.60(dd, 14, 4, 1H), 2.10(s, 3H), 2.24 (m, 1H), 2.32(m, 1H), 2.70(dd, 13, 6, 1H), 4.04(d, 2, 1H), 4.98(s, 1H), 5.02(s, 1H), 5.09(d, 5, 1H), 5.27(s, 1H), 5.99(d, 16, 1H), 6.31(d, 2, 1H), 7.03(d, 16, 1H), 7.15(t, 7, 1H), 7.19(d, 7, 2H), 7.26(t, 7, 2H) |
| K | 0.82–0.89(m, 6H), 0.93(d, 7, 3H), 1.14(m, 1H), 1.28(s, 3H), 1.48(m, 1H), 1.60(dd, 14, 4, 1H), 2.10(s, 3H), 2.24(m, 1H), 2.33(m, 1H), 2.69(dd, 13, 6, 1H), 4.04(d, 2, 1H), 4.97(s, 1H), 5.02(s, 1H), 5.08(d, 5, 1H), 5.27(s, 1H), 6.01(d, 16, 1H), 6.32(d, 2, 1H), 7.01(d, 16, 1H), 7.15(t, 7, 1H), 7.19(d, 7, 2H), 7.26(t, 7, 2H) |
| L | 0.83–0.92(m, 10H), 1.16(m, 1H), 2.10(s, 3H), 2.24(m, 1H), 2.51(dd, 15, 5, 1H), 2.71(dd, 13, 6, 1H), 3.96(m, 1H), 4.06(d, 2, 1H), 4.98(s, 1H), 5.02(s, 1H), 5.09(d, 5, 1H), 5.26(s, 1H), 6.26 (d, 2, 1H), 7.16(t, 7, 1H), 7.19(d, 7, 2H), 7.26(t, 7, 2H) |
| M | 0.81(d, 7, 3H), 0.84–0.91(m, 9H), 0.96(m, 1H), 1.08(m, 1H), 1.61(m, 1H), 2.28(m, 1H), 2.36(dd, 13, 9, 1H), 2.40(dd, 16, 9, 1H), 2.50(dd, 16, 4, 1H), 2.77(dd, 13, 6, 1H), 3.90–3.95(m, 2H), 4.10 (d, 2, 1H), 5.00(s, 1H), 5.11(s, 1H), 5.26(s, 1H), 6.24(d, 2, 1H), 7.13(t, 7, 1H), 7.21(d, 7, 2H), 7.25(t, 7, 2H) |
| N | 0.83–0.90(m, 6H), 1.03(d, 7, 3H), 1.09–1.19(m, 2H), 2.28(m, 1H), 2.64–2.75(m, 2H), 3.54(dd, 11, 4, 1H), 3.69(dd, 11, 5, 1H), 4.05(d, 2, 1H), 4.12(d, 6, 1H), 5.04(s, 1H), 5.15(s, 1H), 5.26(s, 1H), 5.78(dd, 16, 1, 1H), 6.30(d, 2, 1H), 6.85(dd, 16, 8, 1H) |
| O | 0.84–0.90(m, 9H), 1.02(d, 7, 3H), 1.09–1.19(m, 2H), 1.96(dd, 15, 2, 1H), 2.10(s, 3H), 2.67(dd, 13, 6, 1H), 2.85(dd, 15, 7, 1H), 4.87(s, 1H), 4.98(s, 1H), 5.03(s, 1H), 5.07(d, 5, 1H), 5.76 (dd, 16, 1, 1H), 6.45(dd, 2, 7, 1H), 6.82(dd, 16, 8, 1H), 7.13–7.19(m, 3H), 7.26(t, 7, 2H) |
| P | 1.39(d, 1, 3H), 1.88–2.00(m, 2H), 2.39(dd, 13, 9, 1H), 2.88(dd, 13, 6, 1H), 3.42–3.49(m, 2H), 4.07(d, 2, 1H), 5.05(m, 1H), 5.11–5.14(m, 2H), 7.12(t, 7, 1H), 7.15(d, 7, 2H), 7.22(t, 7, 2H) |
| Q | 1.00(d, 7, 3H), 1.98(m, 2H), 2.38(m, 2H), 2.51(dd, 13, 8, 1H), 2.59(dd, 13, 6, 1H), 2.75(m, 1H), 3.67(d, 12.5, 1H), 3.93(d, 12.5, 1H), 4.09(d, 2, 1H), 5.12(d, 2, 1H), 5.14(s, 1H), 5.20(d, 10, 1H), 7.11–7.16(m, 3H), 7.24(t, 7, 2H) |
| R | 0.96(d, 7, 3H), 1.42(d, 1, 3H), 1.88–2.00(m, 2H), 2.20(m, 1H), 2.29(m, 1H), 2.49(dd, 13, 8, 1H), 2.57(dd, 13, 6, 1H), 2.64(m, 1H), 4.08(d, 2, 1H), 5.06(m, 1H), 5.11(d, 2, 1H), 5.14(s, 1H), 7.10–7.15(m, 3H), 7.22(t, 7, 2H) |
| S | 1.16(d, 7, 3H), 1.19(s, 3H), 1.51(m, 1H), 1.65(m, 1H), 2.30(m, 1H), 2.52(dd, 16, 10, 1H), 2.83(dd, 16, 5, 1H), 3.62(d, 12, 1H), 3.97(d, 2, 1H), 5.10–5.13(m, 2H), 6.99(bd, 7, 1H), 7.03(dt, 1, 7, 1H), 7.13 (bt, 7.5, 1H), 7.34(bd, 8, 1H) |
| T | 0.84–0.89(m, 6H), 0.98(d, 7, 3H), 1.03(d, 7, 3H), 1.10–1.20(m, 2H), 1.81(m, 1H), 1.96(s, 3H), 2.18–2.30 (m, 2H), 2.46(m, 1H), 2.51(dd, 13, 8, 1H), 2.59(dd, 13, 6, 1H), 2.85(m, 1H), 3.67–3.75(m, 2H), 3.93 (d, 2, 1H), 5.18(d, 10, 1H), 5.24(s, 1H), 5.82(dd, 16, 1, 1H), 6.27(d, 2, 1H), 6.88(dd, 16, 8, 1H), 7.08 (tt, 7, 1, 1H), 7.16–7.24(m, 4H) |
| U | 0.84–0.90(m, 12H), 0.96(m, 1H), 1.09(m, 1H), 1.24(m, 1H), 1.55(m, 1H), 1.66(m, 1H), 2.10(s, 3H), 2.70 (dd, 13, 6, 1H), 4.03(d, 2, 1H), 4.98(s, 1H), 5.03(s, 1H), 5.08(d, 5, 1H), 5.26(s, 1H), 6.27(d, 2, 1H), 7.15(t, 7, 1H), 7.19(d, 7, 2H), 7.26(t, 7, 2H) |
| V | 0.86(d, 7, 3H), 1.93–2.08(m, 2H), 2.11(s, 3H), 2.24(m, 1H), 2.31(m, 1H), 2.51(dd, 14, 11, 1H), 2.70 (dd, 13, 6, 1H), 3.05(dd, 14, 3, 1H), 4.24(dd, 11, 3, 1H), 4.97(s, 1H), 5.02(s, 1H), 5.09(d, 5, 1H), 5.46 (s, 1H), 7.13–7.20(m, 3H), 7.26(t, 7, 2H) |
| W | 0.81(d, 7, 3H), 0.83–0.97(m, 7H), 1.40–1.52(m, 2H), 1.16(m, 1H), 2.28(m, 1H), 2.78(dd, 13, 6, 1H), 3.93 (d, 5, 1H), 3.96(m, 1H), 4.07(d, 2, 1H), 5.00(s, 1H), 5.10(s, 1H), 5.24(s, 1H), 6.26(d, 2, 1H), 7.13 (t, 7, 1H), 7.20(d, 7, 2H), 7.25(d, 7, 2H) |
| X | 0.96(d, 7, 3H), 1.42(d, 1, 3H), 1.85–1.97(m, 2H), 2.18(m, 1H), 2.26(m, 1H), 2.56(dd, 13, 6, 1H), 2.64(m, 1H), 3.03(dd, 14, 4, 1H), 4.28(dd, 11, 4, 1H), 5.05(m, 1H), 5.44(s, 1H), 7.10–7.15(m, 3H), 7.22(t, 7, 2H) |
| Y | 0.97(d, 7, 3H), 1.44(d, 1, 3H), 1.87(dd, 15, 2, 1H), 2.44–2.52(m, 2H), 2.61(dd, 13, 6, 1H), 2.67(m, 1H), 4.66(s, 1H), 5.05(m, 1H), 5.35(dd, 7, 2, 1H), 7.11–7.18(m, 3H), 7.23(t, 7, 2H) |
| Z | 0.96(d, 7, 3H), 1.44(d, 1, 3H), 1.87(m, 1H), 2.09–2.23(m, 2H), 2.47(dd, 13, 8, 1H), 2.59(dd, 13, 6, 1H), 2.66(m, 1H), 3.18(m, 1H), 5.04(m, 1H), 7.10–7.16(m, 3H), 7.23(t, 7, 2H) |
| A1 | 0.85–0.90(m, 6H), 0.95(d, 7, 3H), 1.04(d, 7, 3H), 1.41(d, 1, 3H), 1.90–2.00(m, 2H), 2.49(dd, 13, 8, 1H), 2.56(dd, 13, 6, 1H), 2.64(m, 1H), 4.10(d, 2, 1H), 5.06(m, 1H), 5.25(s, 1H), 5.79 (dd, 16, 1, 1H), 6.30(d, 2, 1H), 6.84(dd, 16, 8, 1H), 7.10–7.14(m, 3H), 7.22(t, 7, 2H) |
| B1 | 0.83(d, 7, 3H), 0.84–0.89(m, 6H), 1.03(d, 7, 3H), 1.09–1.20(m, 2H), 2.01(s, 3H), 2.15(m, 1H), 2.26(dd, 13, 9, 1H), 2.76(dd, 13, 5, 1H), 4.06(d, 2, 1H), 4.30(d, 7, 1H), 5.00(s, 1H), 5.01(s, 1H), 5.28(s, 1H), 5.79(dd, 16, 1, 1H), 6.32(d, 2, 1H), 6.85(dd, 16, 8, 1H), 7.13(t, 7, 1H), 7.19(d, 7, 2H), 7.25(t, 7, 2H) |
| C1 | 0.82(d, 7, 3H), 0.85(t, 7, 3H), 0.88(d, 7, 3H), 1.16(m, 1H), 1.28(s, 3H), 1.52(m, 1H), 1.60(dd, 14, 4, 1H), 2.36(dd, 13, 9, 1H), 2.77(dd, 13, 6, 1H), 3.93(d, 5, 1H), 4.07(d, 2, 1H), 4.99(s, 1H), 5.10(s, 1H), 5.28(s, 1H), 5.98(d, 16, 1H), 6.31(d, 2, 1H), 7.02(d, 16, 1H), 7.13(t, 7, 1H), 7.20(d, 7, 2H), 7.25(t, 7, 2H) |

TABLE 3-continued

| Cpd | 500 MHz proton nmr spectrum in deutero-methanol (unless otherwise stated) [δ values with multiplicities, coupling constants (H) and integration values in parenthesis] |
|---|---|
| D1 | 0.92–0.96(m, 3H), 1.34(d, 1, 3H), 2.08–2.23(m, 2H), 2.43–2.49(m, 1H), 2.64(d, 13, 1H), 2.82–2.96(m, 2H), 4.98–5.03(m, 1H), 5.76(s, 1H), 7.09–7.15(m, 3H), 7.19–7.23(m, 2H) [1.36(d, 1, 3H), 2.30(d, 14, 1H), 3.29(d, 14, 1H), 5.60(s, 1H)] |
| E1 | 0.93–0.96(m, 3H), 1.40(d, 1, 3H), 1.77(M, 1H), 1.96(m, 1H), 2.45(ABq, 2H), 2.59–2.69(m, 1H), 3.56(dd, 12, 4), 4.96–5.06(m, 1H) 5.73(s, 1H), 7.09–7.15(m, 3H), 7.19–7.23(m, 2H), [1.37(d, 1, 3H), 1.70(m, 1H), 1.92(m, 1H), 3.03(d, 14, 1H), 5.62(s, 1H)] |
| F1 | 0.94(d, 7, 3H), 1.35(d, 1, 3H), 2.18(m, 2H), 2.46(dd, 13, 8, 1H), 2.55(dd, 13, 6, 1H), 2.60(m, 1H), 2.80(m, 1H), 3.04(m, 1H), 4.57(s, 1H), 5.01(m, 1H), 5.71(s, 1H), 7.09–7.15(m, 3H), 7.22(t, 7, 2H) |
| G1 | 1.01(d, 7, 3H), 1.98(s, 3H), 2.50(dd, 13, 8, 1H), 2.62(dd, 13, 8, 1H), 2.76(m, 1H), 4.06(d, 2, 1H), 4.24(d, 12.5, 1H), 4.41(d, 12.5, 1H), 5.12–5.16(m, 2H), 5.33(d, 10, 1H), 7.11–7.16(m, 3H), 7.24(t, 7, 2H) |
| H1 | 0.97(d, 7, 3H), 1.03(d, 7, 3H), 2.55(dd, 13, 8, 1H), 2.75(dd, 13, 7.5, 1H), 3.48(d, 11, 1H), 3.52(d, 1, 1H), 3.65(d, 11, 1H), 3.94(d, 2, 1H), 5.82(dd, 16, 1, 1H), 6.85(dd, 16, 9, 1H), 7.10(tt, 7, 2, 1H), 7.18–7.26(m, 4H) |
| I1 | 0.95(d, 7, 3H), 1.37(d, 1, 3H), 4.03(d, 8, 1H), 4.70(d, 8, 1H), 5.00(m, 1H), 5.05(s, 1H), 7.09–7.15 (m, 3H), 7.21(t, 7, 2H) |
| J1 | 1.00(d, 7, 3H), 1.03(d, 7, 3H), 2.55(dd, 13, 7, 1H), 2.74(dd, 13, 8, 1H), 3.46(d, 2, 1H), 3.49(d, 11, 1H), 3.53(d, 11, 1H), 4.01(d, 2, 1H), 5.25(s, 1H), 5.81(dd, 16, 1, 1H), 6.28(d, 2, 1H), 6.85(dd, 16, 9, 1H) |
| K1 | 0.85–0.91(m, 6H), 0.93(d, 7, 3H), 1.04(d, 7, 3H), 1.11–1.21(m, 2H), 1.41(m, 2H), 1.57(m, 1H), 1.95 (m, 1H), 2.20(dd, 13, 9, 1H), 2.63(m, 1H), 2.82(dd, 13, 6, 1H), 3.93(d, 2, 1H), 4.09(d, 6, 1H), 4.91(s, 1H), 5.19(s, 2H), 5.78(dd, 16, 1, 1H), 6.58(d, 2H), 6.85(dd, 16, 8, 1H), 7.12(t, 7, 1H), 7.15(d, 7, 2H), 7.22(t, 7, 2H) |
| L1 | 1.54(m, 1H), 1.65(m, 1H), 2.78(dd, 13, 5), 3.93(d, 5, 1H), 4.06(d, 2, 1H), 5.00(s, 1H), 5.11(s, 1H), 5.27(s, 1H), 6.27(d, 2, 1H), 7.13(t, 7, 1H), 7.21(d, 7, 2H), 7.24(t, 7, 2H) |
| M1 | 1.13(d, 7, 1H), 1.54(m, 1H), 1.82(m, 1H), 2.71(dd, 13.5, 8, 1H), 2.78(dd, 13.5, 6.5, 1H), 3.27(m, 1H), 4.04(d, 2, 1H), 5.12–5.15(m, 2H), 6.46(d, 10, 1H), 9.31(s, 1H) |
| N1 | 0.91–0.96(m, 3H), 1.36(d, 1, 1.5H), 1.38(d, 1, 1.5H), 1.87(m, 0.5H), 2.37(dd, 13.7, 0.5H), 2.68(dd, 14, 5, 0.5H), 4.02(dd, 5, 1, 0.5H), 4.22(dd, 9, 7, 0.5H), 4.96–5.02(m, 1H), 5.22(s, 0.5H) 5.28(s, 0.5H), 7.09–7.15(m, 3H), 7.18–7.24(m, 2H) |

TABLE 4

| Cpd | Composite poise decoupled 125.75 MHz (or 100 MHz) carbon-13 nmr spectrum in deutero-methanol (unless otherwise stated) [δ values with the number of attached protons in parenthesis] |
|---|---|
| A | (in deutero chloroform) 171.5(0), 171.0(0), 169.1(0), 167.0(0), 166.7(0), 157.9(1), 145.4(0), 140.1(0), 128.9(1), 128.1(1), 125.8(1), 117.8(1), 111.4(2), 105.8(0), 88.5(0), 81.6(1), 80.7(1), 79.3(1), 75.1(1), 74.2(0), 42.9(2), 39.7(2), 36.7(1), 34.2(1), 33.6(2), 31.6(1), 29.4(2), 25.4(2), 20.9(3), 19.8(3), 18.8(3), 13.5(3), 10.9(3) |
| B | 172.4(0), 170.1(0), 168.4(0), 166.5(0), 157.6(1), 152.0(0), 142.5(0), 130.2(1), 129.2(1), 126.6(1), 119.8(1), 110.7(2), 107.1(0), 91.0(0), 82.3(1), 81.0(1), 78.6(1), 76.6(1), 75.6(0), 44.4(2), 41.2(2), 39.0(1), 35.6(1), 35.1(2), 33.1(1), 30.8(2), 26.0(2), 20.5(3), 19.2(3), 14.0(3), 11.4(3) |
| C | 172.9(0), 172.1(0), 170.4(0), 169.4(0), 148.0(0), 141.5(0), 130.1(1), 129.3(1), 126.9(1), 111.4(2), 106.6(0), 93.2(0), 84.1(1), 80.6(1), 79.3(1), 76.5(1), 75.7(0), 40.9(2), 37.6(1), 35.1(2), 26.3(2), 20.9(3), 14.1(3) |
| D | 172.4(0), 172.1(0), 168.9(0), 168.3(0), 166.5(0), 157.6(1), 147.7(0), 141.6(0), 130.2(1), 129.3(1), 126.9(1), 119.8(1), 111.6(2), 106.8(0), 91.0(0), 82.5(1), 81.0(1), 80.1(1), 77.0(1), 75.6(0), 52.5(3), 44.4(2), 40.9(2), 37.7(1), 35.5(1), 35.0(2), 33.1(1), 30.7(2), 26.5(2), 20.9(3), 20.5(3), 19.2(3), 14.2(3), 11.4(3) |
| E | 172.3(0), 168.9(0), 168.3(0), 166.5(0), 157.6(1), 152.0(0), 142.5(0), 130.2(1), 129.1(1), 126.6(1), 119.8(1), 110.7(2), 107.1(0), 91.0(0), 82.3(1), 81.0(1), 78.6(1), 77.0(1), 75.7(0), 52.5(3), 44.3(2), 41.2(2), 39.1(1), 35.5(1), 35.1(2), 33.1(1), 30.7(2), 26.0(2), 20.5(3), 19.2(3), 14.0(3), 11.4(3) |
| F | 173.0(0), 170.5(0), 169.5(0), 152.2(0), 142.4(0), 130.2(1), 129.1(1), 126.6(1), 110.4(2), 106.8(0), 93.2(0), 84.0(1), 79.3(1), 79.0(1), 76.5(1), 75.8(0), 41.3(2), 39.0(1), 35.3(2), 25.9(2), 13.9(3) |
| G | 172.8(0), 172.1(0), 170.4(0), 168.7(0), 166.7(0), 157.4(1), 147.8(0), 141.6(0), 130.2(1), 129.3(1), 126.9(1), 119.9(1), 111.5(2), 106.7(0), 91.2(0), 82.6(1), 81.2(1), 80.2(1), 76.6(1), 75.6(0), 40.9(2), 37.8(1), 37.7(1), 36.7(2), 35.0(2), 30.5(2), 26.4(2), 23.6(2), 20.9(3), 19.6(3), 14.2(3) 14.1(3) |
| H | 172.5(0), 172.1(0), 170.1(0), 168.6(0), 167.2(0), 152.3(1), 150.4(1), 147.8(0), 141.6(0), 133.0(0), 130.2(1), 129.3(1), 126.9(1), 115.6(1), 111.5(2), 106.9(0), 91.2(0), 82.5(1), 81.0(1), 80.2(1), 76.6(1), 75.6(0), 40.9(2) 37.7(1), 36.1(1), 35.0(2), 31.0(2), 26.4(2), 20.9(3) 20.4(3), 14.1(3), 12.4(3), 12.2(3) |
| I | 172.4(0), 172.10(0), 172.08(0), 170.0(0), 168.5(0), 147.8(0), 141.6(0), 130.2(1), 129.3(1), 126.9(1), 111.4(2), 106.9(0), 91.0(0), 82.4(1), 81.3(1), 80.4(1), 76.6(1), 75.5(0), 71.7(1), 41.4(2), 40.9(2), 40.7(2), 37.7(1), 36.7(1), 35.0(2), 32.6(1), 29.7(2), 26.3(2), 20.9(3), 20.2(3), 14.6(3), 14.1(3), 11.3(3) |
| J | (172.7(0), 172.1(0), 170.3(0), 168.6(0), 166.8(0), 158.3(1), 147.8(0), 141.6(0), 130.1(1), 129.3(1), 126.9(1), 118.0(1), 111.6(2). 106.7(0), 91.2(0), 82.7(1), 81.3(1), 80.3(1), 76.7(1), 75.6(0), 73.8(0), 40.9(2), 37.7(1), 35.1(2), 32.2(2), 31.3(1), 28.3(3), 26.5(2), 21.4(3), 20.9(3), 14.1(3), 11.5(3)) |
| K | (172.7(0), 172.1(0), 170.3(0), 168.6(0), 166.8(0), 158.4(1), 147.8(0), 141.6(0), 130.2(1), 129.3(1), 126.9(1), 118.0(1), 111.6(2), 106.8(0), 91.2(0), 82.6(1), 81.3(1), 80.3(1), 76.7(1), 75.6(0), 73.8(0), 40.9(2), 37.7(1), 35.1(2), 32.1(2), 31.3(1), 28.3(3), 26.5(2), 21.4(3), 20.9(3), 14.1(3), 11.5(3)) |
| L | 172.8(0), 172.1(0), 171.9(0), 170.4(0), 169.0(0), 147.9(0), 141.6(0), 130.2(1), 129.3(1), 126.9(1), 111.4(2), 106.7(0), 91.2(0), 82.6(1), 81.5(1), 80.5(1), 76.8(1), 75.7(0), 69.2(1), 43.3(2), 40.9(2), 37.6(1), 35.6(1), 35.5(2), 35.1(2), 33.3(2), 30.5(2), 26.3(2), 20.9(3), 19.4(3), 14.1(3), 11.6(3) |
| M | 172.5(0), 172.2(0), 170.2(0), 168.7(0), 152.1(0), 142.5(0), 130.2(1), 129.2(1), 126.6(1), 110.5(2), 107.0(0), 91.0(0), 82.3(1), 81.5(1), 78.9(1), 76.7(1), 75.6(0), 71.7(1), 41.4(2), 41.3(2), 40.7(2), 39.1(1), 36.7(1), 35.2(1), 32.6(1), 29.7(2), 25.9(2), 20.2(3), 14.7(3), 14.0(3), 11.4(3) |
| N | (172.4(0), 170.1(0), 168.4(0), 166.5(0), 157.5(1), 151.6(0), 142.0(0), 130.3(1), 129.2(1), 126.7(1), 119.8(1), 111.3(2), 107.0(0), 91.0(0), 82.4(1), 81.1(1), 77.0(1), 76.6(1), 75.6(0), 62.0(2), 46.0(1), 44.4(2), 35.6(1), 35.3(2), 35.0(2), 33.2(1), 30.8(2), 25.7(2), 20.5(3), 19.2(3), 11.4(3)) |
| O | 172.5(0), 172.0(0), 169.9(0), 168.5(0), 166.5(0), 157.4(1), 147.5(0), 141.6(0), 130.1(1), 129.3(1), 127.0(1), 119.9(1), 111.9(2), 109.1(0), 92.8(0), 79.7(1), 76.2(1), 75.3(0), 74.5(1), 44.3(2), 42.4(2), 40.9(2), 37.9(1), 36.1(2), 35.5(1), 33.1(1), 30.8(2), 27.2(2), 20.9(3), 20.5(3), 19.2(3), 14.2(3), 11.4(3) |
| P | 173.1(0), 170.6(0), 169.5(0), 141.9(0), 138.4(0), 130.4(1), 128.9(1), 126.6(1), 126.3(1), 106.8(0), 93.1(0), 83.8(1), 79.3(1), 76.5(1), 75.8(0), 66.5(2), 44.4(1), 39.2(2), 35.2(2), 33.7(2), 16.5(3) |
| Q | 172.9(0), 170.5(0), 169.4(0), 141.9(0), 138.6(0), 134.4(1), 130.3(1), 129.0(1), 126.7(1), 106.9(0), 93.1(0), 83.9(1), 79.3(1), 76.5(1), 75.7(0), 59.9(2), 45.0(2), 35.7(2), 35.6(1), 28.8(2), 21.5(3) |

TABLE 4-continued

| Cpd | Composite poise decoupled 125.75 MHz (or 100 MHz) carbon-13 nmr spectrum in deutero-methanol (unless otherwise stated) [δ values with the number of attached protons in parenthesis] |
|---|---|
| R | 172.9(0), 170.4(0), 169.4(0), 142.3(0), 135.1(0), 131.2(1), 130.3(1), 128.9(1), 126.5(1), 106.9(0), 93.1(0), 83.9(1), 79.3(1), 76.5(1), 75.8(0), 45.0(2), 35.9(1), 35.4(2), 33.5(2), 21.2(3), 16.2(3) |
| S | 173.1(0), 170.8(0), 169.7(0), 144.2(0), 137.1(0), 130.2(1), 128.3(1), 127.1(1), 126.4(1), 107.3(0), 93.1(0), 83.9(1), 76.5(1), 76.1(1), 75.7(0), 44.4(0), 39.7(2), 31.8(1), 31.4(2), 30.5(2), 27.1(3), 19.1(3) |
| T | 173.1(0), 172.4(0), 170.1(0), 168.4(0), 166.4(0), 157.5(1), 142.0(0), 135.6(0), 134.4(1), 130.5(1), 129.1(1), 126.5(1), 119.9(1), 106.9(0), 91.0(0), 82.5(1), 81.0(1), 76.5(1), 75.5(0), 45.5(2), 44.9(2), 44.4(2), 35.6(1), 35.5(1), 35.2(2), 33.1(1), 30.8(2), 22.7(2), 22.5(3), 21.3(3), 20.5(3), 19.2(3), 11.4(3) |
| U | 173.8(0), 172.4(0), 172.1(0), 170.1(0), 168.4(0), 147.8(0), 141.6(0), 130.2(1), 129.3(1), 126.9(1), 111.5(2), 106.8(0), 91.0(0), 82.3(1), 80.8(1), 80.3(1), 76.6(1), 75.6(0), 45.4(2), 40.9(2), 37.7(1), 34.9(2), 32.7(1), 32.58(2), 32.55(2), 30.8(1), 30.1(2), 26.4(2), 20.9(3), 20.1(3), 20.0(3), 14.1(3), 11.4(3) |
| V | 173.1(0), 172.1(0), 172.0(0), 170.9(0), 148.0(0), 141.6(0), 130.2(1), 129.3(1), 126.9(1), 111.2(2), 106.8(0), 87.9(0), 80.3(1), 76.3(1), 76.0(0), 73.8(1), 41.0(2), 39.7(2), 37.7(1), 34.8(2), 26.5(2), 20.9(3), 14.1(3) |
| X | 173.0(0), 171.9(0), 170.9(0), 142.3(0), 135.1(0), 131.3(1), 130.3(1), 128.9(1), 126.5(1), 107.1(0), 87.7(0), 76.2(1), 76.0(0), 73.3(1), 45.0(2), 39.7(2), 35.9(1), 35.0(2), 33.6(2), 21.2(3), 16.1(3) |
| Y | 173.2(0), 170.6(0), 169.7(0), 142.4(0), 134.9(0), 131.7(1), 130.2(1), 129.0(1), 126.7(1), 109.2(0), 95.0(0), 76.1(1), 75.5(0), 72.1(1), 45.0(2), 43.6(2), 36.6(2), 35.8(1), 34.6(2), 21.3(3), 16.0(3) |
| Z | 173.1(0), 172.1(0), 170.8(0), 142.3(0), 134.9(0), 131.7(1), 130.2(1), 128.9(1), 126.6(1), 109.8(0), 89.3(0), 76.0(0), 75.7(1), 45.0(2), 36.3(2), 35.8(1), 34.6(2), 32.0(2), 30.3(2), 21.3(3), 16.0(3) |
| A1 | 172.5(0), 170.2(0), 168.5(0), 166.5(0), 157.5(1), 142.3(0), 135.0(0), 131.4(1), 130.3(1), 128.9(1), 126.5(1), 119.9(1), 107.1(0), 91.0(0), 82.1(1), 81.1(1), 76.6(1), 75.6(0), 45.0(2), 44.4(2), 35.9(1), 35.5(1), 35.3(2), 33.5(2), 33.1(1), 30.8(2), 21.2(3), 20.(3), 19.2(3), 16.1(3), 11.5(3) |
| B1 | 172.7(0), 170.2(0), 169.9(0), 168.4(0), 166.5(0), 157.6(1), 149.3(0), 142.0(0), 130.2(1), 129.2(1), 126.8(1), 119.8(1), 111.9(2), 107.0(0), 91.1(0), 82.5(1), 81.0(1), 76.6(1), 75.6(0), 59.8(1), 44.4(2), 41.4(2), 37.7(1), 35.6(1), 35.1(2), 33.1(1), 30.8(2), 26.4(2), 22.5(3), 20.5(3), 19.2(3), 15.0(3), 11.4(3) |
| D1 | 206.4(0), 175.8(0), 169.4(0), 168.5(0), 142.2(0), 134.2(0), 131.7(1), 130.3(1), 128.9(1), 126.6(1), 106.4(0), 91.6(0), 85.4(0), 80.2(1), 44.9(2), 44.2(2), 36.0(1), 35.6(2), 34.0(2), 21.2(3), 16.1(3) |
| E1 | 176.1(0), 170.3(0), 168.7(0), 142.3(0), 134.8(0), 131.8(1), 130.2(1), 128.9(1), 126.6(1), 109.1(0), 91.0(0), 85.7(0), 80.4(1), 74.9(1), 45.0(2), 44.0(2), 36.8(2), 35.9(1), 29.9(2), 21.2(3), 16.2(3), [134.9(0), 131.6(1), 111.9(0), 86.2(0), 80.2(1), 75.2(1), 44.4(2), 37.0(2), 30.4(2)] |
| F1 | 205.9(0), 173.0(0), 169.1(0), 168.2(0), 142.2(0), 134.0(0), 131.7(1), 130.3(1), 128.9(1), 126.6(1), 102.0(0), 88.7(0), 82.9(0), 80.0(1), 79.5(1), 44.9(2), 36.0(1), 35.8(2), 34.0(2), 21.1(3), 16.2(3) |
| G1 | 137.2, 130.3, 129.0, 126.8, 63.0, 44.8, 35.8, 29.4, 20.8 |
| H1 | 166.8, 157.3, 142.6, 130.4, 129.1, 126.6, 120.1, 107.0, 82.7, 81.5, 77.0, 76.6, 65.9, 44.4, 43.5, 36.9, 35.6, 33.1, 30.8, 20.5, 19.1, 14.4, 11.4 |
| K1 | 172.8, 170.4, 166.2, 157.5, 151.0, 142.3, 130.2, 129.1, 126.6, 119.9, 119.0, 106.6, 89.4, 87.3, 78.0, 76.3, 44.4, 42.5, 40.7, 37.9, 35.6, 33.2, 30.8, 29.1, 20.5, 19.2, 15.7, 11.5 |
| N1 | 176.3(0), 176.1(0), 172.4(0), 171.8(0), 169.9(0), 169.5(0), 142.3(0), 135.5(0), 135.1(0), 131.2(1), 131.0(1), 130.2(1), 128.9(1), 126.5(1), 112.1(0), 106.5(0), 88.1(0), 85.2(0), 81.2(0), 81.0(0), 80.7(1), 80.4(1), 76.0(1), 73.6(1), 45.0(2), 38.5(2), 37.2(2), 36.0(2), 35.9(1), 34.8(2), 34.5(2), 34.4(2), 21.2(3), 16.2(3), 16.1(3) |

The following examples are provided by way of illustrating the invention and are not intended to limit the invention in any way.

EXAMPLE 1

Compounds A and B

IMI 332962 was grown on agar plates of the following composition:

| | |
|---|---|
| Malt extract (Oxoid L39) | 30 g |
| Mycological peptone (Oxoid L40) | 5 g |
| Yeast extract (Oxoid L21) | 0.5 g |
| Agar (Oxoid No 3) | 20 g |
| Distilled water to 1 liter | |

The pH of the medium before autoclaving was in the range of 5.3–5.5. The inoculated plates were incubated at 28° C. for 14 days. Several 6 mm diameter plugs of agar covered with fungal mycelium were cut from the growing edge of the culture and two plugs were transferred into each of several cryotubes containing 1.6 ml of sterile distilled water. The tubes were capped and stored at room temperature until required.

Two agar plugs were used to inoculate each of eight 50 ml aliquots of seed medium (A) contained in 250 ml Erlenmeyer flasks:

| Seed medium(A): | |
|---|---|
| Peptone (Oxoid L34) | 10 g |
| Malt extract (Oxoid L39) | 21 g |
| Glycerol | 40 g |
| Junlon 110 (Honeywill & Stein Ltd., Wallington, Surrey) | 1 g |
| Distilled water to 1 liter | |

The pH of the medium was adjusted to 6.3–6.5 with aqueous sodium hydroxide before autoclaving The flasks of inoculated seed medium were incubated at 25° C. on a shaker platform, which rotated at 250 rpm with a 50 mm diameter orbital motion, for 5 days.

The contents of the flasks were pooled and homogenised. The homogenised seed culture was used at 3% (v/v) to inoculate 120, 50 ml aliquots of fermentation medium (B) in 250 ml Erlenmeyer flasks:

| Fermentation medium(B): | |
|---|---|
| Glycerol | 50 g |
| Soyabean oil | 30 g |
| Cottonseed flour (Sigma) | 10 g |
| Distilled water to 1 liter | |

The pH of the medium before autoclaving was in the range 6.1–6.3. The flasks were incubated as above with shaking for 8 days.

(a) The fermentation broth (approximately 4L) from flasks incubated for 8 days was filtered to remove the mycelium and the filtrate adjusted to pH 2.8 with sulphuric acid (20% v/v) and extracted with ethyl acetate (x3). The ethyl acetate extracts were bulked and back extracted with 2×400ml of aqueous sodium hydrogen carbonate solution (1% w/v). The aqueous back extracts were bulked, adjusted to pH 2.8 as above and re-extracted into 2×800ml of ethyl acetate. These extracts were combined and evaporated to dryness to yield a brown oil. This oil was further processed by countercurrent chromatography using an Ito Multilayer Coil Extractor (P. C. Inc., Potomac, Md., USA). The coil used was the standard preparative coil consisting of approximately 70 meters of 2.6 mm internal diameter PTFE tubing giving a total volume of about 380 ml. The solvent system used was a mixture of ethyl acetate, hexane, methanol and N/100 sulphuric acid (6:5:5:6 by volume). The lower phase was kept stationary. The coil was filled with the lower phase using a Gilson Model 303 pump and a Model 804C Manometric Module (Gilson, Villiers Le Bel, France). The oil (497 mg in 4 ml of the upper phase +4 ml of the lower phase) was then injected at the "tail" end of the column. The centrifuge was then operated at 800 rev./min. and the mobile (upper) phase pumped at 4ml/min. from the "tail" end of the column. After 185 minutes the centrifuge was stopped and the column contents displaced by pumping methanol at 20 ml/min. 20 ml fractions were collected and monitored by measuring inhibition of squalene synthase.

Consecutive fractions showing activity against squalene synthase were bulked. The earlier fractions were evaporated to dryness to yield Compound A (90 mg) as a pale yellow oil.

The later fractions were pooled, evaporated to one quarter volume and extracted with ethyl acetate (2×2 volumes). The ethyl acetate extract was evaporated to dryness to give 40 mg of a yellow oil. This was combined with an additional 46 mg obtained by similar processing of another batch (5L) of fermentation broth produced as described in Example 3 below. The bulked material was further processed by countercurrent chromatography using as solvent a mixture of ethyl acetate, hexane, methanol and N/100 sulphuric acid (3:2:2:3 by volume) with the lower phase kept stationary. The instrument was operated and fractions were collected and monitored as described previously and the mobile (upper phase) was pumped at 5 ml/min. The biologically active fractions were bulked and evaporated to dryness to yield Compound B (33 mg) as a pale yellow oil; electron impact (EI) mass spectrometry gave the following fragment ions: M/Z 91, 170, 497 and also having the further characterising features presented in Tables 2–4.

(b) The mycelium separated from 6L broth, from flasks incubated for 8 days, was extracted with methanol (2×3L) and filtered. The filtrate was concentrated by evaporation to ca. 500 ml, adjusted to pH 3.0 with formic acid and extracted with 3×500 ml of ethyl acetate. The ethyl acetate extracts were bulked and back extracted with 2×200 ml of sodium hydrogen carbonate solution (1% w/v). The aqueous back extracts were bulked, adjusted to pH 3.0 and re-extracted into 2×500 ml of ethyl acetate. All the organic fractions were combined and reduced to dryness using a rotary evaporator to yield a brown oil. The oil (578 mg) was further processed by high performance liquid chromatography (HPLC) using a Gilson autopreparative system composed of 3 Gilson solvent delivery pumps (model 303), an 811 Dynamic mixer and an 802C manometric module. The chromatography was carried out on a Dynamax Microsorb C18 (5 μm) semi-preparative column (250×10 mm). The mobile phase was a gradient composed of acetonitrile and 0.1% v/v formic acid to pH 3.15 with ammonium acetate (1:3→4:1→1:3) pumped at 2.8–5.6 ml/min with a run time of 65 minutes. This method was repeated 16 times. 13×4.95 minute fractions were collected and monitored by measuring inhibition of squalene synthase. Fraction number 5 from each run was bulked, acidified to pH 3.0 with formic acid and extracted with 2×100 ml ethyl acetate. The organic phase was removed and evaporated to dryness to yield Compound A (172 mg) as a pale yellow oil.

EXAMPLE 2

90 ml of homogenised 3 day old seed culture prepared as in Example 1 was used to inoculate 3 liters of fermentation medium (B) in a 5 liter fermentation vessel. The inoculated medium was maintained at 25° C. and agitated with two 6-bladed turbine impellers (70 mm diameter) rotating at 800 rpm. The culture was aerated by sparging with sterile air at 3 Lpm. Excessive foaming of the culture was controlled by the addition of silicone antifoam (Dow Coming 1520) as necessary.

The culture was harvested after 6 days growth.

EXAMPLE 3

Eight 0.5 ml aliquots from a 5 day old fermentation carried out as in Example 1 were used to inoculate eight 50 ml aliquots of seed medium (A) contained in 250 ml Edenmeyer flasks. The flasks were incubated at 25° C. on a shaker platform, which rotated at 250 rpm with a 50 mm diameter orbital motion, for 4 days. The contents of the flasks were pooled and homogenised.

The homogenised seed culture was used at 3% (v/v) to inoculate 120, 50 ml aliquots of fermentation medium (B) in 250 ml Erlenmeyer flasks. The flasks were incubated with shaking as above for 10 days.

EXAMPLE 4

Compound A

Homogenised seed culture prepared as in Example 3 were used at 3% (v/v) to inoculate two fermentation vessels, each of 5 liters capacity, containing 3 liters of fermentation medium (B). The inoculated medium was maintained at 25° C. and agitated with two six bladed turbine impellers (70 mm diameter) rotating at 500 rpm. The culture was aerated by sparging with sterile air at 3 Lpm. Provision was made for control of excessive foaming of the culture by the addition of silicone antifoam (Dow Coming 1520). The contents of the two culture vessels were combined after 11 days growth and further processed by countercurrent chromatography according to the procedure in Example 1(a) above to give Compound A (137 mg); 500 MHz proton nmr in deutero-methanol includes signals at about δ 0.84–0.90 (m,9H), 1.03 (d,7,3H), 1.09–1.19 (m,2H), 2.10 (s,3H), 2.24 (m,1H), 2.34 (m,1H), 2.68 (dd,13,6,1H), 4.04 (d,2,1H), 4.97 (s,1H), 5.02 (s,1H), 5.08 (d,5,1H), 5.27 (s,1H), 5.80 (d,16,1H), 6.31 (d,2,1H), 6.85 (dd,16,8,1H), 7.14 (t,7,1H), 7.19 (d,7,2H), 7.26 (t,7,2H); composite pulse decoupled 125.75 MHz carbon-13 nmr in deuteromethanol includes peaks at about at about δ 172.5 (0), 172.1(0), 170.1(0), 168.5(0), 166.5 (0), 157.6(1), 147.7 (0), 141.6(0), 130.2(1), 129.3(1), 126.9(1), 119.8(1), 111.5 (2), 106.8 (0), 91.1 (0), 82.5 (1), 81.0 (1), 80.1 (1), 76.6 (1), 75.6 (0), 44.4 (2), 40.9 (2), 37.7 (1), 35.6 (1), 34.9

(2), 33.1 (1), 30.8 (2), 26.5 (2), 20.9 (3), 20.5 (3), 19.2 (3), 14.1 (3), 11.4 (3).

EXAMPLE 5

Frozen stocks of inoculum were prepared from a 5 day old fermentation carried out as in Example 1. Samples of culture were centrifuged for 10 min and the mycelium resuspended to the original volume in 15% glycerol and 0.01% Tween 80. The mycelium was spun down and resuspended again before being distributed in 1.8 ml amounts in plastic tubes and stored at $-20°$ C. Eight 0.5 ml aliquots of frozen inoculum were used to inoculate eight 50 ml aliquots of seed medium (A) contained in 250 ml Erlenmeyer flasks. The flasks were incubated at 25° C. on a shaker platform, which rotated at 250 rpm with a 50 mm diameter orbital motion, for 4 days. The contents of the seed flasks were pooled and used at 3% (v/v) to inoculate 120 50 ml aliquots of fermentation medium (B) in 250 ml Erlenmeyer flasks. The flasks were incubated with shaking as above for 9 days.

EXAMPLE 6

Compound C

The fermentation broth (5L) from Example 3 above was filtered to remove the mycelium and the filtrate adjusted to pH 2.8 with sulphuric acid and extracted with ethyl acetate. The ethyl acetate extract was back extracted with sodium hydrogen carbonate solution. The aqueous back extracts were bulked, adjusted to pH 2.8 as above and re-extracted with ethyl acetate. These extracts were combined and evaporated to dryness to yield an oil. This oil was further processed by countercurrent chromatography according to the method described in Example 1(a) above and using a solvent system comprising a mixture of ethyl acetate, hexane, methanol and N/100 sulphuric acid (6:5:5:6 by volume).

Consecutive fractions showing activity against squalene synthase but very low mobility in the countercurrent chromatography system (recovered only after completely displacing the stationary phase from the column) were bulked, evaporated to ¼ volume and extracted with 3×2 volumes of ethyl acetate.

This material was combined with two batches of similar material obtained by applying the above procedure to the fermentation broths from Examples 4 and 5 above. The combined material was further processed by countercurrent chromatography according to the method described in Example 1(a) above and using a solvent system comprising a mixture of ethyl acetate, hexane, methanol and N/100 sulphuric acid (6:1:1:6 by volume) with the lower phase kept stationary. The mobile phase was pumped at 4 ml/min and the biologically active fractions were bulked and evaporated to dryness to yield Compound C (95 mg) as a pale yellow oil having the physical characteristics presented in Tables 2–4.

EXAMPLE 7

Compound D

The methanolic extract (ca. 3 g) from mycelium separated from broth (6L) produced as described in Example 3 was bulked with that (ca. 5 g) obtained from broth (5L) produced as described in Example 5. The oil (8 g) was further purified by HPLC using a Gilson autopreparative instrument and operating conditions described in Example 1(b) for 18 cycles. Fraction number 7 was extracted with ethyl acetate after acidification to pH 3.0 with sulphuric acid and evaporated to a viscous oil. The oil (190 mg) was applied to the autopreparative HPLC system using as mobile phase a gradient consisting of acetonitrile and 5 mM aqueous sulphuric acid (2:3→4:1) pumped at 2.8 ml/min with a run time of 20 min. 16 Fractions were collected. Fraction 11 was extracted with ethyl acetate after acidification to pH 3.0 with sulphuric acid and the solvent was removed under reduced pressure to yield Compound D (ca. 6 mg).

EXAMPLE 8

Compound A

The contents of 4 final stage flasks grown as in Example 5 were pooled after 7 days incubation and homogenised to provide the seed for 120 50 ml aliquots of fermentation medium (B) which were incubated for 8 days as in Examples 3 and 5. The fermentation broth (approximately 6L) from flasks incubated for 8 days was filtered to remove the mycelium. The filtrate was adjusted to pH 2.8 with sulphuric acid (20% v/v) and extracted into ethyl acetate, back extracted into sodium hydrogen carbonate and re-extracted into ethyl acetate at pH 2.8 as described in Example 1(a). The ethyl acetate extract was concentrated under reduced pressure to a yellow oil which was dissolved in methanol (10 ml). This solution was evaporated to 3 ml and applied to a column (32×2.5 cm) of ODS-3 (Whatman Partisil Bioprep 40, 75 Angstrom, slurry packed in acetonitrile-water, 20:80). The column was eluted with a stepwise gradient of a mixture of acetonitrile and water, increasing the proportion of acetonitrile as follows: 1:4, 3:7, 2:3, 1:1, 3:2. Fractions were monitored by HPLC and those containing Compound A were evaporated to remove acetonitrile. The resulting aqueous suspensions were pooled and freeze dried overnight to yield Compound A (59 mg) as an off-white solid.

Compounds B, C and D may also be prepared as solids using similar freeze drying techniques.

The data presented in Tables 2–4 is consistent for Compound A as prepared in Examples 1, 4 and 8.

EXAMPLE 9

Compounds D and E

The product of Example 8 (4 g) was dissolved in methanol (500 ml) and concentrated hydrochloric acid (5 ml). The resulting solution was stood at room temperature for 22 h and was then diluted with methanol (500 ml) and stored at $-20°$ C. overnight. The solution was concentrated under reduced pressure at 30° C. to a volume of ca. 100 ml and diluted with acetonitrile:water (100 ml, 1:1 containing 2 ml concentrated sulphuric acid/liter). Analytical HPLC [Spherisorb ODS-2 column, flow rate 2 ml/min, acetonitrile:water (1:1, containing 150 μl concentrated sulphuric acid/liter)] showed two major components to be present which were isolated by preparative HPLC [2 inch Spherisorb ODS-2 column, flow rate 50 ml/min, acetonitrile:water (1:1, containing 2 ml concentrated sulphuric acid/liter)]. Fractions which contained the faster running component were combined and the acetonitrile was evaporated under reduced pressure at 30° C. The cloudy aqueous phase was extracted with dichloromethane (10×150 ml) and the organic extracts were combined, dried and evaporated to give Compound E (1.476 g) as a pale yellow foam; infra-red spectrum in bromoform includes peaks in cm$^{-1}$ at about 1752, 1709;

infra-red spectrum in Nujol includes peaks in cm$^{-1}$ at about 3459, 1748; $[\alpha]D+34.54°$ (c 0.00996 methanol) and also having the further characterising features presented in Tables 2-4.

Fractions which contained the slower running component were combined and the acetonitrile was evaporated under reduced pressure at 30° C. The aqueous phase was divided into four portions each of which was extracted with dichloromethane (8 ×250 ml). The organic extracts were combined, dried and evaporated under reduced pressure to give Compound D (1.601 g) as a pale yellow foam; infra-red spectrum in bromoform includes peaks in cm$^{-1}$ at about 1765, 1729, 1249; infrared spectrum in Nujol includes peaks in cm$^{-1}$ at about 3450, 1740; $[\alpha]D+36.02°$ (c 0.0103 methanol) and also having the further characterising features provided in Tables 2-4.

EXAMPLE 10

Compound F

The product of Example 8 (1.38 g) in methanol (25 ml) was treated with aqueous sodium hydroxide solution (0.8M; 20 ml) and the mixture was heated to reflux for 3h. The mixture was allowed to cool to 20°, and the precipitate was collected by filtration. The solid was dissolved in hydrochloric acid (2M: 40 ml) and extracted with ethyl acetate (4×45 ml). The organic solution was dried over MgSO$_4$ and evaporated to give 885 mg of a solid. The solid was purified by reverse-phase HPLC [1 inch Spherisorb C6 column, flow rate 15 ml/min eluting with 7.5% aqueous acetonitrile containing 0.15 ml concentrated sulphuric acid/liter increasing to 50% aqueous acetonitrile containing 0.15 ml concentrated sulphuric acid/liter. The appropriate fractions were combined and concentrated under reduced pressure. The concentrate was saturated with sodium sulphate and extracted with ethyl acetate (5×50 ml). The ethyl acetate extract was evaporated under reduced pressure, the residue was dissolved in water and freeze-dried to give Compound F (380 mg) as a white foam; infra-red spectrum in Nujol includes peaks in cm$^{-1}$ at about 3408, 1737; $[\alpha]D+4.50°$ (c 0.833 in methanol) and having the further characterising features presented in Tables 2-4.

EXAMPLE 11

Compound A, Calcium Salt

IMI 332962 was grown on agar plates of the following composition:

| | |
|---|---|
| Porridge Oats | 20 g |
| Trace Salts | 1 ml |
| [of a solution containing FeSO$_4$.7H$_2$O (0.1 g), MnCl$_2$.4H$_2$O (0.1 g) and ZnSO$_4$.7H$_2$O (0.1 g) in distilled water (100 ml)] | |
| Agar (Oxoid No. 3) | 18 g |
| Distilled water to 1 liter | |

The pH of the medium before autoclaving was in the range of 5.3–5.5. The inoculated plates were incubated at 28° C. for 14 days. Several 6 mm diameter plugs of agar covered with fungal mycelium were cut from the growing edge of the culture and two plugs were transferred into each of several cryotubes containing 1.6 ml of sterile distilled water. The tubes were capped and stored in liquid nitrogen until required.

| Medium (A): | |
|---|---|
| Peptone (Oxoid L34) | 10 g |
| Malt extract (Oxoid L39) | 21 g |
| Glycerol | 40 g |
| Junlon 110 (Honeywill & Stein Ltd., Wallington, Surrey) | 1 g |
| Distilled water to 1 liter | |

The pH of the medium was adjusted to about 6.5 with aqueous sodium hydroxide before autoclaving.

After 4 days incubation at 25° C. on a rotary shaker with a 5 cm throw at 250 rpm, the culture was passed through a 50 ml syringe to break up any large pellets. A 3% (v/v) transfer was then made into 250 ml Erlenmeyer flasks containing 50 ml of medium (B)

| Medium (B): | |
|---|---|
| Glycerol | 50 g |
| Soyabean oil | 30 g |
| Cottonseed flour | 10 g |
| Distilled water in 1 liter | |

The pH of the medium before autoclaving was in the range 6.2–6.3.

After 7 days incubation as above, the broth was centrifuged for 10 minutes and the supernatant discarded. The cell pellet was re-suspended in 15% (w/v) glycerol and 0.01% (v/v) Tween 80, centrifuged as before and the supernatant discarded. The cell pellet was again re-suspended in 15% (w/v) glycerol and 0.01% (v/v) Tween 80 and distributed into cryotubes and stored at <20° C.

Each of four 250 ml Erlenmeyer flasks containing 50 ml of medium (A) was inoculated with 0.5 ml of the vegetative preparation. The flasks were incubated at 25° C. on a rotary shaker with a 5 cm throw at 250 rpm for 4 days.

The contents of the flasks were pooled and used to inoculate 4 liters of medium (A) in a 7 liter fermenter. The inoculated medium was maintained at 25° C. and agitated with three six bladed turbine impellers rotating at 500 rpm for 48 hours. Provision was made for control of excess foaming of the culture by the addition of silicone antifoam (Dow Corning 1520). The culture was also aerated at a rate of 4 liters/minutes.

After 48 hours, 1.2 liters of culture broth was used to inoculate 40 liters of medium (A) in a 70 liter Biolafitte fermenter. The inoculated medium was maintained at 25° C. under a head pressure of 0.2 bar and agitated with three six bladed turbine impellers rotating at 500 rpm for 48 hours. Provision was made for control of excess foaming of the culture by the addition of silicone antifoam (Dow Corning 1520). The culture was also aerated at a rate of 40 liters/minutes.

After 48 hours, 15 liters of the culture broth was used to inoculate 500 liters of medium (B) in a 780 liter Biolafitte fermenter. The inoculated medium was maintained at 25° C. under a head pressure of 0.5 bar and agitated with three six bladed turbine impellers rotating at 200 rpm for 17 days. Provision was made for control of excess foaming of the culture by the addition of silicone antifoam (Down Corning 1520). The culture was also aerated at a rate of 500 liters/minute.

After 17 days harvest broth (ca. 400 liters) was removed from the fermenter with the aid of a water wash (ca. 40 liters) and the pH adjusted to 10.5 with 0.880 ammonia (7.5 liters). Dicalite (488L, 1%) was added to the broth which was stirred for 20 minutes and then filtered through Dicalite. The filtrate was adjusted to pH 6.8 with concentrated sulphuric acid. The cells were suspended in distilled water (450 liters) and the pH adjusted to 10.6 with 0.880 ammonia. The mixture was stirred for 30 minutes and filtered through Dicalite. The filtrate was adjusted to pH 7.0 with concentrated sulphuric acid and both filtrates were loaded onto a column of Amberlite XAD-16 resin (9" diameter, 40 liters) at 80 liters/hour. The column was then washed with ammonium sulphate solution (1% w/v, 80 liters/hour) until the effluent was clear, and then with water (40 liters). The column was eluted with acetone/water (1:1, 30 liters/hour), and after a forerun of 32 liters a fraction of 87 liters was collected. This fraction was treated with calcium acetate solution (200 g in 1.2 liters water) with stirring and, after 16 hours, the resulting precipitate was collected by filtration. The precipitate was washed with acetone/water (1:1, 2 liters), then with acetone (1 liter) and dried in vacuo over $P_2O_5$ to give the calcium salt of Compound A (153 g) as a solid.

EXAMPLE 12

Compound A, dipotassium salt

Method A

A solution of the product of Example 8 (70 mg) in methanol (1 ml) was treated with a solution of potassium acetate (20 mg) in water (0.25 ml). The mixture was diluted with aqueous methanol (1 ml) and water (0.25 ml) and the resulting precipitate was collected by filtration and dried in vacuo to give the title compound (55 mg) as a colourless solid, $\nu_{max}$ (Nujol) 3482 (OH), 1724 (C=O, ester), 1649 (C=C, olefin), and 1620 cm$^{-1}$ (C=O, carboxylate); Analysis Found: C,51.18; H,5.48; K,9.4; $H_2O$,5.4%. $C_{35}H_{44}K_2O_{14}$.2.5$H_2O$ requires: C,51.77; H,6.08; K,9.63; $H_2O$; 5.5%.

Method B

A solution of the product of Example 8 (70 mg) in methanol (1 ml) was treated with a solution of potassium bicarbonate (20 mg) in water (0.25 ml). The mixture was diluted with methanol (1 ml) and water (0.25 ml) and the resulting precipitate was collected by filtration and dried in vacuo to give the title compound (66 mg) as a colourless solid, m.p. 278°-280° C. (Kofler), $\nu_{max}$ (Nujol) 3481 (OH), 1724 (C=O, ester), 1649 (C=C, olefin) and 1620 cm$^{-1}$ (C=O, carboxylate);

Analysis Found: C,51.37; H,5.49; K,9.9; $H_2O$, 5.5%. $C_{35}H_{44}K_2O_{14}$.2.5$H_2O$ requires: C,51.77; H,6.08; K,9.6; $H_2O$, 5.5%.

Method C

A suspension of the product of Example 8 (300 mg) in water (30 ml) was treated with a solution of potassium bicarbonate (87 mg) in water (2 ml). A clear solution was obtained which was divided into two parts (16 ml each).

The first part was subjected to freeze drying to give the title compound (136mg) as a colourless foam, m.p. ca 280° C. (Kofler), $\nu_{max}$ (Nujol), 3485 (v. broad, OH), 1724 (ester C=O), 1649 (conjugated C=C), 1621 cm$^{-1}$ (carboxylate C=O);

Analysis Found: C,52.24, H,5.86; K,9.4%. $C_{35}H_{44}K_2O_{14}$.2$H_2O$ requires C,52.35; H,6.03; K,9.74%.

The second portion was diluted with methanol (100 ml) and the resulting gelatinous precipitate was collected by filtration and dried in vacuo to give the title compound (74 mg) as a cream coloured solid, m.p. 285° C. (Kofler), $\nu_{max}$ (Nujol) 3478 (broad, OH), 1724 (ester C=O), 1647 (conjugated C=C), 1622 cm$^{-1}$ (carboxylate C=O);

Analysis Found: C,52.13; H,5.86; K,9.5%. $C_{35}H_{44}K_2O_{14}$.2$H_2O$ requires: C,52.35; H,6.03; K,9.74%.

EXAMPLE 13

Compound A, tripotassium salt

Method A

A suspension of the product of Example 8 (1 g) in water (100 ml) was treated with a solution of potassium bicarbonate (430 mg) in water (10 ml). The resulting solution was subjected to freeze drying to give the title compound (1.08 g) as a beige coloured solid, $\nu_{max}$ (Nujol), 3491-3167 (broad, OH), 1731 (ester C=O), 1614 cm$^{-1}$ (carboxylate C=O and C=C);

Analysis Found: C,48.65; H,5.70; K,14.1; $H_2O$,6.2%. $C_{35}H_{43}K_3O_{14}$.3$H_2O$ requires: C,48.93; H,5.75; K, 13.65; $H_2O$,6.29%.

Method B

Compound A, tripotassium salt (200 mg) (prepared as in method A described above) was dissolved in warm water (ca 40° C.) (2 ml) and acetone (10 ml) was added. The resulting solution was stored in a refrigerator for 1 h and the precipitate was collected by filtration and dried in vacuo to give the title compound (183 mg) as a colourless granular solid, m.p. 276°-280° C., $[\alpha]+18.9°$ ($H_2O$,c1.045), $\nu_{max}$ D (Nujol), 1719 (ester, C=O), 1607 cm$^{-1}$ (carboxylate C=O and C=C);

Analysis Found: C,48.88; H,5.59; K, 13.8; $H_2O$,6.5%. $C_{35}H_{43}K_3O_{14}$.3$H_2O$ requires: C,48.93; H,5.75; K, 13.65; $H_2O$,6.29%.

Method C

A suspension of the product of Example 8 (1 g) in water (10 ml) was treated with potassium bicarbonate (430 mg) and stirred at 50° C. for 1 h. A further addition of water (20 ml) was made to obtain complete solution and the solution was then filtered. Acetone (180 ml) was added to the filtrate and the resulting solution was stood overnight in a refrigerator. The resulting precipitate was collected by filtration and dried in vacuo to give the title compound (660 mg) as a colourless solid, m.p. 265°-273° C. (Kofler), $\nu_{max}$ (Nujol), 3480 (v. broad, OH), 1719 (ester C=O) and 1607 cm$^{-1}$ (conjugated C=C and carboxylate C=O);

Analysis Found: C,48.45; H,5.85; K, 13.9%. $C_{35}H_{43}K_3O_{14}$.3$H_2O$ requires: C,48.93; H,5.73;K,13.65%.

Method D

The product of Example 11 (131 g) was added to a stirred mixture of acetonitrile/water (1:1,500 ml) containing sulphuric acid (16 ml). After 10 min, solids were removed by filtration, washed with the acetonitrile/water/sulphuric acid (300 ml, 49:49:2) and discarded. The combined filtrates (790 ml) were rendered homogenous by the addition of methanol (110 ml) and loaded onto a column (9.6×82 cm) of Whatman Partisil P40 ODS-3 packed in acetonitrile/water (1:1) containing sulphuric acid (2 ml/L). The column was developed in the same solvent system and after a forerun of 12L the developing solvent was changed to acetonitrile/water (6:4) containing sulphuric acid (2 ml/L) and fractions (50 ml) were collected. Fractions 26-102 were combined and stirred with fresh Whatman Partisil P40 ODS-3 (1.5L) and water (7L). After 20 min the adsorbent was removed by filtration washed with water until free of acid and then eluted with acetonitrile (2.5L).

Water was added, the acetonitrile removed by evaporation and the resulting suspension was freeze-dried to give a solid (31.6 g).

A portion of this solid (5 g) was dissolved in acetonitrile (200 ml) and water (200 ml) was added. The solution was warmed to 40° and titrated to pH9 with 0.77N aqueous potassium hydroxide. Potassium acetate (2.13g) in water (10 ml) was added and the solution was filtered, warmed and diluted with hot acetone to 2L. The solution was allowed to cool slowly and after 16 h the colourless crystalline solid was removed by filtration, washed with acetone (15 ml) and dried in vacuo. The solid (5.5 g) was powdered and allowed to equilibrate with the atmosphere to give the title compound;

Analysis Found: C,48.3; H,5.5, K,13.3; $H_2O$,6.9%. $C_{35}H_{43}K_3O_{14}.3.5$ $H_2O$ requires: C,48.43; H,5.81; K, 13.51; $H_2O$,7.3%.

Method E

In a similar purification as reported in method D, the combined fractions from a larger Whatman P40 chromatographic column was batch adsorbed onto fresh Whatman P40 which was filtered, washed and eluted with acetonitrile as above, but the acetonitrile solution (12.1L) was evaporated to 7L, filtered to remove debris and then the filtrate was adjusted to specific gravity 0.9 by addition of water. The concentration of Compound A in this solution was adjusted to 12.5 g/L by addition of acetonitrile/water (1:1). The solution was warmed to 45° and titrated to pH 9.2 with 0.912N aqueous potassium hydroxide solution. Potassium acetate (77 g) in water (200 ml) was added followed by acetone (4 volumes at 45°) whilst the solution was stirred. The solution was set aside to crystallise and the crystals were filtered on paper after 16 h washed with acetone (2L), dried in vacuo and sieved through a 20 mesh to give the title compound, $[\alpha]+18.9°$ ($H_2O$, cl.041);

D Analysis Found: C,48.5; H,5.5; K,13.45; $H_2O$,6.9%. $C_{35}H_{43}K_3O_{14}.3.5$ $H_2O$ requires: C,48.43; H,5.81; K, 13.51; $H_2O$,7.3%.

EXAMPLE 14

Compound A, diammonium salt

A solution of the product of Example 8 (1 g) in methanol (40 ml) was treated with a solution of ammonium acetate (246 mg) in water (5 ml). The resultant slurry was stirred for 30 min and was then filtered and dried in vacuo to give the title compound (690 mg) as a beige coloured solid, m.p. 193°–195° C. (Kofler), $v_{max}$ (Nujol), 3216 +($NH_3$), 1724 (ester C=O), 1651 (conjugated C=C), 1602 cm$^{-1}$ (carboxylate C=O);

Analysis Found: C,53.97; H,7.00; N,3.61; $H_2O$, 5.17%. $C_{35}H_{52}N_2O_{14}$. 3.25 $H_2O$ requires: C,53.66; H,7.53; N,3.58;$H_2O$,5.4%.

EXAMPLE 15

Compound A, tri-L-lysine salt

A suspension of the product of Example 8 (100 mg) in water (10 ml) was treated with L-lysine (63.5 mg) and the mixture was stirred at room temperature for 30 min. The resulting solution was subjected to freeze drying to give the title compound (157 mg) as a colourless freeze dried solid, $v_{max}$(Nujol), 1717 (ester C=O), 1602 cm$^{-1}$ (broad, carboxylate C=O, conjugated C=C,); $\delta(D_2O)$ includes 2.17(s,$OCOCH_3$), +2.61(d,J=6 Hz, $PhCH_2$), 3.01(t,J=6 Hz, 3×$NH_3CH_2CH_2-$), 3.75(t,J=5 Hz,3×$H_2NCHCO_2H$), 3.93(s,CH(OH)), 4.86–4.94(m,-$CHOCOCH_3$ and —O.CH-$CO_2$), 4.98 and 5.05(2s,C=$CH_2$), 5.90(d,J=13 HzO,COCH=CH), 6.17(s,CH-OCOCH=CH—), 6.94(rid,J=13 Hz,7 Hz,OCOCH=CH) and 7.18–7.39(m, aromatic).

EXAMPLE 16

Compound A, trisodium salt

A suspension of the product of Example 8 (1 g) in hot water (ca 40° C., 50 ml) was treated with an aqueous solution of sodium hydrogen carbonate (365 mg 20 ml). The resulting solution was stood at room temperature for 30 minutes and was freeze dried to give a cream coloured foam. This was dissolved in water (15 ml) and acetone (60 ml) was added and the resulting solution was stood at 3° C. for 48 h. The resulting crystalline solid was collected by filtration and dried in vacuo at 40° C. to give the title compound (555 mg) as a cream coloured solid, $[\alpha]+19.6°$ ($H_2O$,c1.109);

Analysis Found: C,51.28; H,5.76; D Na,8.5%. $C_{35}H_{43}Na_3O_{14}$. $3.5H_2O$ requires: C,51.28; H,6.15; Na,8.41%.

EXAMPLE 17

Compounds G, H and I

A portion of the product of Example 11 (70 g) was added to a stirred solution of acetonitrile/water (1:1, 1.2 liters) containing sulphuric acid (8 ml). A further portion of sulphuric acid (12 ml) was added and, after stirring for 30 minutes, the resulting suspension was sonicated and centrifuged for 30 minutes. The supernatant was decanted off and the precipitate remaining was washed with acetonitrile/water (1:1, 800 ml)containing sulphuric acid (1.6 ml). The precipitate was then removed by centrifugation and to the decanted combined supernatant was added a further portion (60 g) of the product of Example 11. The resulting suspension was stirred and sonicated after addition of sulphuric acid (18 ml) and then centrifuged. The supernatant (900 ml) was applied to a column of Whatman Partisil P40 ODS-3 (9.6×82 cm) packed in acetonitrile/water (1:1) containing sulphuric acid (2 ml/liter). The column was developed in the same system at 300 ml/hour and after a 8.33 liter forerun a fraction of 1.07 liters was collected. After reduction in volume to 500 ml by rotary evaporation, the majority of the UV absorbing material was adsorbed onto a Spherisorb 5 μm ODS-2 reverse phase liquid chromatography column (25 cm×21 mm). The column was washed with water and then desorbed with acetonitrile. The eluate volume was reduced to 20 ml and then treated with water (10 ml) and concentrated sulphuric acid (75 μl). This solution was subjected to preparative HPLC using a 5 μm Spherisorb ODS-2 (25 cm×21 mm) column with a mobile phase of acetonitrile/water (1:1) and concentrated sulphuric acid (2 ml/liter) and a flow rate of 18 ml/minute. 15 preparative runs injecting 2 ml of solution onto the column were performed with the system monitored by UV spectroscopy at 210 nm. Compounds G, H and I were isolated from fractions corresponding to UV peaks with retention times of 29, 32 and 18 minutes respectively as described hereinafter.

(a) Isolation of Compound I

Fraction corresponding to peaks with a retention time of 18 minutes were bulked, diluted with water and adsorbed onto a 5 μm Spherisorb ODS-2 column (25 cm×21 mm), washed with water and desorbed with acetonitrile. After rotary evaporation to remove the acetonitrile, the volume was adjusted to 30 ml with addition of water and the sample freeze dried to give a solid (112 mg). 100 mg of this solid was dissolved in acetonitrile/water (1:1, 4 ml) and concentrated sulphuric acid (2 ml/liter) and applied in 2 ml injections per run to a preparative HPLC column of 5 μm Spherisorb ODS-2 (25 cm×21 mm) using acetonitrile/water (1:1) and concentrated sulphuric acid (2 ml/liter) and developed in the same system at 25 ml/minute. The fraction corresponding to the peak (λ=210 nm) at a retention time of 20 minutes was retained in each run and the appropriate fractions were bulked, diluted with water, adsorbed onto a 5 μm Spherisorb ODS-2 column (25 cm×21 mm), washed with water and desorbed with acetonitrile. The acetonitrile was removed by rotary evaporation and water was added to the resultant mixture to give volume of 20 ml of suspension which was then freeze dried to give a solid (80 mg). 60 mg of this solid was dissolved in 2.5 ml of 30% acetonitrile/0.1M ammonium dihydrogen orthophosphate pH 6.5 and applied in 1.25 ml injections per run to a column of 5 μm Spherisorb ODS-2 (25 cm×21 mm) and developed in the same solvent at 25 ml/minute. Material eluting from the column between 26–35 min from each run was collected and pooled and, after dilution with water, was adsorbed onto a 5 μm Spherisorb ODS-2 column (25 cm×21 mm), washed with water and desorbed with acetonitrile. The acetonitrile was removed by rotary evaporation and water was added to the resultant mixture to give a volume of 30 ml of suspension which was then freeze dried to give a solid (46 mg). This solid was dissolved in acetonitrile/water (1:1, 5 ml) and concentrated sulphuric acid (2 ml/liter) and applied in 2.5 ml injections per run to a column of 5 μm Spherisorb ODS-2 (25 cm×21 mm) and developed in the same solvent at 25 ml/minutes. The fraction corresponding to the peak (λ=210 nm) at a retention time of 9.8 minutes was retained in each run and the appropriate fractions were bulked, diluted with water, adsorbed onto a 5 μm Spherisorb ODS-2 column (25 cm×21 mm), washed with water and desorbed with acetonitrile. The acetonitrile was removed by evaporation, water was added to give a volume of ca. 20 ml and the solution was freeze dried to give Compound I (24 mg) having characterising features presented in Tables 2–4.

(b) Isolation of Compound G

Fractions corresponding to peaks with a retention time of 29 minutes were bulked, diluted with water and adsorbed onto a 5 μm Spherisorb ODS-2 column (25 cm×21 mm), washed with water and desorbed with acetonitrile. After rotary evaporation to remove the acetonitrile, the volume was adjusted to ca. 30 ml with addition of water and the solution freeze dried to give a solid (10 mg). 8 mg of the solid was dissolved in acetonitrile/water (1:1, 1 ml) and concentrated sulphuric acid (2 ml/liter) and applied as a 1 ml injection (at a concentration of 8 mg/ml) to a preparative HPLC column of 5 μm Spherisorb ODS-2 (25 cm×21 mm) and developed in the, same solvent at 25 ml/minute. The fraction corresponding to the peak (λ=210 nm) at a retention time of 25 minutes was retained and diluted with water, adsorbed onto a 5 μm Spherisorb ODS-2 column (25 cm×21 mm), washed with water and desorbed in acetonitrile. The acetonitrile was removed by rotary evaporation and water was added to the resultant mixture to give a volume of ca. 20 ml which was freeze dried to give Compound G (5 mg) having the characterising features presented in Tables 2–4.

(c) Isolation of Compound H

Fractions corresponding to peaks with a retention time of 32 minutes were bulked, diluted with water and adsorbed onto a 5 μm Spherisorb ODS-2 column (25 cm×21 mm), washed with water and desorbed with acetonitrile. After rotary evaporation to remove the acetonitrile, water was added to the resultant mixture to give a volume of ca. 30 ml which was freeze dried to give Compound H (12 mg) having the characterising features presented in Tables 2–4.

EXAMPLE 18

Compounds J,K,L,M and N

The procedure in Example 17 was followed except that fractions were collected after a forerun of 8.89 liters instead of 8.33 liters from the Whatman Partisil P40 ODS-3 column. Two fractions were taken; the first fraction 1 a 1500 ml fraction followed by a second fraction 2 a 1220 ml fraction.

Fraction 1 (1500 ml) was stirred with 1 liter of Whatman Partisil P40 ODS-3. After dilution to 10 liters with water the suspension was stirred for 1 hour. The P40 material was removed by filtration using a Whatman No. 54 filter, washed with water and then desorbed with acetonitrile (1500 ml). After reduction in volume to 20 ml, 15 ml of acetonitrile was added to the filtered solution. This solution was subjected to preparative HPLC using a column of 5 μM Spherisorb ODS-2 (25 cm×21 mm), a mobile phase of acetonitrile/water (35:65) containing concentrated sulphuric acid (2 ml/liter), a flow rate of 25 ml/min and with the system monitored by UV spectroscopy at 210 nm. Ten preparative runs injecting 3.5 ml of solution into the column were performed. After a forerun of 690 ml, 2 fractions were collected; a 400 ml fraction X followed by a 420 ml fraction Y. The appropriate fractions from each preparative run were bulked to give 4.0 liters of fraction X and 4.2 liters of fraction Y.

(a) Isolation of Compound N

Fraction X (4.0 liters) was stirred with 200 ml of Whatman Partisil P40 ODS-3. Water was added to 10 liters and, after stirring for a further 1 hour, the P40 material was removed by filtration using a Whatman No. 54 filter. The P40 material was washed and desorbed with acetonitrile (200 ml). After evaporation of the acetonitrile solution to 1 ml, addition of 3 ml of acetonitrile/water (2:3)containing concentrated sulphuric acid (2 ml/liter) and centrifugation, the resulting solution was subjected to preparative HPLC using a column of 5 μM Spherisorb ODS-2 (25 cm× 21 mm), a mobile phase of acetonitrile/water (2:3) containing concentrated sulphuric acid (2 ml/liter), a flow rate of 25 ml/min and UV detection at 210 nm. The fraction corresponding to the peak with a retention time of 17.6 min was retained, diluted with water, adsorbed onto a column of 5 μM Spherisorb ODS-2 (25 cm×21 mm), washed with water and desorbed with acetonitrile. The acetonitrile was removed by evaporation and to the residue was added water to give 20 ml of a suspension which was freeze-dried to give a solid (20 mg). This solid (20 mg) was dissolved in 1 ml of acetonitrile/water (2:3) containing concentrated sulphuric acid 150 μl/liter and subjected to preparative HPLC using a column of 5 μM Spherisorb ODS-2 (25 cm×21 mm), a mobile phase of acetonitrile/water (2:3) containing concentrated sulphuric acid (150 μl/liter), a flow rate of 25 ml/min and UV detection at 210 nm. The fraction corresponding to the peak at a retention time of 13 min was retained, diluted twice with water, adsorbed onto a 5 µM Spherisorb ODS-2 column (25 cm x 21 mm), washed with water and desorbed with acetonitrile. After removal of the acetonitrile, water was added to give 20 ml of solution which was freeze-dried to provide Compound N (6 mg) having the characterising features presented in Tables 2–4.

(b) Isolation of Compound M

Fraction Y (4.2 liters) was stirred with 200 ml of Whatman Partisil P40 ODS-3. Water was added to 10 liters and, after stirring for a further 1 hour, the P40 material was removed by filtration using a Whatman No. 54 filter. The P40 material was washed and desorbed with acetonitrile (200 ml). After evaporation of the acetonitrile solution to 1 ml, addition of 3 ml of acetonitrile/water (2:3) containing concentrated sulphuric acid (2 ml/liter) and centrifugation, the resulting solution was subjected to preparative HPLC using a column of 5 µM Spherisorb ODS-2 (25 cm×21 mm), a mobile phase of acetonitrile/water (2:3) containing concentrated sulphuric acid (2 ml/liter), a flow rate of 25 ml/min and UV detection at 210 nm. The fraction corresponding to the peak with a retention time of 23.0 min was retained, diluted with water, adsorbed onto a 5 µM Spherisorb ODS-2 (25 cm×21 mm) column, washed with water and desorbed with acetonitrile. The acetonitrile was removed by evaporation and water was added to the residue to give 20 ml of a suspension which was then freeze-dried to give a solid (16 mg). The solid (16 mg) was dissolved in 1 ml of acetonitrile/water (2:3) containing concentrated sulphuric acid (150 µl/liter) and subjected to preparative HPLC using a column of 5 µM Spherisorb ODS-2 (25 cm×21 mm), a mobile phase of acetonitrile/water (2:3) containing concentrated sulphuric acid (150 µl/liter), a flow rate of 25 ml/min and UV detection at 210 nm. The fraction corresponding to the peak at a retention time of 16 min was retained, diluted twice with water, adsorbed onto a 5 µM Spherisorb ODS-2 column (25 cm×21 mm), washed with water and desorbed with acetonitrile. After removal of the acetonitrile, water was added to the residue to give 20 ml of a solution which was freeze-dried to provide Compound M (7.5 mg) having the characterising features presented in Tables 2–4.

Fraction 2 (1.22 liters) was evaporated to 700 ml and after addition of acetonitrile (80 ml) the clear solution was added to 500 ml of Whatman Partisil P40 ODS-3. The mixture was diluted with water to 10 liters and the resulting suspension stirred for 1 hour. The P40 material was removed by filtration using a Whatman No. 54 filter, washed with water and then desorbed with acetonitrile (1300 ml). After reduction in volume to 20 ml, 60 µl of concentrated sulphuric acid and acetonitrile (15 ml) were added and the solution filtered. This solution was subjected to preparative HPLC using a 5 µM Spherisorb ODS-2 (25 cm x 21 mm) column, a mobile phase of acetonitrile/water (2:3) containing concentrated sulphuric acid (2 ml/liter), a flow rate of 25 ml/min and UV detection at 210 nm. One preparative run injecting 1 ml of solution into the column and ten preparative runs injecting 3 ml of solution into the column were performed.

(c) Isolation of Compound J

Fractions corresponding to peaks with a retention time of 25 min were bulked, diluted twice with water and treated with concentrated sulphuric acid to a concentration of 2 ml/liter. The resulting solution was applied to a 5 µM Spherisorb ODS-2 (25 cm x 21 mm) column. The column was washed with water and eluted with acetonitrile. The acetonitrile was then removed by evaporation, the volume adjusted to 20 ml with water and the solution freeze-dried to give Compound J (23 mg) having the characterising features presented in Tables 2–4.

(d) Isolation of Compound K

Fractions corresponding to peaks with a retention time of 27.6 min were bulked and subjected to the procedure in pan (c) above to provide Compound K (27 mg) having the characterising features presented in Tables 2–4.

(e) Isolation of Compound L

Fractions corresponding to peaks with a retention time of 32.6 min were bulked and subjected to the procedure in pan (c) above to give a solid (12 mg) which was dissolved in 1.6 ml of acetonitrile/water (2:3) containing concentrated sulphuric acid (150 µl/liter) and tetrahydrofuran (distilled, 20 ml/liter) and subjected to preparative HPLC using a column of 5 µM Spherisorb ODS-2 (25 cm×21 mm), a mobile phase of acetonitrile/water (2:3) containing concentrated sulphuric acid (150 µl/liter) and tetrahydrofuran (distilled, 20 ml/liter) at a flow rate of 25 ml/min and UV detection at 210 nm. Two preparative runs injecting 0.8 ml of solution into the column were performed. The fractions corresponding to peaks at a retention time of 28 min were bulked and are referred to hereinafter as 'Bulked 28 min'.

Fractions corresponding to peaks at a retention time of 34 min were bulked and diluted twice with water. Concentrated sulphuric acid was added to a concentration of 2 ml/liter and the resulting solution applied to a 5 µM Spherisorb ODS-2 (25 cm×21 mm) column. The column was washed with water and eluted with acetonitrile. The acetonitrile was removed by evaporation, the volume adjusted to 20 ml with water and the solution freeze-dried to give a solid (12 mg). This solid was dissolved in 1 ml of acetonitrile/water (2:3) containing concentrated sulphuric acid (2 ml/liter) and subjected to preparative HPLC using a column of 5 µM Spherisorb ODS-2 (25 cm×21 mm), a mobile phase of acetonitrile/water (2:3) containing concentrated sulphuric acid (2 ml/liter), a flow rate of 25 ml/min and UV detection at 210 nm. The fraction corresponding to the peak at a retention time of 39 min was reduced in volume to 10 ml and acetonitrile (5 ml) was added. The solution was subjected to preparative HPLC using a 5 µM Spherisorb ODS-2 column, a mobile phase of acetonitrile/water (2:3) containing concentrated sulphuric acid (150 µl/liter) and tetrahydrofuran (distilled, 20 ml/liter), a flow rate of 25 ml/min and UV detection at 210 nm. The fraction corresponding to the peak at a retention time of 38.5 min was retained and bulked with 'Bulked 28 min'. The combined fractions were then diluted twice with water and concentrated sulphuric acid (200 µl) was added. The resulting solution was applied to a 5 µM Spherisorb ODS-2 (25 cm×21 mm) column. The column was washed with water and then eluted with acetonitrile. After removal of the acetonitrile by evaporation the volume was adjusted to 10 ml with water and the solution was freeze-dried to give Compound L (3 mg) having the characterising features presented in Tables 2–4.

EXAMPLE 19

Compound O

The product of Example 11 (750 g) was chromatographed on a Whatman P40 ODS-3 column (18 cm×90 cm) using acetonitrile/water (1:1) containing concentrated sulphuric acid (2 ml/liter) as solvent. After an initial volume of 100 liters of solvent a fraction of 6 liters was collected. The 6 liters were added to 500 g of Whatman P40 ODS-3 and the volume was adjusted to 20 liters with water. 28 ml of concentrated sulphuric acid was then added and the solution stirred for 1 hour. The P40 material was removed by filtration using a Whatman No. 54 filter and washed with water. The P40 material was then desorbed with acetonitrile (2 liters) and the volume reduced to 30 ml. Concentrated sulphuric acid (60 μl) was added, the solution filtered and then subjected to preparative HPLC using a 5 μM Spherisorb ODS-2 (25 cm×21 mm) column, a mobile phase of 52.5% acetonitrile/water containing concentrated sulphuric acid (2 ml/liter), a flow rate of 25 ml/min and UV detection at 210 nm. One preparative run injecting 6 ml of solution into the column, one preparative run injecting 3 ml of solution into the column and eight preparative runs injecting 2 ml of solution into the column were performed. Fractions corresponding to peaks with a retention time of 24.6 min were bulked, diluted twice with water and treated with concentrated sulphuric acid to give an overall concentration of acid of 2 ml/liter. The solution was then stirred with Whatman P40 ODS-3 (100 ml) for 1 hour. The P40 material was filtered off using a Whatman No. 54 filter and washed with water. After elution with acetonitrile, the acetonitrile was removed by evaporation and the volume adjusted to 20 ml with water. The solution was then freeze-dried to yield Compound O (177 mg) having the characterising features presented in Tables 2–4.

EXAMPLE 20

Compound B, tripotassium salt

The product of Example 11 (500 g) was added to acetonitrile:water (1:1; 1200 ml) containing sulphuric acid (75 ml) and stirred for 15 minutes. Solids were removed by filtration through a cellulose filter aid and washed with acetonitrile:water:sulphuric acid (500:500:2; 100 ml). The resulting solid was re-extracted with further fresh solvent mixture (1000 ml) and filtered as before. The combined filtrates were treated with methanol (500 ml) and loaded onto a column of Whatman Partisil Prep P40 (18×96 cm) packed in acetonitrile and equilibrated with acetonitrile:water:sulphuric acid (500:500:2; 60L). The column was eluted with the same solvent. After a forerun of approximately 40L, 2L fractions were collected. Fractions 2–6 were bulked and the pH adjusted to pH 6.8 with 0.880 ammonia for storage. These fractions were bulked with those from three similar columns and sulphuric acid at 4 ml/L (176 ml), fresh Whatman Partisil P40 silica (4 kg) and water (45L) were stirred in. After 1 hour the adsorbant was recovered by filtration, washed free of acid with distilled water and eluted with acetonitrile (6L). The eluate (6L) was concentrated by evaporation and filtered. The filtrate (2.85L) was diluted with distilled water (0.85L) and then with acetonitrile:water (1:1) to a total volume of 8L. The solution was warmed to 50° C., the pH adjusted to pH 9.1 with 1M potassium hydroxide solution (450 ml) and potassium acetate (38 g) in water (400 ml) was added. The solution was then diluted with hot (50° C.) acetone (32L). The solution was allowed to cool and the crystalline solid was recovered by filtration, washed with acetone (2L) and dried in vacuo to give the tripotassium salt of Compound B. The mother liquors from the crystallisation of the tripotassium salt of Compound B were retained and used in Example 22 hereinafter.

EXAMPLE 21

Compounds F,P,Q,R,S,U,V,W,X,Y,Z,B1,C1,D1,E1,F1,G1,H1,I1,J1,M1,N1 and P1

The product of Example 11 (550 g) was suspended in acetonitrile/water (1:1, 1.6L) and concentrated sulphuric acid (0.1L) added. This suspension was filtered and the filtrate made up to 2.5L with acetonitrile/water (1:1) containing 2 ml/L concentrated sulphuric acid. Methanol (0.5L) was also added to give an homogeneous solution which was loaded (8L/hr) onto a 22L Whatman P40 ODS-3 column equilibrated and eluted with acetonitrile/water (1:1) containing concentrated sulphuric acid (2 ml/L). Fractions of 10L, 35L, 20L, 10L, and 12L were collected and then the eluting solvent was changed to acetonitrile/water (6:4) containing 2 ml/L concentrated sulphuric acid. Further fractions of 11.25L and 6L were collected. The 35L fraction was stirred with Whatman P40 ODS-3 (1.5 kg), concentrated sulphuric acid (0.2L) and distilled water (35L) for 1 hour. The Whatman P40 ODS-3 was removed by filtration, washed with distilled water (10L) and components were eluted with acetonitrile (3L). The acetonitrile was evaporated to dryness and the residue was dissolved in distilled water (0.3L) and freeze dried. The freeze dried solid was dissolved in acetonitrile/water (4:6, 0.1L) containing concentrated sulphuric acid (2 ml/L), and loaded onto a 5.8L Whatman P40 ODS-3 column equilibrated and eluted with acetonitrile/water (4:6) containing concentrated sulphuric acid (2 ml/L). After a forerun (2.44L) eight fractions were taken: (1) 4.1L, (2) 1.86L, (3) 2.5L, (4) 3.35L, (5) 2.52L, (6) 2.64L, (7) 5.7L and (8) 8.24L.

(a) Isolation of Compound U

The 6 liter fraction was added to 500 g of Whatman P40 ODS-3 and the volume was adjusted to 20 liters with water. 28 ml of concentrated sulphuric acid was then added and the solution stirred for 1 hour. The P40 material was removed by filtration using a Whatman No. 54 filter and washed with water. The P40 material was then desorbed with acetonitrile (2 liters) and the volume reduced to 30 ml. Concentrated sulphuric acid (60 μl) was added, the solution filtered and then subjected to preparative HPLC using a 5 μM Spherisorb ODS-2 (25 cm×21 mm) column, a mobile phase of 52.5% acetonitrile/water containing concentrated sulphuric acid (2 m/liter), a flow rate of 25 ml/min and UV detection at 210 nm. One preparative run injecting 6 ml of solution into the column, one preparative run injecting 3 ml of solution into the column and eight preparative runs injecting 2 ml of solution into the column were performed.

A fraction was collected after each injection between 15.2–17 min. The fractions were combined, diluted to twice the volume with water and treated with concentrated sulphuric acid to give an overall concentration of acid of 2 ml/liter. The solution was then stirred with Whatman P40 ODS-3 (100 ml) for 1 hour. The P40 material was filtered off using a Whatman No. 54 filter and washed with water. After elution with acetonitrile, the acetonitrile was removed by evaporation and the volume adjusted to 20 ml with water. The solution was then freeze-dried to a black oil. The oil was dissolved in 4 ml of 52.5% acetonitrile/water containing 2 ml/L concentrated sulphuric acid and subjected to preparative HPLC using a column of 5 μM Spherisorb ODS-2 (25 cm×21 mm), a mobile phase of 52.5% acetonitrile/water containing 2 ml/L concentrated sulphuric acid, a flow rate of 25 ml/min and UV detection at 210 nm. The component eluting from the column between 17.0–18.6 min was collected, diluted to twice the volume with water and adsorbed onto a 5 μM Spherisorb ODS-2 (25 cm×21 mm) column. After washing with water, the column was eluted with acetonitrile. Removal of the acetonitrile by evaporation gave Compound U (10 mg) as a light yellow oil having the characterising features presented in Tables 2–4.

(b) Isolation of Compounds P, Q and S

Fraction (1) (4.1L) was stirred for 1 hour with Whatman P40 ODS-3 (1L) and distilled water (16L). The adsorbent was removed by filtration on Whatman 54 filter paper and the compounds were eluted from the P40 ODS-3 with acetonitrile (2L). The solution was evaporated to dryness. The brown residue was dissolved in acetonitrile/water (25:75, 25 ml) containing concentrated sulphuric acid (0.4 ml/L). A 2.5 ml portion was loaded onto a preparative HPLC column of 5 μm Spherisorb ODS-2 (25 cm×21 mm) and this was eluted with acetonitrile/water (25:75) containing concentrated sulphuric acid (0.4 ml/L) at 15 ml/min. Three components, detected at 210 nm, were collected. Component (i) eluted between 8.6 and 9.3 min, component (ii) eluted between 9.7 and 10.4 min, and component (iii) between 13.6 and 15.5 min. The preparative chromatography was repeated 9 times; fractions containing identical components were combined.

The solution which contained component (i) was diluted with distilled water to four times the original volume and pumped onto a water equilibrated 5 μM Spherisorb ODS-2 column (25 cm×21 mm) which was washed with water (0.2L) and eluted with acetonitrile (50 ml). The acetonitrile was removed by evaporation; the residue was dissolved in distilled water (10 ml) and freeze-dried to give Compound P (6.5 mg) having the characterising features presented in Tables 2–4. Components (ii) and (iii) were recovered the same way as component (i) to yield respectively Compound S (12.1 mg) and Compound Q (100 mg) having the characterising features presented in Tables 2–4.

(c) Isolation of Compounds R and V

Fraction (2) (1.86L) was stirred for 1 hour with Whatman P40 ODS-3 (1L) and distilled water (12L). The adsorbent was removed by filtration on Whatman 54 filter paper and adsorbed compounds were eluted with acetonitrile (1.5L). The acetonitrile extract was evaporated to dryness and the residue was dissolved in acetonitrile/water (25:75, 20 ml) containing concentrated sulphuric acid (0.4 ml/L). A portion (2 ml) was loaded onto a preparative HPLC column of 5 μM Spherisorb ODS-2 (25 cm×21 mm) which was eluted with acetonitrile/water (25:75) containing concentrated sulphuric acid (0.4 ml/L) at 20 ml/min and detection at 210 nm. 2 components were collected. Component (i) eluted between 20.8 and 25.2 min and component (ii) between 25.4 and 27.5 min. The preparative chromatography was repeated nine times and fractions containing identical components were combined.

The solution containing component (i) was diluted with distilled water to five times the original volume and pumped onto a water equilibrated 5 μm Spherisorb ODS-2 (25 cm×21 mm) column which was washed with distilled water (0.5L) and eluted with acetonitrile (50 ml). The acetonitrile was removed by evaporation and the residue dissolved in distilled water (25 ml) and freeze dried to yield Compound R (302 mg) having the characterising features presented in Tables 2–4.

Component (ii) was recovered in the same way as component (i) to yield Compound V (13.5 mg) having the characterising features presented in Tables 2–4.

(d) Isolation of Compounds X and Y

Fraction (3) (2.5L) was stirred for 1 hour with Whatman P40 ODS-3 (1.1L) and distilled water (14L). The adsorbent was removed by filtration on Whatman 54 filter paper and the adsorbed compounds were eluted with acetonitrile (2.5L). The acetonitrile extract was evaporated to dryness and the residue was dissolved in acetonitrile/water (30:70, 25 ml) containing concentrated sulphuric acid (0.15 ml/L). A portion (2.5 ml) was loaded onto a preparative HPLC column of 5 μm Spherisorb ODS-2 (25 cm×21 mm) and eluted with acetonitrile/water (35:65) containing concentrated sulphuric acid (0.4 ml/L). The column flow rate was 20 ml/min and components were detected at 210 nm. 2 components were collected. Component (i) eluted between 12.6 and 13.5 min and component (ii) eluted between 13.5 and 14.8 min. The preparative chromatography was repeated nine times and fractions containing identical components were combined.

The solution containing component (i) was diluted with distilled water to five times the original volume and pumped onto a water equilibrated 5 μm Spherisorb ODS-2 (25 cm×21 mm) column which was washed with water (0.5L) and eluted with acetonitrile (60 ml). The acetonitrile was removed by evaporation. The residue was dissolved in water (10 ml) and freeze-dried to yield Compound Y (9 mg) having the characterising features presented in Tables 2–4. Component (ii) was treated in the same manner as component (i) to yield Compound X (23.7 mg) having the characterising features presented in Tables 2–4.

(e) Isolation of Compound W

Fraction (5) (2.52L) was stirred for 1 hour in with Whatman P40 ODS-3 (1.0L) and distilled water (12L). The adsorbent was removed by filtration on Whatman 54 filter paper and the adsorbed components were eluted with acetonitrile (2L). The acetonitrile extract was evaporated to dryness and the residue was dissolved in acetonitrile/water (30:60,25 ml) containing concentrated sulphuric acid (0.4 ml/L). A portion (2.5 ml) was loaded onto a preparative HPLC column of 5 μm Spherisorb ODS-2 (25 cm×21 mm) and eluted with acetonitrile/water (35:65) containing concentrated sulphuric acid (0.4 ml/L). The column flow rate ws 20 ml/min and components were detected at 210 nm. A component eluting between 31 and 32.1 min was collected. The preparative HPLC was repeated nine times and fractions containing the component were bulked. The solution containing this component was diluted with distilled water to five times the original volume and pumped onto a water equilibrated 5 μm Spherisorb ODS-2 (25 cm×21 mm) column, which was washed with distilled water (0.5L) and eluted with acetonitrile (40 ml). The acetonitrile was removed by evaporation. The residue was dissolved in distilled water (10 ml) and freeze-dried to yield Compound W (1.5 mg) having the characterising features presented in Tables 2–4.

(f) Isolation of Compounds C1, F1, I1 and J1

Fraction (4) (3.35L) was stirred for 1.5 h with Whatman P40 ODS-3 (1.1L) and distilled water (10L). The adsorbent was removed by filtration on Whatman 54 filter paper. The compounds were eluted from the P40 ODS-3 with acetonitrile (2.5L). This was evaporated to dryness. The residue was dissolved in acetonitrile/water (8:22, 30 ml)containing concentrated sulphuric acid (0.15 ml/L). A 3 ml portion was loaded onto a preparative HPLC column of 5 μm Spherisorb ODS-2 (25 cm×21 mm) and this was eluted with acetonitrile/water (35:65) containing concentrated sulphuric acid (0.4 ml/L) at 20 ml/min. Four components, detected at 210 nm, were collected. Component (I) eluted between 13.1 and 13.8 mins, component(II) between 15.7 and 16.7 mins and component (III) between 30.9 and 32.9 mins and component (IV) between 23.6 and 25.5 mins. The preparative chromatography was repeated 9 times, fractions containing identical components were combined.

The solution containing component (I) was diluted with distilled water (x5) and pumped onto a clean, water equilibrated 5 μm Spherisorb ODS-2 column (25 cm ×21 mm) which was washed with water (0.5L) and eluted with acetonitrile (100 ml). The solution was evaporated to dryness and the residue was redissolved in water (10 ml) and freeze dried to give Compound I1 (3.5 mg) having characterising features presented in Tables 2–4.

Components (II), (III) and (IV) were recovered in the same way as component (I) to yield respectively Compound F1 (18.1 mg), Compound J1 (1.8 mg) and Compound C1 (11.3 mg) having the characterising features presented in Tables 2–4.

(g) Isolation of Compounds E1 and H1

Two further components, (II) and (III) were extracted from fraction 5 following the procedure in (e) above.

Component (II) eluted between 21 and 24.5 mins; component (III) eluted between 33 and 35 mins. The preparative HPLC was repeated nine times and fractions containing identical components were combined.

The solution which contained component CID was diluted with water (x5) and pumped onto a clean, water equilibrated 5 μm Spherisorb ODS-2 column (25 cm×21 mm) which was washed with water (0.5L) and eluted with acetonitrile (50 ml). The acetonitrile was removed by evaporation, the residue was dissolved in distilled water (10 ml) and freeze dried to give Compound E1 (75.9 mg) having the characterising features presented in Tables 2–4. Component (III) was recovered in the same way as component (II) to give Compound H1 (1.1 mg) having the characterising features presented in Tables 2–4.

(h) Isolation of Compounds D1 and Z Fraction (6) (2.64L) was stirred for 1 h with Whatman P40 ODS-3 (1L) and distilled water (10L). The adsorbent was removed by filtration on Whatman 54 filter paper. The compounds were eluted from the P40 ODS-3 with acetonitrile (2.5L) and this solution was evaporated to dryness. The residue was dissolved in acetonitrile/water (40:60, 25 ml) containing concentrated sulphuric acid (0.4 ml/L). A 2.5 ml portion was loaded onto a preparative HPLC column of 5 μm Spherisorb ODS-2 (25 cm×21 mm) and this was eluted with acetonitrile/water (40:60) containing concentrated sulphuric acid (0.4 ml/L), at 20 ml/min.

Two components, detected at 210 nm, were collected. Component (I) eluted between 11.7 and 13.5 mins, and component (II) eluted between 13.7 and 15.1 mins. The preparative chromatography was repeated 9 times, fractions containing identical components were combined.

The solution which contained component (I) was diluted with distilled water (x5) and pumped onto a clean, water equilibrated 5 μm Spherisorb ODS-2 column (25 cm×21 mm) which was washed with water (O:5L) and eluted with acetonitrile (150 ml). The acetonitrile was removed by rotary evaporation, the residue was dissolved in water (50 ml) and freeze dried to give Compound D1 (293 mg) having the characterising features presented in Tables 2–4. Component (II) was recovered in the same way as component (I) to give 12.1 mg Compound Z (12.1 mg) having the characterising features presented in Tables 2–4.

(i) Isolation of Compound G1

Following the procedure in (e) above a further component (III) eluted between 15 and 16.2 mins. The preparative chromatography was repeated nine times and identical fractions were combined.

The solution containing component (III) was diluted five times with distilled water and pumped onto a clean, water equilibrated 5 μm Spherisorb ODS-2 column, (25 cm×21 mm) which was washed with distilled water (0.5L) and eluted with acetonitrile (50 ml). The acetonitrile was removed by rotary evaporation and the residue redissolved in distilled water (25 ml) and freeze dried to give Compound G1 (1.8 mg) having the characterising features presented in Tables 2–4.

(j) Isolation of Compound M1

Following the procedure in (b) above a further component (IV) eluted between 15.6 and 16.8 mins. The preparative HPLC was repeated 9 times. Fractions containing identical components were combined.

The solution containing component (IV) was diluted with water (x4) and pumped onto a clean, water equilibrated 5 μm Spherisorb ODS-2 column (25 cm×21 mm) which was washed with water (0.2L) and eluted with acetonitrile (50 ml). The acetonitrile was rotary evaporated to dryness, the residue was dissolved in distilled water (10 ml) and freeze dried to give Compound M1 (9.1 mg) having the characterising features presented in Tables 2–4.

(k) Isolation of Compound B1

Fraction (8) (8.24L) was stirred with Whatman Partisil P40 ODS-3 reverse-phase silica (250 g) and water (9L) slowly added. After stirring for 30 min. the silica was recovered on a Buchner funnel and the filtrate discarded. The silica was washed with water until free of acid, then eluted with acetonitrile. The eluate was concentrated by evaporation to a volume of 100 ml.

The concentrate was subjected to preparative HPLC using a 5 μm Spherisorb ODS-2 (25 cm×21 mm) column with a mobile phase of acetonitrile/water (45:55) containing concentrated sulphuric acid (2 ml/L) at a flow-rate of 20 ml/min.

The concentrate was diluted with an equal volume of mobile phase and the solution filtered before injecting onto the column. Twenty preparative runs, injecting 1 ml of this solution per run, were performed and monitored by uv spectroscopy at 210 nm. From each run the fraction eluting at retention time 7.45–7.95 rain was collected. Pooled effluent fractions from the twenty runs were diluted with an equal volume of water and adsorbed onto a 5 μm Spherisorb ODS-2 (25 cm×21 mm) column. The column was washed with water and desorbed with acetonitrile to give an eluate (20 ml), which was shown by analytical hplc to contain two components.

The acetonitrile eluate was evaporated to an oily residue which was dissolved in acetonitrile/water (45:55) containing concentrated sulphuric acid (2 ml/L). This solution (16.5 ml) was subjected to preparative HPLC using a 5 μm Spherisorb C6 (25 cm×21 mm) column with a mobile phase of acetonitrile/water (45:55) containing concentrated sulphuric acid (2 ml/L), at a flow-rate of 20 ml/min. Eight preparative runs, injecting 1–2.5 ml/run, were performed with the system monitored by uv spectroscopy at 210 nm. The fraction eluting at retention time 16.1–16.8 min was collected. Pooled effluent fractions from the eight runs were diluted with an equal volume of water and absorbed onto the 5 μm Spherisorb C6 (25 cm×21 mm) column. The column was washed with water and desorbed with acetonitrile/water (90:10). Acetonitrile was removed by rotary evaporation and the aqueous residue freeze dried to give Compound B1 (8.7 mg) having the characterising features presented in Tables 2–4.

(l) Isolation of Compound F

Following the procedure in (b) above, a further component (IV) eluted between 10.5 and 12.4 mins.

The solution containing component (IV) was diluted with distilled water (X5) and pumped onto a clean, water equilibrated 5 μm Spherisorb ODS-2 column (25 cm ×21 mm) which was washed with water (0.5L) and eluted with acetonitrile (100 ml). The acetonitrile was removed by rotary evaporation, the residue was dissolved in distilled water (25 ml) and freeze-dried to give Compound F (149 mg) as a white solid, having the characterising features corresponding to those for Compound F prepared chemically according to the procedure in Example 10 above.

(m) Isolation of Compound N1

Following the procedure in (e) above a further component (II) eluting between 24.5 and 27 mins was collected. The preparative HPLC was repeated nine times and fractions containing this component were combined. The combined fractions were diluted with distilled water (x5) and pumped onto a clean, water equilibrated 5 μm Spherisorb ODS-2 (25 cm×21 mm) column which was washed with water (0.5L) and eluted with acetonitrile (50 ml). The acetonitrile was removed by rotary evaporation. The residue was redissolved in water (20 ml) and freeze-dried to yield Compound N1 (16.8 mg) as a brown solid had having the characterising features presented in Tables 2–4.

(n) Isolation of Compound P1

Fraction (7) (5.7L) was stirred with Whatman Partisil P40 ODS-3 reverse-phase silica (200 ml) and water (6L) slowly added. After stirring for 30 min the silica was recovered on a Buchner funnel and the filtrate discarded. The silica was washed with water until free of acid, then eluted with acetonitrile. The eluate was concentrated by rotary evaporation to a volume of 10 ml.

The concentrate from above was subjected to preparative HPLC using a 5 μm Spherisorb ODS-2 (25 cm×2 mm) column with a mobile phase of acetonitrile/water (40:60) containing concentrated sulphuric acid (2 ml/L) and tetrahydrofuran (20 m/L) at a flow-rate of 20 ml/min. The concentrate was diluted 1 in 10 with mobile phase and this solution filtered through a 0.45 μm membrane before injecting onto the column. Twenty preparative runs, injecting 4.5 ml of this solution per run, were performed and monitored by uv spectroscopy at 210 nm. From each run the fraction eluting at retention time 18.4–19.0 min was collected. Pooled effluent fractions from the twenty runs were diluted with an equal volume of water and adsorbed onto a 5 μm Spherisorb ODS-2 (25 cm×2.1 mm) column at 20 ml/min flow-rate. The column was washed with water and desorbed with acetonitrile/water (70:30). Acetonitrile was removed by rotary evaporation and the aqueous residue freeze-dried to give Compound P1 (3.0 mg).

EXAMPLE 22

Compound T

The mother liquors (25L) from Example 20 were treated in portions (5×5L) with Whatman Partisil P40 ODS-3 reverse-phase silica. To each portion was added the silica (100 g), water (15L) and concentrated sulphuric acid (20 ml) and the mixture stirred for 30 minutes. The silica was filtered and the filtrate discarded. The silica from all five portions was combined, washed with water until free of acid, and the adsorbed materials eluted with acetonitrile (2L). The eluate was concentrated by rotary evaporation to a volume of 90 ml.

The concentrate was subjected to preparative HPLC using a 5 μM Spherisorb ODS-2 (25 cm×21 mm) column with a mobile phase of acetonitrile-water (45:55) containing concentrated sulphuric acid (2 ml/L), at a flow-rate of 20 ml/minute. The concentrate was diluted with an equal volume of mobile phase before injecting onto the column. Eight preparative runs, injecting 2.5 ml/run, were performed with the system monitored by UV spectroscopy at 210 nm. From each run the fraction eluting at retention time 17.6 to 18.8 minutes was collected. Pooled effluent fractions from all the runs were diluted with an equal volume of water and adsorbed onto a 5 μm Spherisorb ODS-2 column (25 cm×21 mm). The column was washed with water and desorbed with acetonitrile. Water (10 ml) was added. Acetonitrile was removed by evaporation and the aqueous residue freeze-dried to give Compound T as a solid (10.5 mg) having the characterising features presented in Tables 2–4.

EXAMPLE 23

Compounds A1 and K1

Following the procedure in Example 19, the fraction eluting from the 5 μM Spherisorb ODS-2 column between 18.6 and 22.8 min was collected. Pooled fractions with this retention time from all the runs were diluted with an equal volume of water, and concentrated sulphuric acid added to give a total concentration of 2 ml/L. The solution was stirred with Whatman Partisil P40 ODS-3 (100 ml) for 1 h. The Partisil was filtered off using a Whatman No. 54 paper, washed with water, and eluted with acetonitrile. Acetonitrile was removed by rotary evaporation and water (20 ml) added. The solution was freeze dried to yield a solid (307 mg).

This solid was subjected to preparative HPLC using a 5 μm Spherisorb ODS-2 (25 cm×21 mm) column with a mobile phase of acetonitrile/water (45:55) containing concentrated sulphuric acid (2 ml/L) and tetrahydrofuran (40 ml/L), at a flow rate of 25 ml/min. The solid was dissolved in mobile phase at a concentration of 5 mg/ml for injection onto the column. Four preparative runs, injecting 4 ml/run, were performed with the system monitored by uv spectoscopy at 210 nm. From each run the fractions eluting at retention time 55.2–57.2 min (Fraction 1) and at 58.5–61.5 min (Fraction 2) were collected. The corresponding fractions from each preparative run were combined.

Fraction 2 (330 ml) was diluted with an equal volume of water and adsorbed onto a 5 μm Spherisorb ODS-2 (25 cm×21 mm) column. The column was washed with water and desorbed with acetonitrile/water (90:10). Acetonitrile was removed by rotary evaporation and the aqueous residue freeze-dried to give Compound A1 (11.3 mg) having the characterising features presented in Tables 2–4.

Fraction 1 (150 ml) was diluted with an equal volume of water and then adsorbed back onto the 5 μm Spherisorb ODS-2 (25 cm×21 mm) column at a flowrate of 20 ml/min. The column was then eluted with a mobile phase of acetonitrile/water (45:55) containing concentrated sulphuric acid (2 ml/L) and tetrahydrofuran (40 ml/L) at a flow-rate of 20 ml/min. After 60 min the mobile phase was changed to acetonitrile/water (50:50) containing concentrated sulphuric acid (2 ml/L) and tetrahydrofuran (40 ml/L), and the elution continued at 20 ml/min. The elution was monitored by uv spectroscopy at 210 nm, and the fraction eluting at retention time 69.8–73.8 min. collected. This fraction was diluted with an equal volume of water and adsorbed onto the 5 μm Spherisorb ODS-2 (25 cm×21 mm) column. The column was washed with water and desorbed with acetonitrile/water (90:10). Acetonitrile was removed by rotary evaporation and the aqueous residue freeze-dried to give Compound K1 (1.3 mg) having the characterising features presented in Tables 2–4.

EXAMPLE 24

Compound L1

Following the procedure in Example 17(a) above, the fraction eluting from the 5 μm Spherisorb ODS-2 (25 cm×21 mm) column (when using 30% acetonitrile/0.1M ammonium dihydrogen orthophosphate pH 6.5) between 21 and 24 min. (volume 525–600 ml) was retained. The bulk fraction from preparative liquid chromatography (150 ml) was diluted with water (x2), adsorbed onto a clean 5 μm Spherisorb ODS-2 (20 cm×21 mm) column, washed with water and eluted with acetonitrile. The acetonitrile was removed by evaporation and the volume adjusted to 30 ml with water. The suspension was freeze-dried to a solid (10.5 mg) which was dissolved in 30% acetonitrile/0.1M ammonium dihydrogen orthophosphate, pH 6.5 (2 ml) and subjected to preparative HPLC in the same solvent (25 ml/min) on Spherisorb S5 ODS-2 (20 cm×2.1 cm). Material eluting from the column between 19 and 25 min was collected, diluted with water (x2) and adsorbed onto a clean 5 μm Spherisorb ODS-2 (20 cm×21 mm) column, washed with water and eluted with acetonitrile. The acetonitrile was removed by evaporation and the volume adjusted to 30 ml with water. The resulting suspension was freeze-dried to give a solid (2.5 mg) which was dissolved in 5 ml of 50% acetonitrile/water and 2 ml/L concentrated sulphuric acid and subjected to preparative HPLC in two portions on 5 μm Spherisorb ODS-2 (20 cm×21 mm), in the same solvent at 25 ml/min. The substance eluting between 7.8 and 12 min was collected each time, bulked, diluted with water (x2), adsorbed onto a clean 5 μm Spherisorb ODS-2 (20 cm×21mm) column, washed with water and eluted with acetonitrile. The acetonitrile Was removed by evaporation, the volume adjusted to about 20 ml with water and the sample freeze-dried to give Compound L1 (ca. 1 mg) having the characterising features presented in Tables 2–4.

EXAMPLE 25

Compound A

The procedure in Example 5 was followed except that the pooled seed flasks were used at 3% (v/v) to inoculate 4 liters of seed medium (A) in a 7L fermenter. The culture was incubated with agitation as above at 500 rpm for 2 days with the culture aerated at 4L/min. 1.2L of the culture was removed and used to inoculate a 70L fermenter filled with 40L seed medium (A). The culture was incubated as above at 500 rpm for 2 days with the culture aerated at 40L/min. 15L of the culture was removed and added to a 780L fermenter filled with 500L fermentation medium (C).

| Fermentation medium (C): | |
|---|---|
| Fructose | 50 g |
| Soyabean oil | 30 g |
| Cottonseed flour (sigma) | 20 g |
| Natural pH | |

The culture was incubated with shaking as above at 200 rpm for 450 h with the culture aerated at 500L/min and fed at 120 h with a 50% (w/v) solution of fructose at 5 g/L/day increasing to 7.5 g/L/day at 162 h. Analysis of the broth at 450 h indicated a yield of Compound A of 1056 mg/L.

The above procedure was repeated on a reduced scale but replacing fructose with other sources of carbon selected from glucose, galactose, sucrose, maltose, lactose, myo-inositol, D-mannitol and soyabean oil. Analysis of the broth from each experiment at 450 h indicated a substantial titer of Compound A.

EXAMPLE 26

Compound A,tripotassium salt

Filter aid dicalite 488L (1% w/v) was added to whole broth (prepared according to the method of Example 25) and the broth adjusted to pH 2.5 using 75% w/w phosphoric acid. The cells were filtered and washed with water. The cells were stirred with 80% acetone - 20% water (12.0L) for 45 minutes at room temperature having been adjusted to pH 3.0 using 15% w/v sulphuric acid (188 ml). The slurry was filtered, and the cells reslurried in 80% acetone—20% water (12.0L) for 45 minutes at pH 3.0 (an additional 24.5 ml 15% sulphuric acid was required). The cells were washed with 80% acetone—20% water (9000 ml) after each filtration. Part of the filtrate (11.1L) was adjusted to pH 8.0 using 20% potassium hydroxide with stirring and the thin suspension filtered and the retained insoluble impurities washed with 80% acetone-water (150 ml), the washings being combined with the main filtrate. The filtrate was loaded to Amberlite IRA 35 - eluate cycle, 500 ml), at 1000 ml/hr, followed by a wash (65% acetone - 35% water, 100 ml) also at 1000 ml/hr. An eluant containing water (275 ml), acetone (650 ml) and 15% w/v sulphuric acid (81 ml) was prepared and passed to the column at 500 ml/hr. A forerun percolate (1410 ml) was collected until the appearance of a coloured band followed by rich eluate (1680 ml). A solid was precipitated from the eluate by adding, with stirring, 20% aqueous potassium hydroxide (59 ml) to adjust the pH from pH 1.9 to 6.0. The suspension was cooled 2 hours at 5° C. and filtered. The cake was washed with 65% acetone - 35% water (60 ml) followed by acetone (60 ml). The isolated solid was added to butyl acetate (580 ml) and water (980 ml) followed by 15% sulphuric acid with vigorous stirring to achieve pH 2.5. A small quantity of interfacial solid was removed by filtration and the separated aqueous layer discarded. The rich butyl acetate layer was stirred with distilled water (500 ml) while the pH was raised to 9.1 using 20% aqueous potassium hydroxide solution. The half-rich butyl acetate layer was washed with distilled water (100 ml) containing potassium acetate (5.1 g) previously adjusted to pH 9.2 and the separated aqueous layer combined with the previously separated aqueous layer (Extract 2). The tripotassium salt was crystallised by adding Extract 2 to acetone (6 volumes, 40° C.) with stirring. The solution was allowed to cooled with intermittent stirring to allow crystallisation to be well advanced before cooling at 5° C. for 2 hours with stirring. The slurry was filtered, washed with acetone (25 ml) and dried in vacuo at 30° C. to give the title compound.

EXAMPLE 27

[1S-[1α(4R*,5S*),3α,4β,5α,6α(2E,4R*,6R*),7β]]1-(4-Acetyloxy-5-methyl-3-methylene-6-phenylhexyl)-4,6,7-trihydroxy-2,8-dioxabicyclo[3.2.1]acid, 6-(4,6-dimethyl-2-octenoate), 3,4,5-trimethyl ester octane-3,4,5-tricarboxylic acid, 6-(4,6-dimethyl-2-octenoate),3,4,5-trimethyl ester A solution of Compound A (940 mg) in methanol (15 ml) was treated with a solution of diazomethane in diethyl ether (0.4M; 16 ml). The excess diazomethane was quenched with acetic acid (0.1 ml) and the solution was concentrated under reduced pressure. The residue was chromatographed on silica gel (Merck 7734, 50 g) eluting with dichloromethane increasing to 2% methanol/dichloromethane to give the title compound (906 mg); $[\alpha]_D^{23}+38.80°$ (c 0.962 in MeOH); $\nu_{max}$ (CHBr$_3$) 1760,1733 cm$^{-1}$ (esters); δ (CDCl$_3$) includes 0.8–0.9 (m,CH$_3$), 1.04 (d,J7 Hz,CH=CHCHCH$_3$), 2.09 (s,CH$_3$CO$_2$), 3.76,3.81 and 3.93 (3s,CO$_2$CH$_3$), 4.05 (d,J2 Hz,7-H), 4.98 and 5.00 (2s,C=CH$_2$), 5.10 (d,J6 Hz,CHOAc), 5.26 (s,3-H), 5.75 (d,J16 Hz,CH=CHCO$_2$), 5.81 (d,J2 Hz,6-H), 6.84 (dd,J$_1$16 Hz,J$_2$8.5 Hz,CH=CHCO$_2$), 7.13-7.28 (m,aromatic).

EXAMPLE 28

[1S-[1α(4R*,5S*),3α,4β,5α,6α(2E,4R*,6R*),7β]]1-(4-Hydroxy-5-methyl-3-methylene-6-phenylhexyl)-4,6,7-trihydroxy-2,8-dioxabicyclo[3.2.1]octane-3,4,5-tricarboxylic acid, 6-(4,6-dimethyl-2-octenoate), 3,4,5-trimethyl ester A solution of Example 27 (438 mg) in methanol (100 ml) containing concentrated hydrochloric acid (1 ml) was stirred for 68 h at 20° C. The pH of the solution was raised to 8 by adding sodium bicarbonate solution. The methanol was removed by evaporation under reduced pressure, the residue was diluted with water and extracted with ethyl acetate. The organic solution was washed with sodium bicarbonate, brine, dried (MgSO$_4$) and chromatographed on silica gel (Merck 7734, 50 g) eluting with ethyl acetate-cyclohexane (1:2) to give the title compound (248 mg); $[\alpha]_D^{23}+34.6$(c0.943 in MeOH); $\nu_{max}$ (CHBr$_3$) 3535 (alcohol), 1767, 1743, 1706 (esters), 1647 cm$^{-1}$ (C=C); δ (CDCl$_3$) includes 0.8–0.9 (m,CH$_3$), 1.04 (d,J7 Hz,CH=CHCHCH$_3$), 3.76,3.79 and 3.91 (3s,CO$_2$CH$_3$), 4.06 (broad singlet, 7H), 5.01 and 5.12 (2s,C=CH$_2$), 5.27 (s,3H), 5.73 (d,J16 Hz,CH=CHCO$_2$), 5.86 (d,J2 Hz,6-H), 6.82 (dd,J$_1$16 Hz,J$_2$8.5 Hz,CH=CHCO$_2$), 7.13-7.29 (m,aromatic).

EXAMPLE 29

[1S-[1α(4R*,5S*),3α,4β,5α,6α,7β]]1-(4-Acetyloxy-5-methyl-3-methylene-6-phenylhexyl)-4,6,7-trihydroxy-2,8-dioxabicyclo[3.2.1]octane-3,4,5-tricarboxylic acid, 3,4,5-trimethyl ester [Compound 1] and [1S-[1α(4R*,5S*),3α,4β,5α,6α, 7β]]1-(4-hydroxy-5-methyl-3-methylene-6-phenylhexyl)-4,6,7-trihydroxy-2,8-dioxabicyclo[3.2.1 ]octane-3.4.5-tricarboxylic acid, 3,4,5-trimethyl ester [Compound 2]

A solution of Example 27 (449 mg) was added to a solution of sodium methoxide in methanol (45 ml) [prepared from NaH (60% oil dispersion; 2.5 mg)] and the mixture was stood at 20° C. for 18 h. Hydrochloric acid (2M;2 ml) was added and the methanol was removed by evaporation under reduced pressure. The residue was diluted with ethyl acetate and washed with 2M hydrochloric acid, sodium bicarbonate, brine, dried and chromatographed on silica gel (Merck 7734, 50 g) eluting with 0 to 2% methanol-dichloromethane to give the title compound 1 (231 mg); $[\alpha]_D^{23}+7.4°$ (c 1.118 in MeOH); $\nu_{max}$ (CHBr$_3$) 3570, 3529 (alcohol), 1765, 1732cm$^{31}$ (esters); δ (CDCl$_3$) includes 0.86 (d,J7 Hz,CH$_3$), 2.11 (s,CH$_3$CO$_2$), 3.74, 3.79 and 3.91 (3s,CO$_2$CH$_3$), 4.15 (broad singlet, 7-H), 4.99 and 5.02 (2s,C=CH$_2$), 5.05 (d,J6 Hz,CHOAc), 5.11 (broad d, J5 Hz,6-H ), 5.17 (s,3-H), 7.11-7.32 (m,aromatic).

Further elution of the column with 5% methanol-dichloromethane gave the title compound 2 (39 mg); $[\alpha]_D^{23}+4.5$ (c. 0.5 in MeOH); δ (CDCl$_3$) include 0.86 (d,J7 Hz,CH$_3$), 3.73, 3.77 and 3.87 (3s,CO$_2$CH$_3$), 3.99 (d,J6 Hz,=CCHOH), 4.19 (broad singlet, 7-H), 5.05-5.09 (2s,3H,C=CH$_2$ and 6-H), 5.17 (s,3-H), 7.12-7.30 (m,aromatic).

EXAMPLE 30

[1S-[1α(4R*,5S*),3α,4β,5α,6α,7β]]1-(4-Hydroxy-5-methyl-3-methylene-6-phenylhexyl)-4,6,7-trihydroxy-2,8-dioxabicyclo[3.2.1]octane-3,4,5-tricarboxylic acid, 4-methyl ester, 3,5-disodium salt A solution of Example 29 Compound 2 (259 mg) in tetrahydrofuran (20 ml) was treated with aqueous sodium hydroxide solution (0.1M; 9.6 ml) and the mixture was stirred at 20° C. for 1.5 h. The tetrahydrofuran was removed by evaporation under reduced pressure, and the residue was freeze-dried to give the title compound (266 mg); $[\alpha]_D^{23}+0.6°$ (c 0.317 in MeOH); $\nu_{max}$ (nujol) 3420 (alcohol) 1717 (ester), 1616 cm$^{-1}$ (carboxylate); δ (CD$_3$OD) includes 0.81 (d,J7 Hz,CH$_3$), 2.32 (ABX,J$_1$13 Hz,J$_2$12 Hz,CH$_2$Ph) and 2.79 (ABX,J$_1$13 Hz,J$_2$5 Hz,CH$_2$Ph), 3.82 (s,CO$_2$CH$_3$), 3.93 (d,J6 Hz,=CCHOH), 4.08 (d,J2 Hz,7-H), 4.88 (s,3-H), 4.91 (d,J2 Hz,6-H), 5.04 and 5.10 (2s,C=CH$_2$), 7.13 (t,J7 Hz,4-proton of phenyl ring), 7.19 (d,J7 Hz,2-proton of phenyl ring), 7.24 (t,J7 Hz,3-proton of phenyl ring), δ ($^{13}$C) (CD$_3$OD) 174.6 (0), 174.0 (0), 173.1 (0), 152.2 (0), 142.5 (0), 130.2 (129.1 (1), 126.6 (1), 110.6 (2), 106.4 (0), 93.8 (0), 83.2 (1), 79.5 (1), 79.3 (1), 77.8 (1), 77.2 (0), 53.4 (3), 41.3 (2), 39.2 (1), 35.3 (2), 25.7 (2), 14.1 (3).

EXAMPLE 31

[1S-[1α(4R*,5S*),3α,4β,5α,6α,7β]]1-(4-Hydroxy-5-methyl-3-methylene-6-phenylhexyl)-4,6,7-trihydroxy-2,8-dioxabicyclo[3.2.1]octane-3,4,5-tricarboxylic acid, 4-methyl ester A solution of Example 27 (144.6 mg) in distilled tetrahydrofuran (2.5 ml) and aqueous sodium hydroxide solution (3N,3 ml) was stirred for 66 hrs at 0° C. then concentrated and acidified to pH6 with concentrated hydrochloric acid. Water (10 ml) was added and the mixture washed with ether (3×10 ml). The aqueous phase was acidified to pH1 with concentrated hydrochloric acid, extracted with ethyl acetate (20 ml) then saturated with ammonium sulphate and extracted with ethyl acetate (2×15 ml). The combined extracts were dried (MgSO$_4$) and evaporated to yield the title compound (100.6 mg) as a white gum; δ (CD$_3$OD) includes 0.81 (d,7 Hz,3H,CH$_3$), 3.81 (s,3H,CO$_2$CH$_3$), 3.93 (d,J5.5 Hz, 1H,CH(OH)), 4.09 (d,J2.5 Hz,1H,7-H), 5.12, 5.00 (2s,1H each, =CH$_2$), 5.04 (d,J2.5 Hz, 1H,6 -H), 5.12 (s,1H,3-H), 7.1–7.3 (m,5H,Ph).

EXAMPLE 32

[1S-[1α(4R*,5S*),3α,4β,5α,6α,7β]]1-(4-Hydroxy-5-methyl-3-methylene-6-phenylhexyl)-4,6,7-trihydroxy-2,8-dioxabicyclo[3.2.1]octane-3,4,5-tricarboxylic acid, 3,4 dimethyl ester A solution of Example 31 (98.4 mg) in methanol (15 ml) and concentrated hydrochloric acid (1.5 ml) was stirred for 48hrs then evaporated to a yellow liquid. Ethyl acetate (25 ml) and water (20 ml) were added. The aqueous phase was saturated with ammonium sulphate and extracted with ethyl acetate (2×25 ml). The combined organic phases were dried (MgSO$_4$) and evaporated to give the title compound (100 mg) as a dear foam; δ (CD$_3$OD) includes 0.81 (d,J6.3 Hz,3H,CH$_3$), 1.99–2.3 (m,5H,CH$_2$CH$_2$C=CHC(CH$_3$)), 2.3–2.8 (m,2H,CH$_2$Ph), 3.70,3.81 (2s, 3H each, 2×CO$_2$CH$_3$), 3.92 (d,J5.8 Hz,1H,CH(OH)), 4.09 (m,1H,7-H), 5.02 (s,1 H,6H), 4.99, 5.11 (2s,1H each,C=CH$_2$), 5.17 (s,1H,3-H), 7.1–7.3 (m,5H,Ph).

EXAMPLE 33

[1S-[1α(4R *,5S * ),3α,4β,5α,6α(2E,4R *,6R *),7β]]1-(4-Acetyloxy-5-methyl-3-methylene-6-phenylhexyl)-4,6,7-trihydroxy-2,8-dioxabicyclo[3.2.1]octane-3,4,5-tricarboxylic acid, 6-(4,6-dimethyl-2-octenoate), 3,4,5-trimethyl ester To a solution of Compound A (13.34 g) in dry dimethylformamide (200 ml) was added sodium hydrogen carbonate (22.7 g) followed by iodomethane (6.7 ml). After stirring for 55 hrs, water (440 ml) and ether (550 ml) were added. The phases were separated and the aqueous phase extracted with ether (220 ml). The combined organic phases were washed with saturated aqueous sodium hydrogen carbonate solution (4×200 ml), then dried (MgSO$_4$) and evaporated to give the title compound (13.82 g) as a white glassy solid; δ (CDCl$_3$) includes 0.81 (m,9H,3×CH$_3$), 1.04 (d,7.5 Hz,3H,CH$_3$), 1.0–1.5 (m,6H,CH(CH$_3$)CH$_2$CH(CH$_3$)CH$_2$CH$_3$), 2.05 (s,3H,CH$_3$CO), 3.76, 3.81, 3.93 (3s,3H each, 3×CO$_2$CH$_3$), 4.05 (m, 1H, 7-H), 4.98, 5.00 (2s,1H each,C=CH$_2$), 5.10 (d,J5 Hz, 1H,CH(OAc)), 5.26 (s,1H,3-H), 5.75 (d,J16.3 Hz,1H,CH=CHCO$_2$), 5.81 (d,J2.5 Hz,1H,6-H), 6.84 ( dd,J 16.3,8.75 Hz,1H,CH=CHCO$_2$), 7.1–7.3 (m,5H,Ph).

Analysis Found: C,62.13; H,7.16;
C$_{38}$H$_{52}$O$_{14}$ requires: C,62.28; H,7.15%.

EXAMPLE 34

[1S-[1α(4R*,5S*),3α,4β,5α,6α,7β]]1-(4-Acetyloxy-5-methyl-3-methylene-6-phenylhexyl)-4,6,7-trihydroxy-2,8-dioxabicyclo[3.2.1]octane-3,4,5-tricarboxylic acid, 3,4,5-trimethyl ester A solution of Example 33 (2.199 g) and N-methylhydroxylamine hydrochloride (501 mg) in dry N,N-dimethylformamide (15 ml) was treated with dry methylamine (1.25 ml) and the resulting suspension was stirred at room temperature. After 18.5 h the reaction mixture was diluted with water (150 ml) and extracted with ethyl acetate (3×75 ml). The combined extracts were washed with 1M-hydrochloric acid (75 ml), dried (MgSO$_4$) and evaporated to a gum. The gum was subjected to flash chromatography on silica gel developing and eluting with ethyl acetate. The appropriate fractions were combined and evaporated to give the title compound (924 mg) as a white foam; δ (DMSO-d$_6$) includes 0.79 (d,J6.25 Hz,3H,CH$_3$), 1.7–2.3 (m,5H,CH$_2$CH$_2$,CH(CH$_3$)), 2.10 (s,3H,CH$_3$CO), 2.3–2.7 (m,2H,CH$_2$Ph), 3.33, 3.60, 3.71 (3s,3H each,3-×CO$_2$CH$_3$), 3.89 (dd,J5 Hz, 1.2 Hz, 1H,7-H), 4.85 (dd,J6.3 Hz, 1.2 Hz, 1H,6-H), 4.95 (d,7.5 Hz, 1H,CH(CH$_3$CO)), 4.83, 4.99 (2s,2H,C=CH$_2$), 5.0 (s, 1H,3-H), 5.78 (s,1H,4-OH), 5.90 (d,J6.3 Hz, 1H,6-OH), 5.97 (d,J5 Hz, 1H,7-OH), 7.11–7.33 (m,5H,Ph).

EXAMPLE 35

[1S-[1α(4R*,5S*),3α,4β,5α,6α,7β]]1-(4-Acetyloxy-5-methyl-3-methylene-6-phenylhexyl)-4,6,7-trihydroxy-2,8-dioxabicyclo[3.2.1]octane-3,4,5-tricarboxylic acid, 4-methyl ester A solution of Example 34 (580 mg) in tetrahydrofuran (44 ml) was treated with aqueous 0.1M sodium hydroxide solution (22 ml). After 22.5 h the mixture was concentrated in vacuo to ca 10 ml, acidified with 2M-hydrochloric acid (5 ml), saturated with sodium chloride and extracted with ethyl acetate (3×20 ml). The combined extracts were dried and evaporated to give the title compound (560 mg) as a white foam; δ (CD$_3$OD) includes 0.84 (d,J6.3 Hz,3H,CH$_3$), 1.95–2.4 (m,5H,CH$_2$CH$_2$,CH(CH$_3$)), 2.10 (s,3H,CH$_3$CO), 2.4–2.78 (m,2H,CH$_2$Ph), 3.81 (s,3H,CO$_2$CH$_3$), 4.06 (d,J2.5 Hz,1H,7-H), 4.95–5.11 (m,4H,6-H,C=CH$_2$,CH(OAc)), 5.09 (s,1H,3-H), 7.1–7.3 (m,5H,Ph).

EXAMPLE 36

[1S-[1α(4R*,5S*),3α,4β,5α,6α,7β]]1-(4-Hydroxy-5-methyl-3-methylene-6-phenylhexyl)-4,6,7-trihydroxy-2,8-dioxabicyclo[3.2.1]octane-3,4,5-tricarboxylic acid, 3,4,5-trimethyl ester A solution of Example 34 (77 mg) in 10% hydrochloric acid in methanol (5ml) was stirred at room temperature. After 3 days the mixture was neutralised with solid sodium hydrogen carbonate, diluted with water (15 ml) and extracted with ethyl acetate (3×10 ml). The combined extracts were dried (MgSO$_4$) and evaporated to give the title compound (73 mg) as a white foam having proton NMR data similar to that described for Example 29 Compound 2.

EXAMPLE 37

[1S-[1α(4R *,5S* ),3α,4β,5α,6α(2E,4R *,6R *), 7β]]1-(4-Acetyloxy-5-methyl-3-methylene-6-phenylhexyl)-4,6,7-trihydroxy-2,8-dioxabicyclo[3.2.1]octane-3,4,5-tricarboxylic acid, 6-(4,6-dimethyl-2-octenoate), 4,5-dimethyl ester A solution of Example 27 (173 mg) in tetrahydrofuran (5 ml) at room temperature was treated with aqueous sodium hydroxide (0.1N, 2.36 ml). After 10 mins, most of the organic solvent was removed in vacuo. The resultant solution was diluted with water (20 ml) and washed with ether (2x). The aqueous solution was made acidic with 0.5M aqueous hydrochloric acid, extracted with ethyl acetate (3x), dried over magnesium sulphate and filtered. Removal of solvent gave the title compound as a light brown gum (145.2 mg); δ (CDCl₃) includes 7.1–7.3 (m,5H,Ph), 6.85 (dd, 1H,CH=CHCO₂,J=15.5 and 8.7 Hz), 5.81 (d,1H,CHOCOCH=CH,J=2 Hz), 5.75 (d,1H,CH=CHCO₂,J=15.5 Hz), 5.22 (s,1H,CHCO₂H), 5.08 (d,1H,AcOCH,J=5 Hz), 5.01 (s,2H,C=CH₂), 5.0 (broad s,1H,OH), 4.06 (d,1H,CHOH,J=2 Hz), 3.93 and 3.79 (2s,6H,2CO₂Me), 2.69 (dd,1H, one of PhCH,J=13.7 and 6.2 Hz), 2.1 (s,3H,CH₃CO₂), 1.05 (d,3H,CH=CHCHCH₃J=7 Hz), 0.8–0.9 (m,9H,3CH₃).

EXAMPLE 38

Methyl esters of Compound A

Sodium hydrogen carbonate (84 mg) was added to a solution of Compound A (691 mg) in N,N-dimethylformamide (5 ml). After stirring for 1 h at room temperature, methyl iodide (156 μl) was added and the mixture stirred for a further 24 h. The yellow solution was evaporated (40° /1 mmHg) to remove the majority of the N,N-dimethylformamide. The residue was diluted with ethyl acetate (75 ml) and washed with 1M hydrochloric acid (75 ml), water (4×75 ml) and brine (75 ml), and dried (Na₂SO₄). Evaporation of the solvent gave a yellow foam which was dissolved in acetonitrile : water (3:1, 15 ml) containing sulphuric acid (0.15 ml/L). The solution (10×1.5 ml) was loaded onto a preparative HPLC column (20 mm×250 mm) of Spherisorb ODS-2. The column was developed with acetonitrile : water (3:1) containing sulphuric acid (0.15 ml/L) at a flow rate of 15 ml/min. Appropriate fractions from each run were combined and the majority of the acetonitrile evaporated. The aqueous solutions were extracted with ethyl acetate (150 ml), washed with water (2×150 ml) and brine (150 ml) and dried (Na₂SO₄). The ethyl acetate was evaporated to give the products as white foams in order of elution:

i) RT 8.5 min, recovered starting material (163 mg).

ii) RT 10.2 min 4-methyl ester (132 mg); ¹H NMR (CD₃OD) includes δ 0.82–0.90 (9H,m,3×CH₃), 1.03 (3H,d,J9 Hz,CH₃), 2.11 (3H,s,OCOCH₃), 3.82 (3H,s,CO₂CH₃), 4.05 (1H,d,J2.5 Hz,7H), 4.97 and 5.03 (2H,2s, =CH₂), 5.08 (1H,d,J5 Hz,CHOAc), 5.21 (1H,s,3H), 5.80 (1H,d,J15 Hz,CH=CHCHMe), 6.28 (1H,d,J2.5 Hz,6H), 6.85 (1H,dd,J15 Hz,J9 Hz,CH=CHCHMe), 7.1–7.3 (5H,m,Ph); ¹³C NMR (CD₃OD) diagnostic values include δ 53.4 (CO₂CH₃), 166.6 (OCOCH=), 168.6 (5-CO₂H), 170.0 (3-CO₂H), 172.1 (OCOMe), 171.4 (4-CO₂Me).

Analysis Found: C,59.99; H,6.86; C₃₆H₄₈O₁₄.H₂O requires: C,59.82; H,6.97%.

iii) RT 12.7 min, 5-methyl ester (131 mg); ¹H NMR (CD₃OD) includes δ 0.82–0.90 (9H,m,3×CH₃), 1.03 (3H,d,J9 Hz,CH₃), 2.10 (3H,s,OCOCH₃), 3.68 (3H,s,CO₂CH₃), 4.03 (1H,d,J2.5 Hz,7H), 4.97 and 5.03 (2H,2s, =CH₂), 5.08 (1H,d,J5 Hz,CHOAc), 5.29 (1H,s,3H), 5.78 (1H,d,J15 Hz,CH=CHCHMe), 6.32 (1H,d,J2.5 Hz,6H), 6.78 (1H,dd,J15 Hz,J9 Hz,CH=CHCHMe), 7.10–7.30 (5H,m,Ph); ¹³C NMR (CD₃OD) diagnostic values include δ 52.5 (CO₂CH₃), 166.2 (OCOCH=), 167.4 (5-CO₂Me), 170.1 (3-CO₂H), 172.0 (OCOMe), 172.5 (4-CO₂H).

Analysis Found: C,60.20; H,6.86; C₃₆H₄₈O₁₄.0.75H₂O requires: C,60.20; H,6.95%.

iv) RT 14.1 min, 3,4-dimethyl ester (18 mg); ¹H NMR (CD₃OD) includes δ 0.82–0.90 (9H,m,3×CH₃), 1.03 (3H,dJ9 Hz,CH₃), 2.11 (3H,s,OCOCH₃), 3.71 (3H,s,CO₂CH₃), 3.84 (3H,s,CO₂CH₃), 4.04 (1H,d,J2.5 Hz,7H), 4.96 and 5.02 (2H,2s,=CH₂), 5.08 (1H,d,J5 Hz,CHOAc), 5.27 (1H,s,3H), 5.80 (1H,d,J15 Hz,CH=CHCHMe), 6.26 (1H,d,J2.5 Hz,6H), 6.86 (1H,dd,J15 Hz,J9 Hz,CH=CHCHMe), 7.10–7.30 (5H,m,Ph).

v) RT 16.9 min, 3,5-dimethyl ester (12 mg); ¹H NMR (CD₃OD) includes δ0.82–0.91 (9H,m,3×CH₃), 1.03 (3H,d,J9 Hz,CH₃), 2.11 (3H,s,OCOCH₃), 3.68 (3H,s,CO₂CH₃), 3.72 (3H,s,CO₂CH₃), 3.98 (1H,br s,7H), 4.97 and 5.02 (2H,2s,=CH₂), 5.08 (1H,d,J5 Hz,CHOAc), 5.37 (1H,s,3H), 5.78 (1H,d,J15 Hz,CH=CHCHMe), 6.42 (1H,br s,6H), 6.77 (1H,dd,J15 Hz,J9 Hz,CH=CHCHMe), 7.10–7.30 (5H,m,Ph).

vi) RT 17.6 min, 4,5-dimethyl ester (1 47 mg); ¹H NMR (CD₃OD) includes δ 0.82–0.90 (9H,m,3×CH₃), 1.03 (3H,d,J9 Hz,CH₃), 2.11 (3H,s,OCOCH₃), 3.67 (3H,s,CO₂CH₃), 3.83 (3H,s,CO₂CH₃), 4.04 (1H,d,J2.5 Hz,7H), 4.97 and 5.03 (2H,2s,=CH₂), 5.08 (1H,d,J5 Hz,CHOAc), 5.22 (1H,s,3H), 5.78 (1H,d,J15 Hz,CH=CHCHMe), 6.28 (1H,d,J2.5 Hz,6H), 6.79 (1H,dd,J15 Hz,J9 Hz,CH=CHCHMe), 7.10–7.30 (5H,m,Ph); ¹³C NMR (CD₃OD) diagnostic values include δ 52.8 (CO₂CH₃), 53.8 (CO₂CH₃), 166.1 (OCOCH=), 167.3 (5-CO₂Me), 170.3 (3-CO₂H), 171.3 (4-CO₂Me), 173.3 (OCOMe).

Analysis Found: C,61.70; H,7.03; C₃₇H₅₀O₁₄ requires: C,61.83; H,7.01%.

vii) RT 25.5 min, 3,4,5-trimethyl ester (18 mg); ¹H NMR (CD₃OD) includes δ 0.82–0.90 (9H,m,3×CH₃), 1.03 (3H,d,J9 Hz,CH₃), 2.11 (3H,s,OCOCH₃), 3.68, 3.73 and 3.83 (9H,3s,3×CO₂CH₃), 4.05 (1H,d,J2.5 Hz,7H), 4.97 and 5.02 (2H,2s=CH₂), 5.07 (1H,d,J5 Hz,CHOAc), 5.28 (1H,s,3H), 5.78 (1H,d,J15 Hz,CH=CHCHMe), 6.29 (1H,d,J2.5 Hz,6H), 6.79 (1H,dd,J15 Hz,J9 Hz,CH=CHCHMe), 7.10–7.30 (5H,m,Ph).

EXAMPLE 39

[1S-[1α(4R*,5S*),3α,4β,5α,6α]]1-(4-Acetyloxy-5-methyl-3 -methylene-6-phenylhexyl)-4,6-dihydroxy-2,8-dioxabicyclo[3.2.1]octane-3,4,5-tricarboxylic acid A solution of Compound A (45 mg) in dry dimethylformamide (0.8 ml) was treated with N-methylhydroxylamine hydrochloride (11.3 mg) and dry triethylamine (0.049 ml). The resulting suspension was stirred at 50° C. for 6 h, then at room temperature for 10 h. The solution was concentrated and the residue dissolved in water (10 ml). This was washed with ether then adjusted to pH1 by addition of 2M hydrochloric acid. The acidic solution was saturated with sodium chloride, ethyl acetate added and the two phase mixture stirred at room temperature for 0.5 h. The organic phase was separated and the aqueous phase extracted with ethyl acetate. The combined organic phases were dried (MgSO$_4$), filtered and the solvent removed under reduced pressure. The residue was purified by reverse-phase HPLC (1 inch Spherisorb, ODS-2) eluting with acetonitrile-water (43:57) acidified with 0.15 mlL$^{-1}$ concentrated sulphuric acid. Appropriate fractions were combined and concentrated in vacuo to remove acetonitrile to give an aqueous solution which was then saturated with sodium chloride and stirred with ethyl acetate for 0.5 h. The organic phase was then separated, and the aqueous phase extracted with ethyl acetate. The combined organic solution were dried (MgSO$_4$), filtered and concentrated to give the title compound (31 mg) as a white solid; δ (CD$_3$OD) includes 0.8–1.0 (m,CH$_3$), 2.10 (s,CH$_3$CO$_2$), 4.76 (s,3-H), 4.99 and 5.03 (2s,C=CH$_2$), 5.10 (d, J5 Hz, CH$_3$CO$_2$CH), 5.39–5.44 (m,6-H), 7.10–7.30 (m,C$_6$H$_5$); HPLC retention time 10.7 min (Spherisorb ODS-2 column, flow rate 1.5 ml/min, eluting with gradient 14.2 to 90.3% acetonitrile/water containing 0.15 ml/L concentrated sulphuric acid over 25 min).

EXAMPLE 40

Characteristics of IMI 332962

After 2–3 weeks growth at 25° C. on oatmeal agar the colonies were smoke grey to mouse grey in colour (Rayner's Mycological Colour Chart, 1970; published by the Commonwealth Agricultural Bureaux) on both the surface and reverse of the colony.

Morphological observations of the strain grown at 25° C. on oatmeal agar were made under an optical microscope. The fungus had no sexual reproductive stage but formed pycnidia, thereby placing it in the class Coelomycetes. The fungus produced rostrate pycnidia with loose hyphae and both aseptate and one-septate conidia. The conidia were approximately 5–9×1.5–3 $\mu$M in dimensions (usually 7–9×1.502.5 $\mu$M). Numerous multiseptate/multicellular, globose structures resembling chlamydospores or pycnidial initials were also observed. Distinct dictyochlamydospores were absent.

The isolate has been identified as a species of the genus Phoma, and the identity confumed by the CAB International Mycological Institute.

EXAMPLE A

Isolation of S(R*,R*)-(E)-4,6-dimethyl-2-octenoic acid

The original filtrate from Example 10 was concentrated under reduced pressure, acidified by adding hydrochloric acid (2M; 10 ml), and extracted with toluene. The toluene solution was washed with brine, dried and chromatographed on silica gel eluting with ethyl acetate: cyclohexane (1:3) to give the title compound (311 mg), [α]+55.7° c D 0.73 in methanol), $v_{max}$ (bromoform) 3400-2300 (O-H), 1691 (C=O), 1646 (C=C) cm$^{-1}$, δ (deuterochloroform) 6.95 (dd, J=15 and 8 Hz, CH=CHCO$_2$), 5.80 (d, J=15 Hz, CHCO$_2$), 2.47 (m, CH—CH=C), 1.45-1.10 (m, CH$_3$CH$_2$, CH$_2$CHMeEt, CH$_2$CHMeEt), 1.08 (d, J=8 Hz, CHCH$_3$CH=), 0.87 (m, CH$_3$CH$_2$), C-6CH$_3$).

EXAMPLE B (i) S(R*,R*)2,4-Dimethylhexanoic acid

The octenoic acid (1.2 g) of Example A above in carbon tetrachloride (14 ml), acetonitrile (14 ml) and ruthenium trichloride trihydrate (40 mg) at 20° C. The mixture was stirred for 2 h, filtered through kieselgeel, and the residue was washed with dichloromethane. The filtrate and washings were transferred into a separating funnel, and the organic lower layer was separated. THe organic solution was washed with water (10 ml), dried (MgSO$_4$), evaporated and distilled under reduced pressure in a bulb-to-bulb distillation apparatus to give the title compound (400 mg) bp 125° C. at 5 mbar, [α]$^{19}$+32° (c D 0.979 in ethanol), $v_{max}$ (CHBr$_3$) 3400-2400, 1739cm$^{-1}$ (carboxylic acid), δ (CDCl$_3$) 11.5-10.0 (br, 1H, CO$_2$H), 2.57 (m, 1H CHCO$_2$H), 1.74 and 1.13 (m, 1H each, CHCH$_2$CH), 1.33 (m, 1H, CH$_2$CHCH$_2$), 1.38 and 1.13 (m, 1H each, CH$_2$CH$_3$), 1.19 (d, J6 Hz, 3H, C-2CH$_3$), 0.89 (d, J7 Hz, 3H, C-4CH$_3$), 0.87 (t, J7 Hz, 3H, CH$_2$CH$_3$).

(ii) S(R*,R*)Methyl2,4-dimethylhexanoate

The product of part (i) above (385 mg) in methanol (10 ml) was treated dropwise with thionyl chloride (0.4 ml, 5.5 mmol) at 0° C. and then the solution was stood at room temperature overnight. The excess methanol was removed by distillation at atmospheric pressure, and the residue was distilled to give the title compound (216 mg), [α]$^{19}$+33° (liquid, 1=0.1 dm, d$^{22}$=0.871), lit$^1$ [α]$^{23}$+DD 32.20 (liquid 1=0.2 dm), $v_{max}$ (CHBr$_3$) 1725cm$^{-1}$(ester), δ (CDCl$_3$) 3.67 (s, 3H, CO$_2$CH$_3$), 2.57 (m, 1H, CH$_2$CHCH$_2$), 1.33 and 1.13 (m, 1H each, CH$_2$CH 3), 1.16 (d, J7 Hz, 3H, C-2H$_3$), 0.89 (d, J7 Hz, 3H, C-4CH$_3$), 0.87 (t, J7 Hz, 3H, CH$_2$CH$_3$) lit$^2$ (NMR spectrum).

1. G. Odham, Arkiv. Kemi., 1966, 26, 367.
2. G. Cimino, G. Sodano and A. Spinella, J. Org. CHem., 1987, 52, 5326.

IN VITRO RESULTS (1) The ability of compounds of the invention to inhibit the enzyme squalene synthase was demonstrated using [2-$^{14}$C] farnesylpyrophosphate as substrate under assay conditions similar to those described by S. A. Biller et al in J Medicinal Chemistry 31(10), 1869–1871 (1988). [$^{14}$C] Squalene was separated from unreacted substrate on thin layer chromatography plates and determined by liquid scintillation counting. Inhibition of squalene synthase was quantified by incubating rat liver homogenate with various concentrations of the test compound in the presence of [2-$^{14}$C] farnesylpyrophosphate. The concentration of compound giving 50% inhibition of [$^{14}$C] squalene production in a 30 minute assay was taken as the IC$_{50}$ value.

In this test Compounds A, B, C, D, E, G, H, I, J, K, L, M, N, O, T, U, V, W, A1, B1 and C1 had IC$_{50}$ values of less than 100 nM.

(2) The in vitro evaluation of the antifungal activity of compounds of the invention was performed by determining the minimum concentration (MIC) of the test compound at which growth of the particular microorganism in a suitable medium failed to occur. In practice, a series of agar plates, each having the test compound incorporated at a particular concentration, was inoculated with a standard culture of a clinically relevant pathogen, for example Candida albicans, and each plate was then incubated at 37° C. for 24 to 48 hours depending on the pathogen. The plates were then examined for the presence or absence of growth of the fungus and the appropriate MIC was noted.

In this test Compounds A, B, D, E, H, I, J, K, M, N, O and A1 had MICs in the range of 0.1 to 31 μg/ml against a variety of clinically relevant pathogens.

Pharmaceutical Examples

In the following examples the term 'Active Ingredient' refers to a compound of the present invention, for example a compound described in the Examples hereinabove.

EXAMPLE 1 - TABLETS

| a) Active Ingredient | 5.0 mg |
|---|---|
| Lactose | 95.0 mg |
| Microcrystalline Cellulose | 90.0 mg |
| Cross-linked Polyvinylpyrrolidone | 8.0 mg |
| Magnesium Stearate | 2.0 mg |
| Compression Weight | 200.0 mg |

The active ingredient, microcrystalline cellulose, lactose and cross-linked polyvinylpyrrolidone are sieved through a 500 micron sieve and blended in a suitable mixer. The magnesium stearate is sieved though a 250 micron sieve and blended with the active blend. The blend is compressed into tablets using suitable punches.

| b) Active Ingredient | 5.0 mg |
|---|---|
| Lactose | 165.0 mg |
| Pregelatinised Starch | 20.0 mg |
| Cross-linked Polyvinylpyrrolidone | 8.0 mg |
| Magnesium Stearate | 2.0 mg |
| Compression weight | 200.0 mg |

The active ingredient, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

EXAMPLE 2- CAPSULES

| a) Active Ingredient | 5.0 mg |
|---|---|
| Pregelatinised Starch | 193.0 mg |
| Magnesium Stearate | 2.0 mg |
| Fill weight | 200.0 mg |

The active ingredient and pregelatinised starch are screened through a 500 micron mesh sieve, blended together and lubricated with magnesium stearate (meshed through a 250 micron sieve). The blend is filled into hard gelatin capsules of a suitable size.

| b) Active Ingredient | 5.0 mg |
|---|---|
| Lactose | 177.0 mg |
| Polyvinylpyrrolidone | 8.0 mg |
| Cross-linked Polyvinylpyrrolidone | 8.0 mg |
| Magnesium Stearate | 2.0 mg |
| Fill weight | 200.0 mg |

The active ingredient and lactose are blended together and granulated with a solution of polyvinylpyrrolidone. The wet mass is dried and milled. The magnesium stearate and cross-linked polyvinylpyrrolidone are screened through a 250 micron sieve and blended with the granule. The resultant blend is filled into hard gelatin capsules of a suitable size.

EXAMPLE 3 - SYRUP

| a) Active Ingredient | 5.0 mg |
|---|---|
| Hydroxypropyl Methylcellulose | 45.0 mg |
| Propyl Hydroxybenzoate | 1.5 mg |
| Butyl Hydroxybenzoate | 0.75 mg |
| Saccharin Sodium | 5.0 mg |
| Sorbitol Solution | 1.0 ml |
| Suitable Buffers | qs |
| Suitable Flavours | qs |
| Purified Water to | 10.0 ml |

The hydroxypropyl methylcellulose is dispersed in a portion of hot purified water together with the hydroxybenzoates and the solution is allowed to cool to room temperature. The saccharin sodium, flavours and sorbitol solution are added to the bulk solution. The active ingredient is dissolved in a portion of the remaining water and added to the bulk solution. Suitable buffers may be added to control the pH in the region of maximum stability. The solution is made up to volume, filtered and filled into suitable containers.

EXAMPLE 4 - INTRANASAL SOLUTION

| a) Preserved solution | % w/w |
|---|---|
| Active Ingredient | 0.1 |
| Dextrose (Anhydrous) | 5.0 |
| Benzalkonium Chloride | 0.02 |
| Suitable buffers | qs |
| Purified Water to | 100 |

The active ingredient and dextrose are dissolved in a portion of the bulk solution. Suitable buffers may be added to control the pH in the region of maximum stability. The solution is made up to volume, filtered and filled into suitable containers.

Alternatively, the solution may be provided as a sterile unit dose presentation such that the preservatives are omitted from the formulation.

| b) Unpreserved sterile solution | % w/w |
|---|---|
| Active Ingredient | 0.1 |
| Dextrose (Anhydrous) | 5.0 |
| Suitable Buffers | qs |
| Purified Water to | 100 |

We claim:

1. A compound of formula (I) or a physiologically acceptable salt thereof:

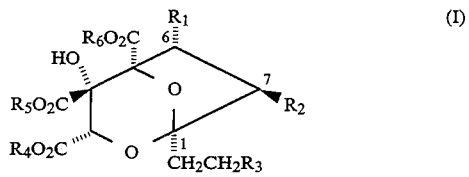

wherein
- $R_1$ represents a hydrogen atom or a hydroxyl group;
- $R_2$ represents a hydrogen atom or a hydroxyl group;
- $R_3$ represents a group selected from the group consisting of:

—C(=CH$_2$)CH(OR$_7$)CH(CH$_3$)CH$_2$Ph, where R$_7$ is a hydrogen atom or an acetyl group;

—C(CH$_3$)$\stackrel{E}{=}$CHCH(CH$_2$R$_8$)CH$_2$Ph, where R$_8$ is a hydrogen or a hydroxyl group;

—C(CH$_2$OH)$\stackrel{Z}{=}$CHCH(CH$_3$)CH$_2$Ph; —C(=CH$_2$)CH(OH)CH(CH$_2$OH)CH$_2$Ph; —C(=CH$_2$)CH(NHCOCH$_3$)CH(CH$_3$)CH$_2$Ph; —C(CH$_2$NHCOCH$_3$)=CHCH(CH$_3$)CH$_2$Ph; and

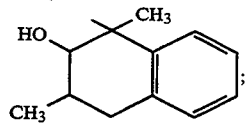

R$_4$, R$_5$ and R$_6$ may each independently represent a hydrogen atom or a methyl group;

with the proviso that when either of R$_1$ and R$_2$ represents a hydrogen atom R$_3$ is a group selected from
—C(=CH$_2$)CH(OR$_7$)CH(CH$_3$)CH$_2$Ph and
—C(CH$_3$)$\stackrel{E}{=}$CHCH(CH$_3$)CH$_2$Ph and when both of R$_1$ and R$_2$ represent hydrogen atoms R$_3$ represents —C(CH$_3$)$\stackrel{E}{=}$CHCH(CH$_3$)CH$_2$Ph.

2. A compound according to claim 1 in which R$_1$ and R$_2$ represent hydroxyl groups.

3. A compound according to claim 1 in which R$_4$, R$_5$ and R$_6$ represent hydrogen atoms.

4. A compound according to claim 1 which is [1S-[1α(4R*,5S*), 3α,4β,5α,6α,7β]]1-(4-acetyloxy-5-methyl-3-methylene-6 -phenylhexyl)-4,6,7-trihydroxy-2,8-dioxabicyclo[3.2.1]octane-3,4,5-tricarboxylic acid; or a physiologically acceptable salt thereof.

5. A compound according to claim 1 in substantially pure form.

6. A method of treatment of a human or non-human animal body to combat diseases associated with hypercholesterolemia and/or hyperlipoproteinemia or to combat fungal diseases, which method comprises administering to said body an effective amount of a compound according to claim 1.

7. A pharmaceutical composition comprising a therapeutically effective amount of a compound according to claim 1 together with one or more carriers and/or excipients.

8. A pharmaceutical composition according to claim 7 in unit dosage form.

9. A compound according to claim 1 which is [1S-[1α(4R *,5S*),3α,4β,5α,7β]]1-(4-acetyloxy-5-methyl-3-methylene-6 -phenylhexyl)-4,7-dihydroxy-2,8-dioxabicyclo[3.2.1]octane-3,4,5-tricarboxylic acid; or a physiologically acceptable salt thereof.

10. A method of treatment of human or non-human animal body to combat fungal disease, which method comprises administering to said body an effective amount of a compound as claimed in claim 1.

11. A method of treatment of human or non-human animal body to combat fungal disease, which method comprises administering to said body an effective amount of a compound as claimed in claim 4.

12. A method of treatment of human or non-human animal body to combat fungal disease, which method comprises administering to said body an effective amount of a compound as claimed in claim 9.

13. A pharmaceutical composition comprising a therapeutically effective amount of a compound according to claim 4 together with one or more carriers and/or excipients.

14. A pharmaceutical composition comprising a therapeutically effective amount of a compound according to claim 9 together with one or more carriers and/or excipients.

* * * * *